(12) United States Patent
Grychowski et al.

(10) Patent No.: US 6,745,760 B2
(45) Date of Patent: Jun. 8, 2004

(54) MEDICAMENT APPLICATOR

(75) Inventors: Jerry Grychowski, Lake Zurich, IL (US); Martin P. Foley, London (CA); Robert Morton, London (CA); Daniel K. Engelbreth, London (CA)

(73) Assignee: Trudell Medical International, London (CA)

( * ) Notice: Subject to any disclaimer, the term of this patent is extended or adjusted under 35 U.S.C. 154(b) by 86 days.

(21) Appl. No.: 10/121,931

(22) Filed: Apr. 12, 2002

(65) Prior Publication Data
US 2002/0170928 A1 Nov. 21, 2002

Related U.S. Application Data
(60) Provisional application No. 60/345,181, filed on Dec. 21, 2001, provisional application No. 60/305,408, filed on Jul. 13, 2001, and provisional application No. 60/291,196, filed on May 15, 2001.

(51) Int. Cl.[7] ............................................. A61M 11/00
(52) U.S. Cl. ........................ 128/200.14; 128/200.23; 128/203.15
(58) Field of Search .................. 128/200.14, 200.17, 128/200.22, 200.23, 203.15, 203.28

(56) References Cited

U.S. PATENT DOCUMENTS

| 165,054 A | 6/1875 | Baldwin |
| 498,851 A | 6/1893 | Jones |
| 1,219,858 A | 6/1917 | Patterson |
| 1,862,083 A | 6/1932 | Hagstrom |
| 2,455,962 A | 12/1948 | Wheeler et al. |
| 2,580,292 A | 12/1951 | Geary et al. |
| 2,587,147 A | 2/1952 | Guion et al |
| 2,630,027 A | 3/1953 | Wunderlich |
| 2,644,452 A | 7/1953 | Brown |
| 2,767,680 A | 10/1956 | Lermer |
| 2,883,086 A | 4/1959 | Davidson et al. |
| 2,939,597 A | 6/1960 | Greene |
| 2,943,730 A | 7/1960 | Tregilgas |
| 2,953,242 A | 9/1960 | Shaw |
| 3,073,468 A | 1/1963 | Anerson |
| 3,085,745 A | 4/1963 | Auberger |
| 3,119,557 A | 1/1964 | Chapman |
| 3,120,318 A | 2/1964 | Rigor |
| 3,148,801 A | 9/1964 | Radeloff et al. |
| 3,151,599 A | 10/1964 | Livingston |
| 3,170,597 A | 2/1965 | Reichenberger |

(List continued on next page.)

FOREIGN PATENT DOCUMENTS

| AU | 598250 B2 | 6/1990 |
| CA | 535518 | 1/1957 |
| DE | 6 603 758 | 7/1969 |

(List continued on next page.)

OTHER PUBLICATIONS

Copies of seven (7) photographs of Pfeiffer discharge apparatus for media (date unknown).
International Search Report for PCT/IB 02/01650, filed on May 14, 2002.

Primary Examiner—Weilun Lo
Assistant Examiner—Michael G. Mendoza
(74) Attorney, Agent, or Firm—Brinks Hofer Gilson & Lione

(57) ABSTRACT

An actuator is used to dispense a medicament from a container having at least a first and second portion. The actuator includes a holder, a trigger member and a push member. The trigger member is pivotally connected to the holder at a pivot axis. The push member is connected to the trigger member. The push member is adapted to move at least the second portion of the container relative to the holder as the push member is pivoted in a first direction. In one preferred embodiment, the trigger member follows a path, and a stop member engages one of the container and push member and immobilizes the push member as the trigger member is moved along a predetermined portion of the path.

65 Claims, 32 Drawing Sheets

U.S. PATENT DOCUMENTS

| | | |
|---|---|---|
| 3,187,963 A | 6/1965 | Anderson |
| 3,191,867 A | 6/1965 | Helms |
| 3,240,389 A | 3/1966 | Genua |
| 3,334,731 A | 8/1967 | Dale |
| 3,344,951 A | 10/1967 | Gervais |
| 3,405,843 A | 10/1968 | Watson, Jr. |
| 3,419,187 A | 12/1968 | Bazarnic |
| 3,446,179 A | 5/1969 | Bender |
| 3,477,561 A | 11/1969 | Espinal |
| 3,495,567 A | 2/1970 | Hayes et al. |
| 3,511,409 A | 5/1970 | Huck |
| 3,549,057 A | 12/1970 | Perez |
| 3,572,282 A | 3/1971 | Trump et al. |
| 3,589,563 A | 6/1971 | Carragan et al. |
| 3,598,294 A * | 8/1971 | Hedrick et al. .......... 222/402.2 |
| 3,612,349 A | 10/1971 | Thomas |
| 3,655,952 A | 4/1972 | Johnson et al. |
| 3,688,945 A | 9/1972 | Harman, Jr. et al. |
| 3,753,417 A | 8/1973 | Garby |
| 3,762,442 A | 10/1973 | Davidson et al. |
| 3,766,882 A | 10/1973 | Babbit, III |
| 3,792,242 A | 2/1974 | Hanson |
| 3,796,348 A | 3/1974 | Zipper |
| 3,797,748 A | 3/1974 | Nozawa et al. |
| 3,802,608 A | 4/1974 | Gullet |
| 3,831,808 A | 8/1974 | Bender |
| 3,831,812 A | 8/1974 | Dolan |
| 3,845,883 A | 11/1974 | Johnson et al. |
| 3,848,774 A | 11/1974 | Schimke |
| 3,886,879 A | 6/1975 | Frost et al. |
| 3,887,099 A | 6/1975 | Gillman et al. |
| 3,921,568 A | 11/1975 | Fish |
| 3,926,326 A | 12/1975 | Grau |
| 3,960,713 A | 6/1976 | Carey |
| 3,977,554 A | 8/1976 | Costa |
| 3,994,421 A | 11/1976 | Hansen |
| 3,995,776 A | 12/1976 | Micallef |
| 4,011,829 A | 3/1977 | Wachsmann et al. |
| 4,029,033 A | 6/1977 | Kerwin et al. |
| 4,034,757 A | 7/1977 | Glover |
| 4,037,719 A | 7/1977 | Perlmutter |
| 4,069,935 A | 1/1978 | Hampel |
| 4,069,942 A | 1/1978 | Marshall et al. |
| 4,078,661 A | 3/1978 | Thomas |
| 4,094,408 A | 6/1978 | Ford |
| 4,162,746 A | 7/1979 | Anderson et al. |
| 4,164,301 A | 8/1979 | Thayer |
| 4,185,776 A | 1/1980 | Nozawa |
| 4,188,984 A | 2/1980 | Lyall |
| 4,220,247 A | 9/1980 | Kramer |
| 4,291,688 A | 9/1981 | Kistler |
| 4,300,548 A | 11/1981 | Jones |
| 4,345,541 A | 8/1982 | Villa-Real |
| 4,347,804 A | 9/1982 | Villa-Real |
| 4,347,853 A | 9/1982 | Gereg et al. |
| 4,350,265 A | 9/1982 | Griffiths et al. |
| 4,354,621 A | 10/1982 | Knickerbocker |
| 4,357,192 A | 11/1982 | Moser |
| 4,365,722 A | 12/1982 | Kramer |
| 4,368,381 A | 1/1983 | Ishiyama |
| 4,394,934 A | 7/1983 | Fegley |
| 4,405,045 A | 9/1983 | Villa-Real |
| 4,419,016 A | 12/1983 | Zoltan |
| 4,432,300 A | 2/1984 | Lyss |
| 4,436,223 A | 3/1984 | Wilson |
| 4,440,306 A | 4/1984 | Van Buskirk et al. |
| 4,489,834 A | 12/1984 | Thackrey |
| 4,500,005 A | 2/1985 | Forrester |
| 4,501,370 A | 2/1985 | Kelley |
| 4,511,150 A | 4/1985 | Seguenot |
| 4,523,933 A | 6/1985 | Laush et al. |
| 4,528,933 A | 7/1985 | Allen |
| 4,534,345 A | 8/1985 | Wetterlin |
| 4,538,744 A | 9/1985 | Weissenborn |
| 4,548,157 A | 10/1985 | Hevoyan |
| 4,562,933 A | 1/1986 | Dennis |
| 4,565,302 A | 1/1986 | Pfeiffer et al. |
| 4,599,508 A | 7/1986 | Smetaniuk |
| 4,634,012 A | 1/1987 | Kelley |
| 4,637,528 A | 1/1987 | Wachinski et al. |
| 4,641,759 A | 2/1987 | Kelley |
| 4,646,936 A | 3/1987 | Frazier et al. |
| 4,662,520 A | 5/1987 | Griffin |
| 4,664,107 A | 5/1987 | Wass |
| 4,666,051 A | 5/1987 | Trick |
| 4,668,218 A | 5/1987 | Virtanen |
| 4,677,975 A | 7/1987 | Edgar et al. |
| 4,693,399 A | 9/1987 | Hickman et al. |
| 4,705,182 A | 11/1987 | Newel-Lewis |
| 4,722,729 A | 2/1988 | Dettbarn et al. |
| 4,723,673 A | 2/1988 | Tartaglia et al. |
| 4,727,886 A | 3/1988 | Conrardy et al. |
| 4,736,871 A | 4/1988 | Luciani et al. |
| D295,787 S | 5/1988 | Hegemann et al. |
| 4,749,093 A | 6/1988 | Trick |
| 4,753,189 A | 6/1988 | Mastman et al. |
| 4,756,423 A | 7/1988 | Holtsch |
| 4,771,769 A | 9/1988 | Hegemann et al. |
| 4,782,966 A | 11/1988 | Thackrey |
| 4,792,664 A | 12/1988 | Schwab |
| 4,801,093 A | 1/1989 | Brunet et al. |
| 4,817,822 A | 4/1989 | Rand et al. |
| 4,830,224 A | 5/1989 | Brison |
| 4,860,738 A | 8/1989 | Hegemann et al. |
| 4,890,572 A | 1/1990 | Huang |
| 4,934,358 A | 6/1990 | Nilsson et al. |
| 4,947,875 A | 8/1990 | Brooks et al. |
| 4,955,371 A | 9/1990 | Zamba et al. |
| 4,969,578 A | 11/1990 | Gander et al. |
| 4,984,158 A | 1/1991 | Hillsman |
| 5,009,338 A | 4/1991 | Barker |
| 5,011,032 A | 4/1991 | Rollman |
| 5,020,527 A | 6/1991 | Dessertine |
| 5,027,808 A * | 7/1991 | Rich et al. ............. 128/203.23 |
| 5,038,972 A | 8/1991 | Muderlak et al. |
| 5,060,643 A | 10/1991 | Rich et al. |
| 5,069,204 A | 12/1991 | Smith et al. |
| 5,082,129 A | 1/1992 | Kramer |
| 5,082,130 A | 1/1992 | Weinstein |
| 5,115,929 A | 5/1992 | Buono |
| 5,174,473 A | 12/1992 | Marelli |
| 5,184,761 A | 2/1993 | Lee |
| 5,188,251 A | 2/1993 | Kusz |
| 5,190,643 A | 3/1993 | Duncan et al. |
| 5,203,840 A | 4/1993 | Graf et al. |
| 5,209,375 A | 5/1993 | Fuchs |
| 5,224,474 A | 7/1993 | Bloomfield |
| 5,227,764 A | 7/1993 | Umemoto |
| 5,228,586 A | 7/1993 | Fuchs |
| 5,242,067 A | 9/1993 | Garby et al. |
| 5,243,970 A | 9/1993 | Ambrosio et al. |
| 5,261,548 A | 11/1993 | Barker et al. |
| 5,263,475 A | 11/1993 | Altermatt et al. |
| 5,284,133 A | 2/1994 | Burns et al. |
| 5,289,946 A | 3/1994 | Fuchs |
| 5,299,701 A | 4/1994 | Barker et al. |
| 5,300,042 A | 4/1994 | Kossoff et al. |
| 5,301,873 A | 4/1994 | Burke et al. |
| 5,328,597 A | 7/1994 | Boldt, Jr. et al. |
| 5,331,953 A | 7/1994 | Andersson et al. |
| 5,335,823 A | 8/1994 | Fuchs et al. |

| | | |
|---|---|---|
| 5,349,945 A | 9/1994 | Wass et al. |
| 5,356,012 A | 10/1994 | Tang et al. |
| 5,363,842 A | 11/1994 | Mishelevich et al. |
| 5,370,267 A | 12/1994 | Schroeder |
| 5,377,869 A | 1/1995 | Weiss et al. |
| 5,382,243 A | 1/1995 | Mulholland |
| RE34,847 E | 2/1995 | Muderlak et al. |
| 5,388,572 A | 2/1995 | Mulhauser et al. |
| 5,392,768 A | 2/1995 | Johansson et al. |
| 5,394,866 A | 3/1995 | Ritson et al. |
| 5,397,028 A | 3/1995 | Jesadanont |
| 5,411,173 A | 5/1995 | Weinstein |
| 5,421,482 A | 6/1995 | Garby et al. |
| 5,437,270 A | 8/1995 | Braithwaite |
| 5,448,042 A | 9/1995 | Robinson et al. |
| 5,482,030 A | 1/1996 | Klein |
| 5,505,192 A | 4/1996 | Samiotes et al. |
| 5,505,195 A | 4/1996 | Wolf et al. |
| 5,509,905 A | 4/1996 | Michel |
| 5,519,197 A | 5/1996 | Robinson et al. |
| 5,520,166 A | 5/1996 | Ritson et al. |
| 5,522,378 A | 6/1996 | Ritson et al. |
| 5,544,647 A | 8/1996 | Jewett et al. |
| 5,549,101 A | 8/1996 | Trofast et al. |
| 5,564,414 A | 10/1996 | Walker et al. |
| 5,611,444 A | 3/1997 | Garby et al. |
| 5,617,844 A | 4/1997 | King |
| 5,622,163 A | 4/1997 | Jewett et al. |
| 5,625,334 A | 4/1997 | Compton |
| 5,625,659 A | 4/1997 | Sears |
| 5,638,970 A | 6/1997 | Garby et al. |
| 5,657,748 A | 8/1997 | Braithwaite |
| 5,676,129 A | 10/1997 | Rocci, Jr. et al. |
| 5,687,710 A | 11/1997 | Ambrosio et al. |
| 5,692,492 A | 12/1997 | Bruna et al. |
| 5,694,882 A | 12/1997 | Marshall |
| 5,718,355 A | 2/1998 | Garby et al. |
| 5,724,957 A | 3/1998 | Rubsamen et al. |
| 5,732,836 A | 3/1998 | Barker et al. |
| 5,740,792 A | 4/1998 | Ashley et al. |
| 5,758,638 A | 6/1998 | Kreamer |
| 5,772,074 A | 6/1998 | Dial et al. |
| 5,794,612 A | 8/1998 | Wachter et al. |
| 5,799,651 A | 9/1998 | Garby et al. |
| 5,803,283 A | 9/1998 | Barker et al. |
| 5,809,997 A | 9/1998 | Wolf |
| 5,819,730 A * | 10/1998 | Stone et al. ............ 128/203.21 |
| 5,826,571 A | 10/1998 | Casper et al. |
| 5,829,434 A | 11/1998 | Ambrosio et al. |
| 5,833,066 A | 11/1998 | Hargus et al. |
| 5,839,621 A | 11/1998 | Tada |
| 5,871,007 A | 2/1999 | Clark, Jr. |
| 5,873,995 A | 2/1999 | Huang et al. |
| 5,882,507 A | 3/1999 | Tanner et al. |
| 5,904,139 A | 5/1999 | Hauser |
| 5,957,896 A | 9/1999 | Bendek et al. |
| 5,988,496 A | 11/1999 | Bruna |
| 6,012,450 A | 1/2000 | Rubsamen |
| 6,029,659 A | 2/2000 | O'Connor |
| 6,033,384 A * | 3/2000 | Py ............................ 604/186 |
| 6,056,118 A | 5/2000 | Hargus et al. |
| 6,076,521 A | 6/2000 | Lindahl et al. |
| 6,082,358 A | 7/2000 | Scarrott et al. |
| 6,082,592 A | 7/2000 | McKenna et al. |
| 6,119,684 A | 9/2000 | Nohl et al. |
| 6,138,669 A | 10/2000 | Rocci, Jr. et al. |
| 6,142,339 A | 11/2000 | Blacker et al. |
| 6,148,815 A | 11/2000 | Wolf |
| 6,149,054 A | 11/2000 | Cirrillo et al. |
| 6,161,724 A | 12/2000 | Blacker et al. |
| 6,164,494 A | 12/2000 | Marelli |
| 6,173,868 B1 | 1/2001 | DeJonge |
| 6,196,419 B1 | 3/2001 | Haney et al. |
| 6,202,642 B1 | 3/2001 | McKinnon et al. |
| 6,223,744 B1 | 5/2001 | Garon |
| 6,234,168 B1 | 5/2001 | Bruna |
| 6,283,365 B1 | 9/2001 | Bason |
| 6,302,101 B1 | 10/2001 | Py |
| 6,305,580 B1 | 10/2001 | Chen |
| 6,328,035 B1 * | 12/2001 | Wakefield et al. ...... 128/203.23 |
| 6,328,037 B1 | 12/2001 | Scarrott et al. |
| 6,336,453 B1 | 1/2002 | Scarrott et al. |
| 6,338,422 B1 | 1/2002 | DeJong |
| 6,360,739 B1 | 3/2002 | Rand et al. |
| 6,364,166 B1 | 4/2002 | Ritsche et al. |
| 6,415,784 B1 * | 7/2002 | Christrup et al. ....... 128/200.23 |
| 6,425,392 B1 | 7/2002 | Sosiak |
| 6,431,168 B1 | 8/2002 | Rand et al. |
| 6,435,372 B1 | 8/2002 | Blacker |
| 6,446,627 B1 | 9/2002 | Bowman et al. |
| 6,474,331 B1 | 11/2002 | Rand et al. |
| 6,516,799 B1 | 2/2003 | Greenwood et al. |
| 6,561,384 B2 | 5/2003 | Blacker et al. |
| 6,595,205 B2 * | 7/2003 | Andersson et al. .... 128/200.23 |
| 6,601,582 B2 | 8/2003 | Rand et al. |
| 2002/0008122 A1 | 1/2002 | Ritsche et al. |
| 2002/0017294 A1 | 2/2002 | Py |
| 2002/0153005 A1 | 10/2002 | Scarrott et al. |

FOREIGN PATENT DOCUMENTS

| | | |
|---|---|---|
| DE | DT 27 02 539 A1 | 1/1977 |
| DE | 3336486 A1 | 4/1984 |
| DE | G 8 590 143.1 | 10/1985 |
| DE | G 86 02 238.5 | 5/1986 |
| DE | 44 11 031 A1 | 1/1995 |
| DE | 196 10 456 A1 | 9/1997 |
| EP | 0 0288 929 A2 | 5/1981 |
| EP | 0 098 939 A2 | 1/1984 |
| EP | 0 114 617 A2 | 8/1984 |
| EP | 0 063 599 | 6/1986 |
| EP | 0 230 323 B1 | 7/1987 |
| EP | 0 236 871 A2 | 9/1987 |
| EP | 0 269 496 A2 | 6/1988 |
| EP | 0 280 104 B1 | 8/1988 |
| EP | 0 488 609 A1 | 6/1992 |
| EP | 0 559 757 B1 | 9/1993 |
| EP | 0 949 584 A2 | 10/1999 |
| GB | 659132 | 10/1951 |
| GB | 998148 | 7/1965 |
| GB | 1058636 | 2/1967 |
| GB | 1 290 484 | 9/1972 |
| GB | 1317315 | 5/1973 |
| GB | 2 036 695 A | 7/1980 |
| GB | 2 063 075 A | 6/1981 |
| GB | 2 092 991 A | 8/1982 |
| GB | 2 104 393 A | 3/1983 |
| GB | 2 191 032 A | 12/1987 |
| GB | 2 195 544 A | 4/1988 |
| GB | 2 348 928 A | 10/2000 |
| JP | 10043648 A | 2/1998 |
| WO | WO 86/02275 | 4/1986 |
| WO | WO 87/04354 | 8/1987 |
| WO | WO 90/10470 | 9/1990 |
| WO | WO 91/06334 | 5/1991 |
| WO | WO 92/07600 | 5/1992 |
| WO | WO 92/09324 | 6/1992 |
| WO | WO 92/15353 | 9/1992 |
| WO | WO 92/17231 | 10/1992 |
| WO | WO 93/24167 | 12/1993 |
| WO | WO 94/11272 | 5/1994 |
| WO | WO 94/14492 | 7/1994 |
| WO | WO 95/34874 | 12/1995 |

| | | | | | | |
|---|---|---|---|---|---|---|
| WO | WO 96/16686 | 6/1996 | | WO | WO 99/57019 | 11/1999 |
| WO | WO 96/16687 | 6/1996 | | WO | WO 00/09187 | 2/2000 |
| WO | WO 96/39337 | 12/1996 | | WO | WO 00/59806 | 10/2000 |
| WO | WO 97/12686 | 4/1997 | | WO | WO 01/28887 A1 | 4/2001 |
| WO | WO 98/01822 | 1/1998 | | WO | WO 02/44056 A1 | 6/2002 |
| WO | WO 98/56444 | 12/1998 | | | | |
| WO | WO 98/56445 | 12/1998 | | | | |
| WO | WO 99/36115 | 7/1999 | | | | |

* cited by examiner

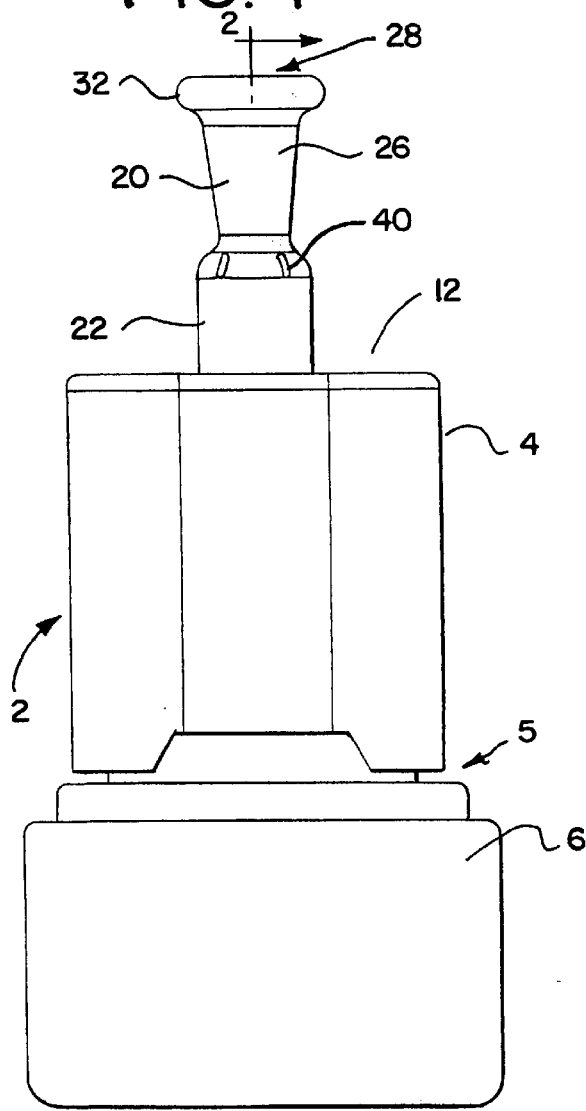
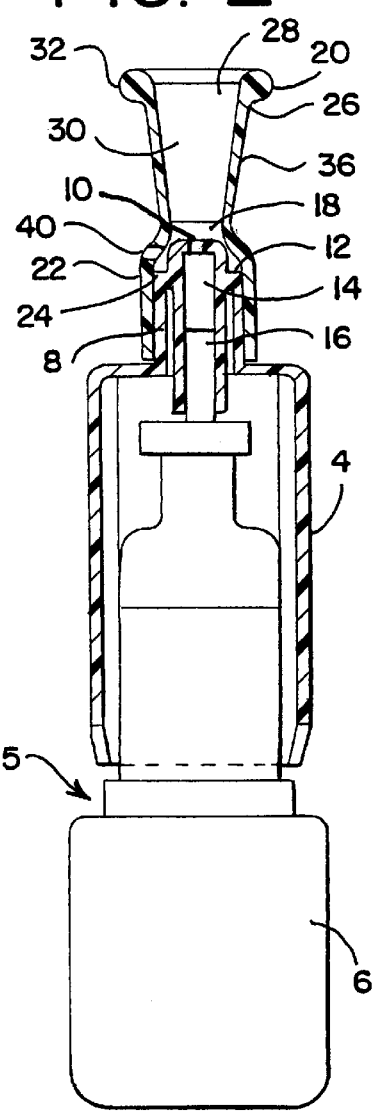
FIG. 1
FIG. 2
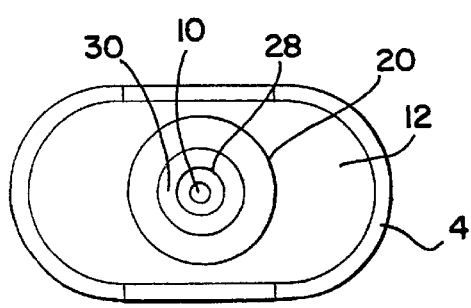
FIG. 3

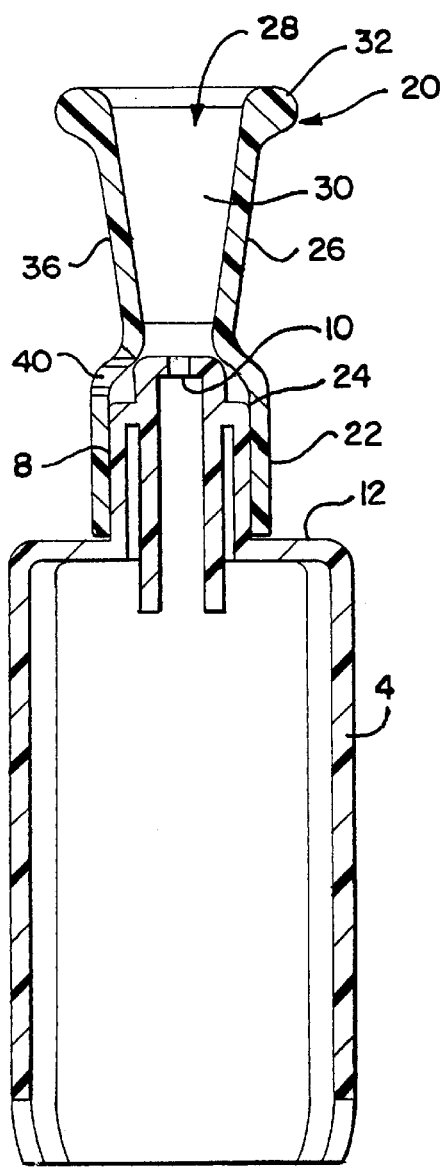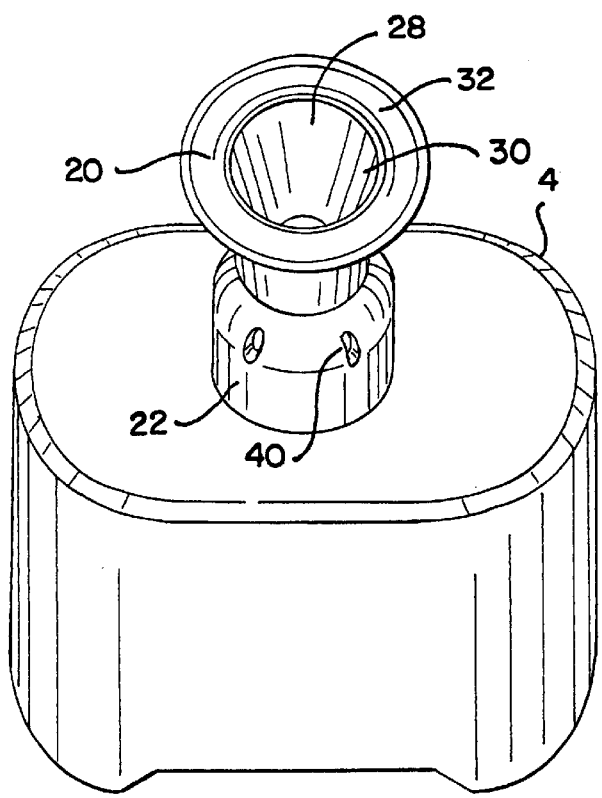

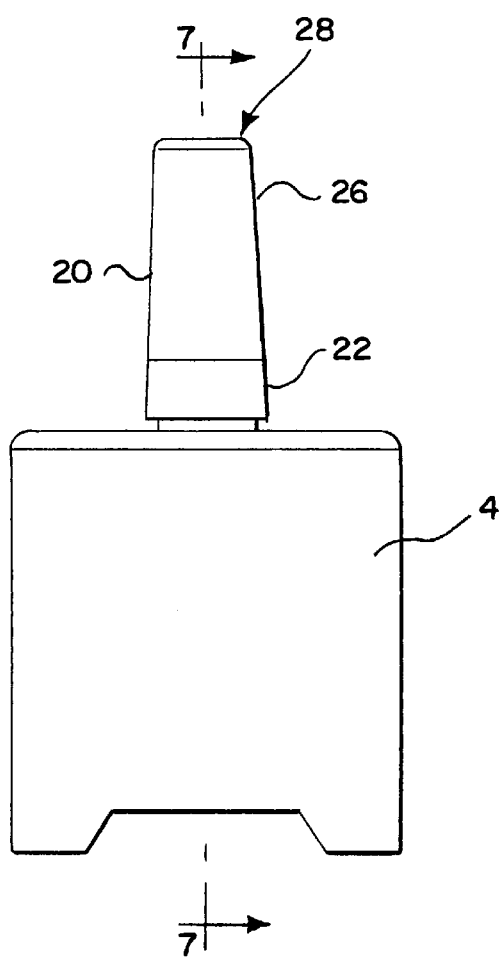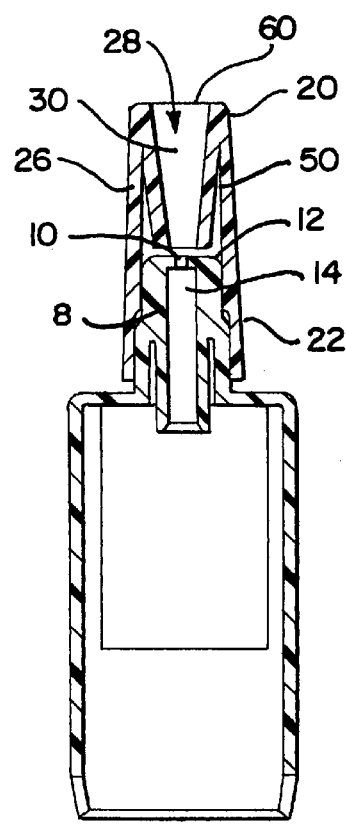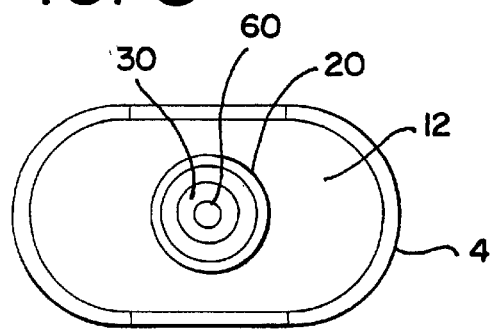

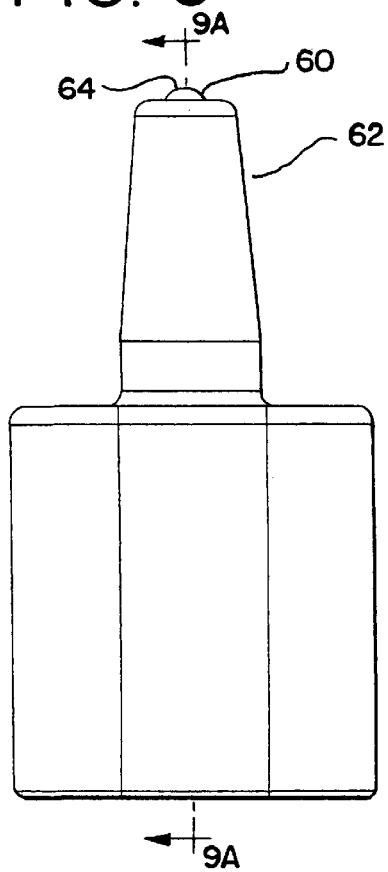
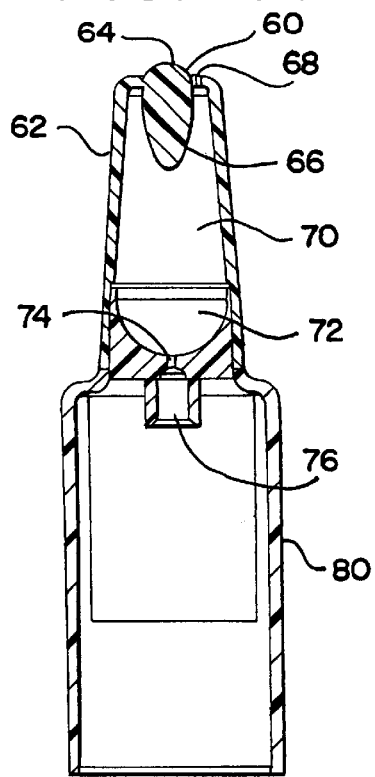
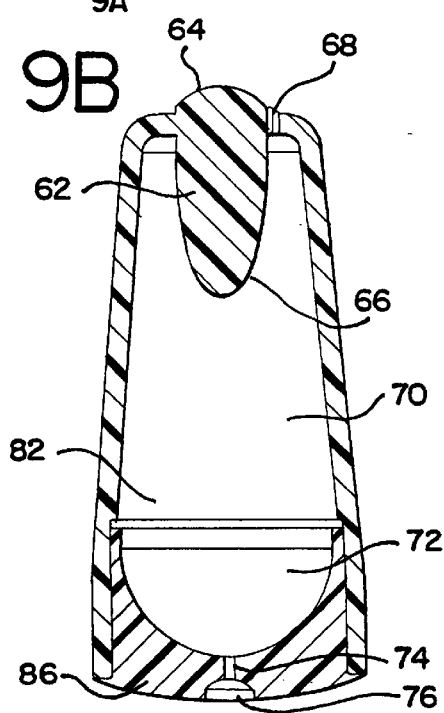
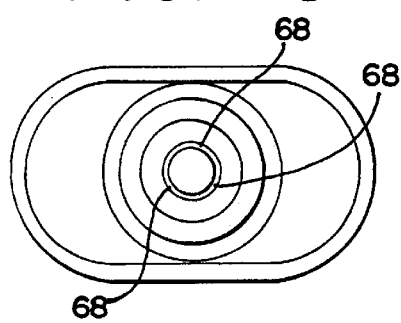

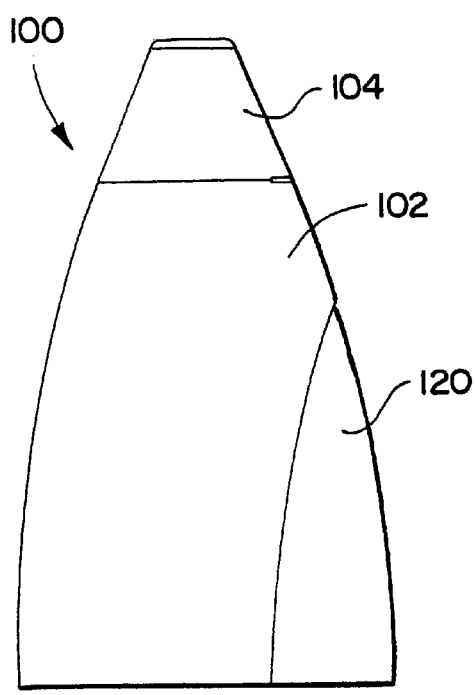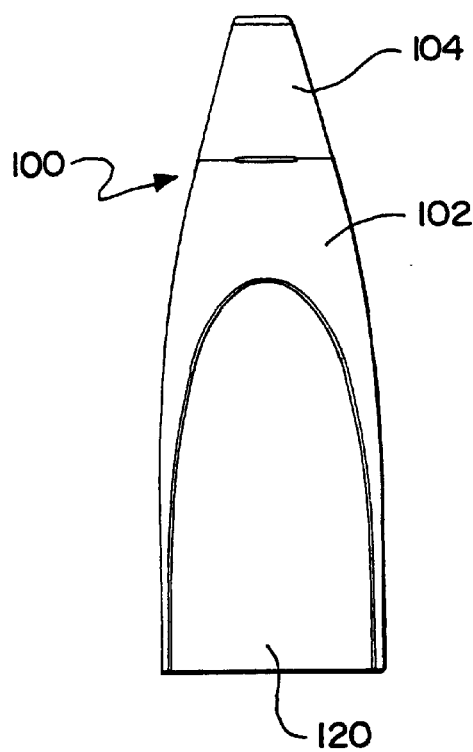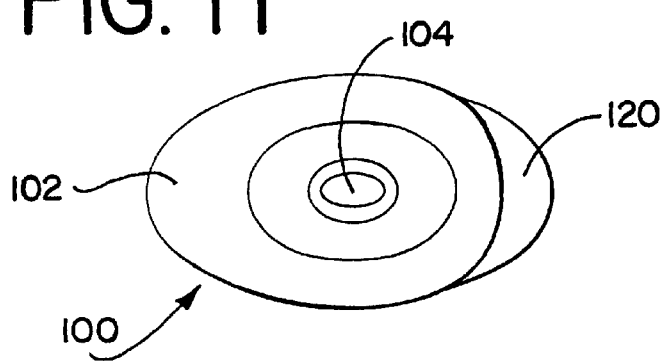

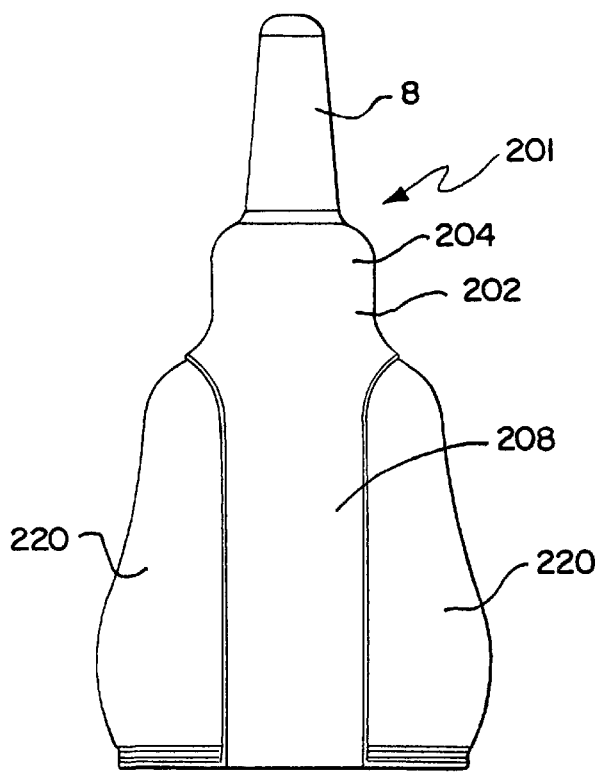
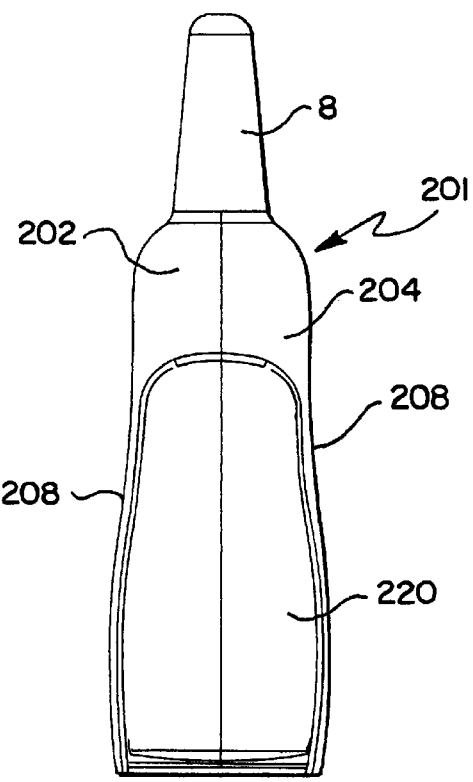
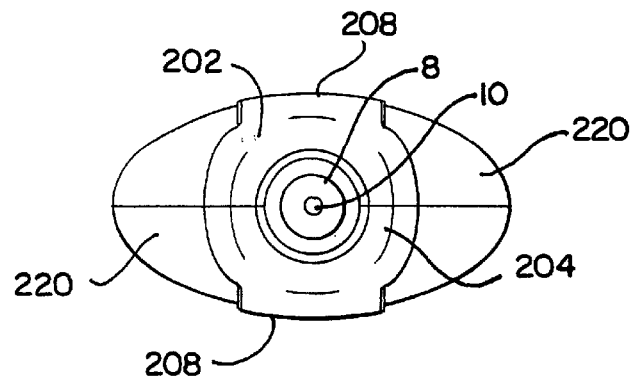

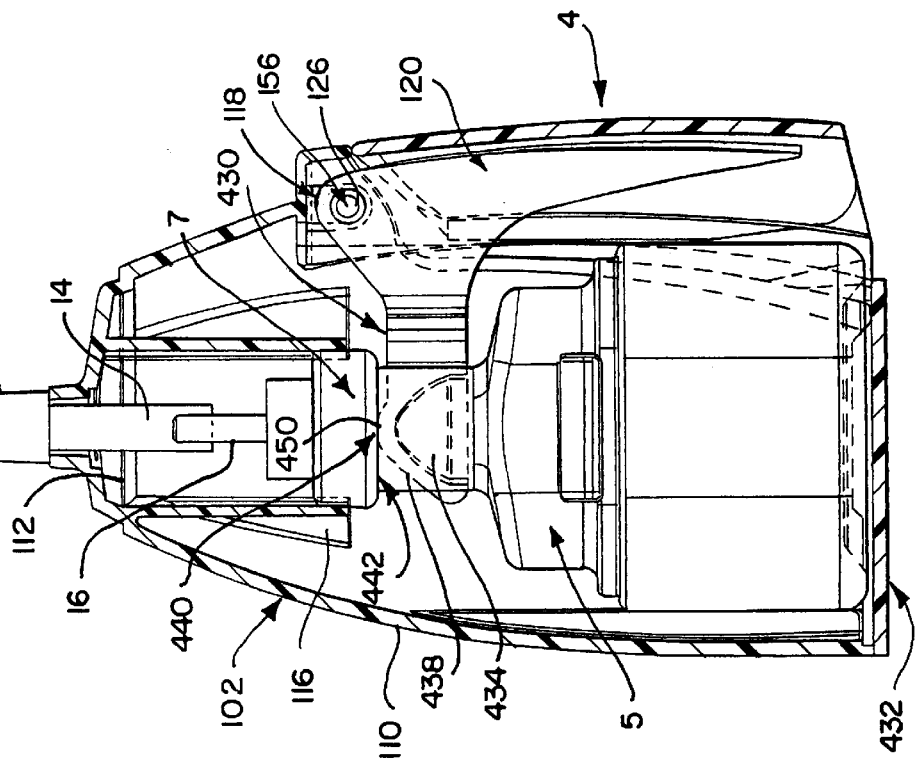
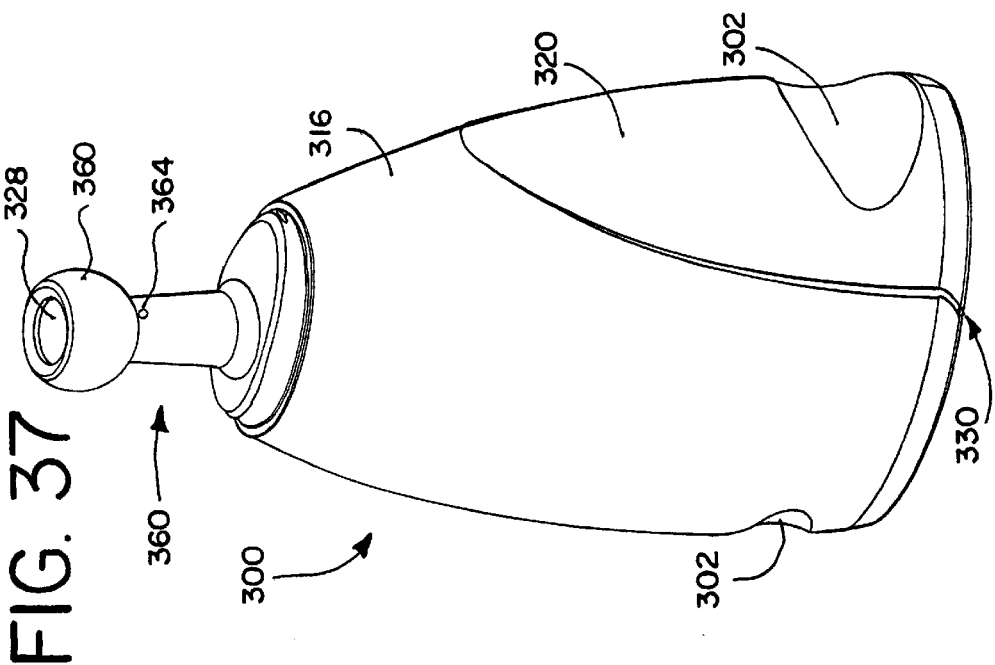

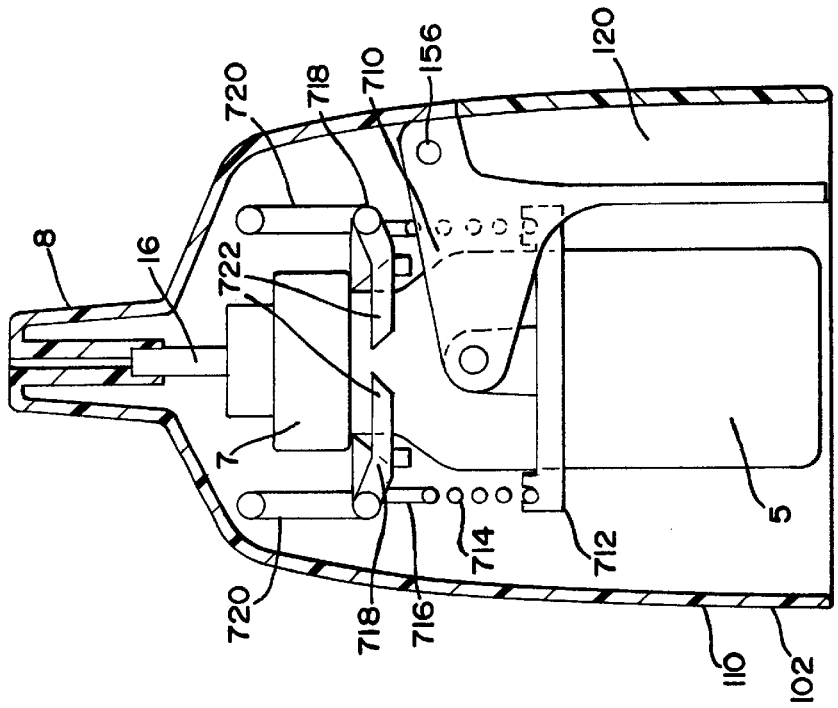
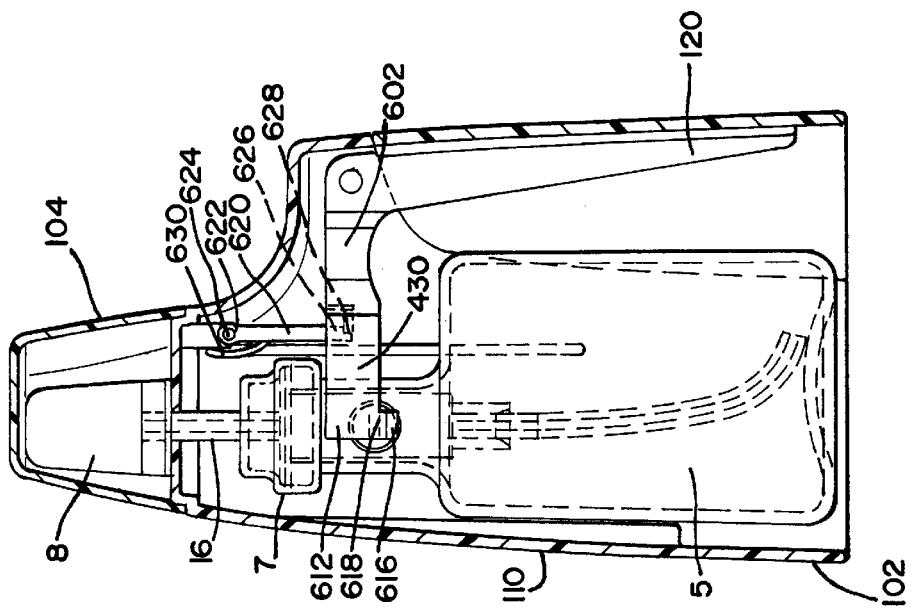

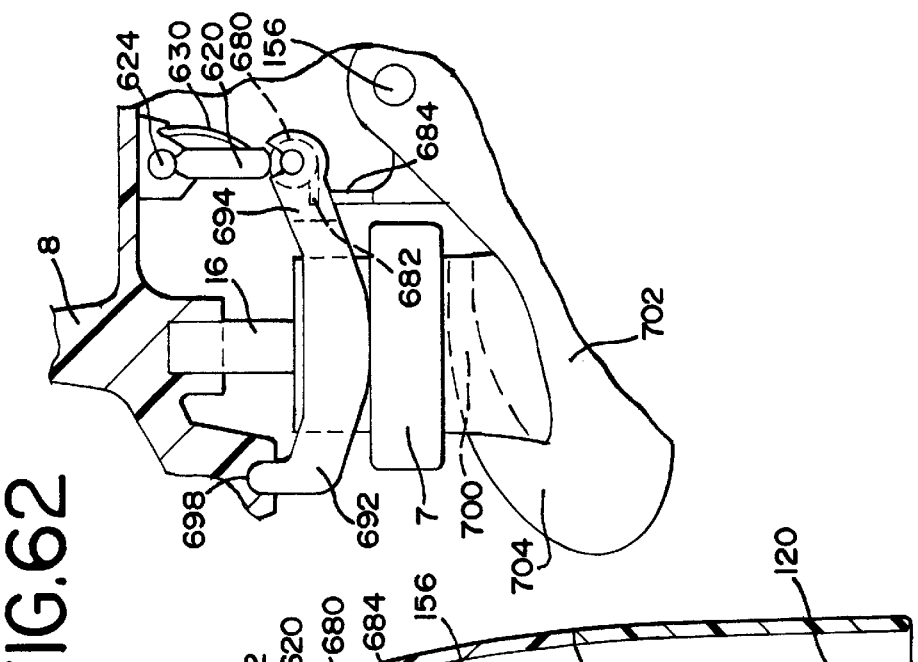
FIG. 62
FIG. 61
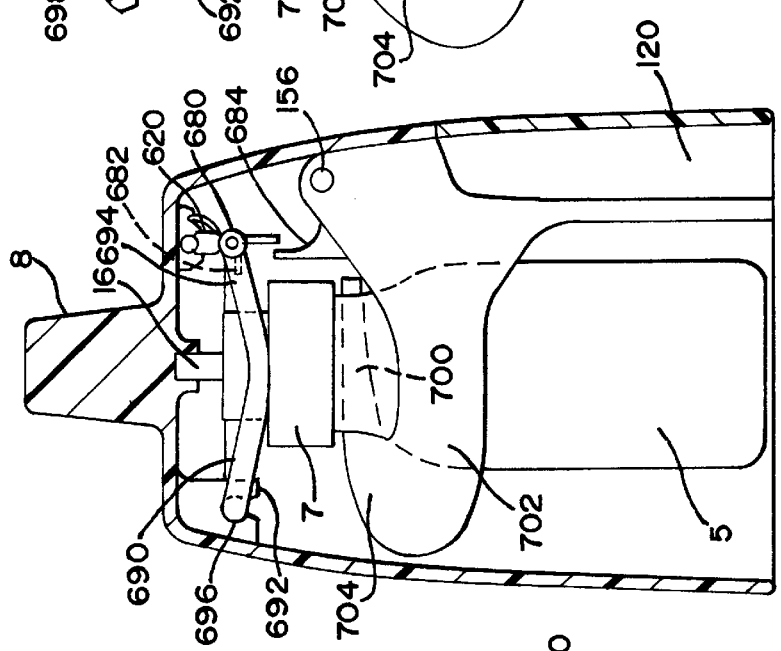
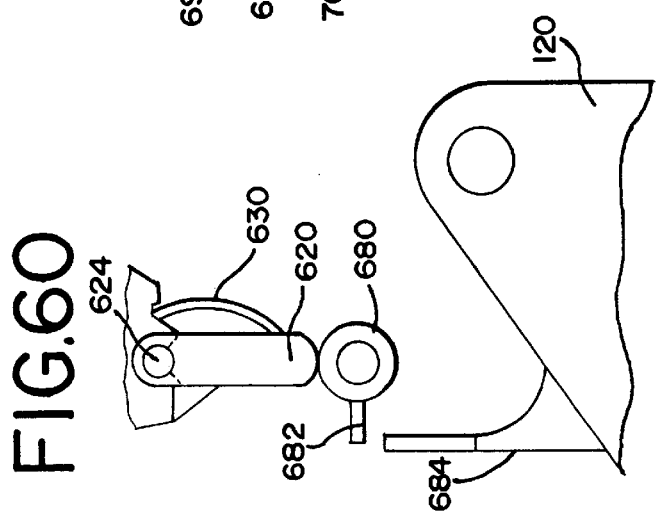
FIG. 60

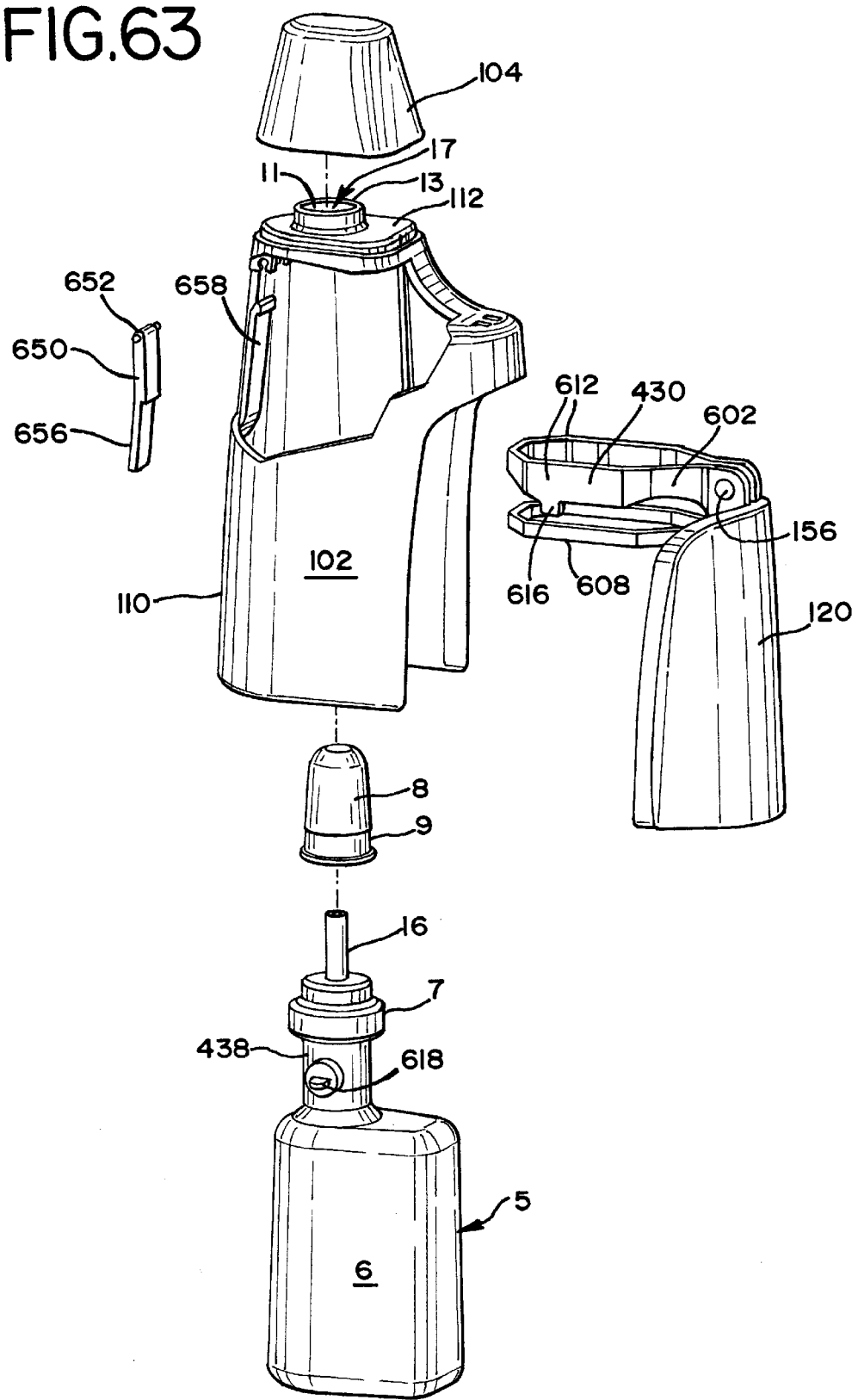

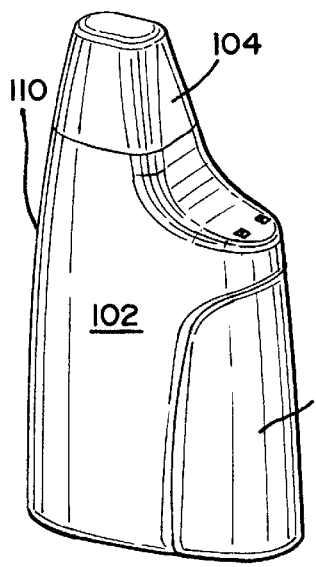
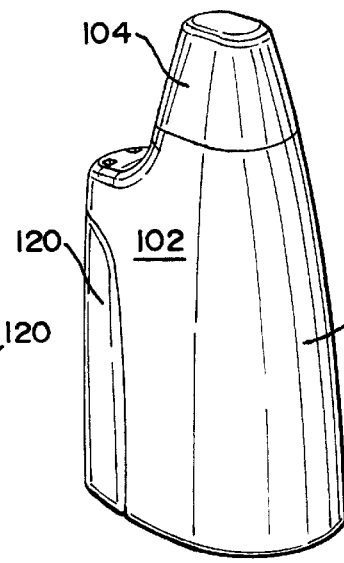
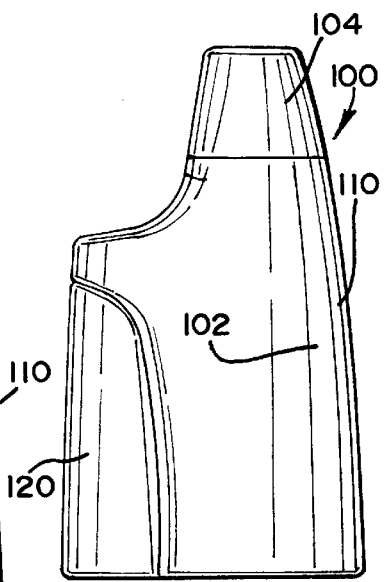
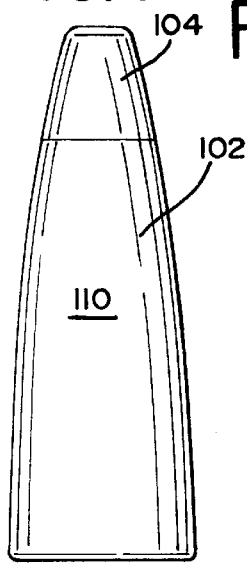
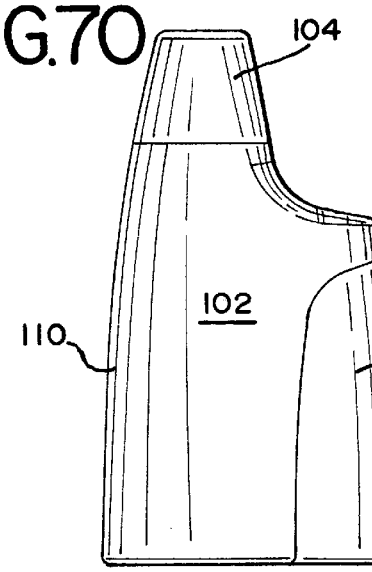
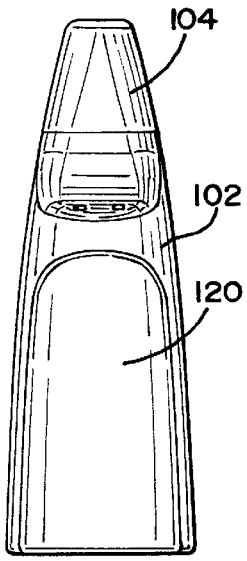
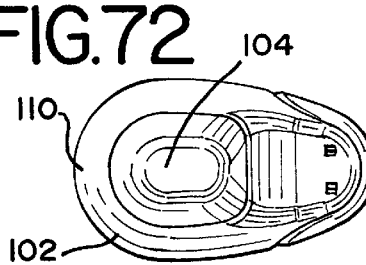
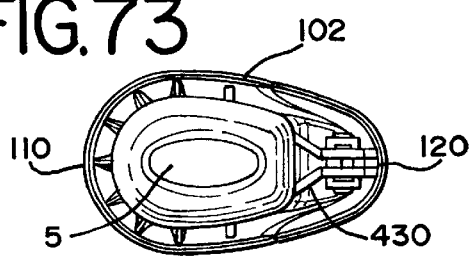

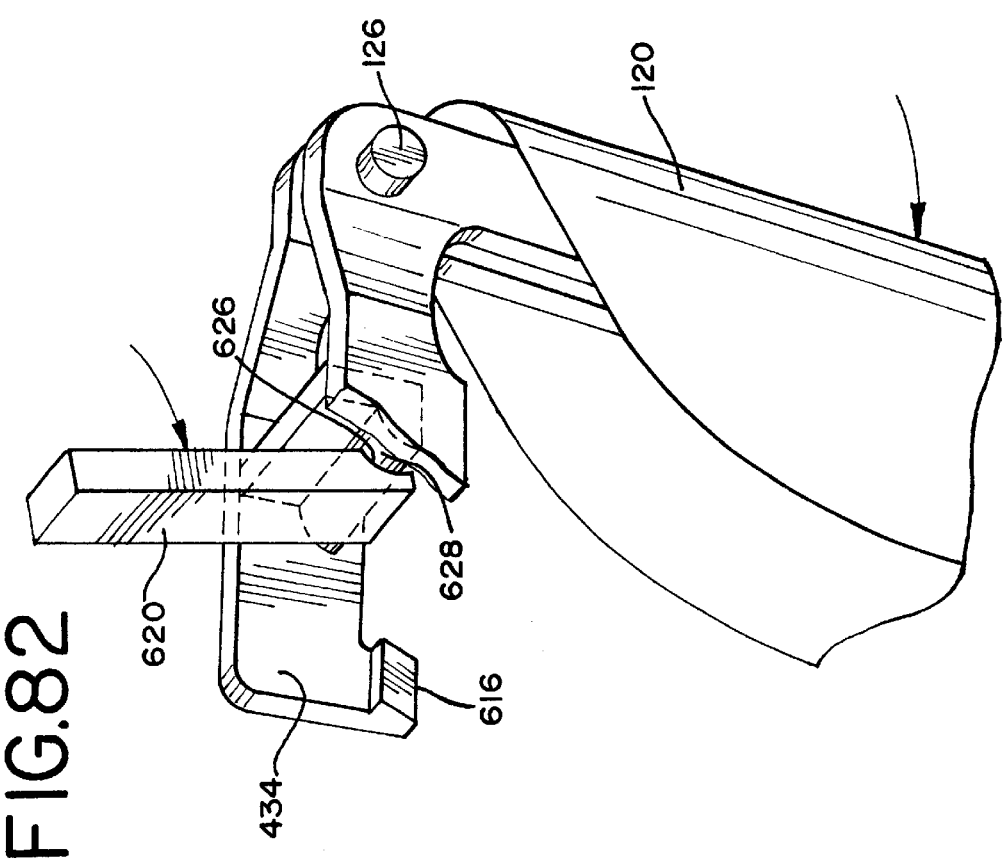
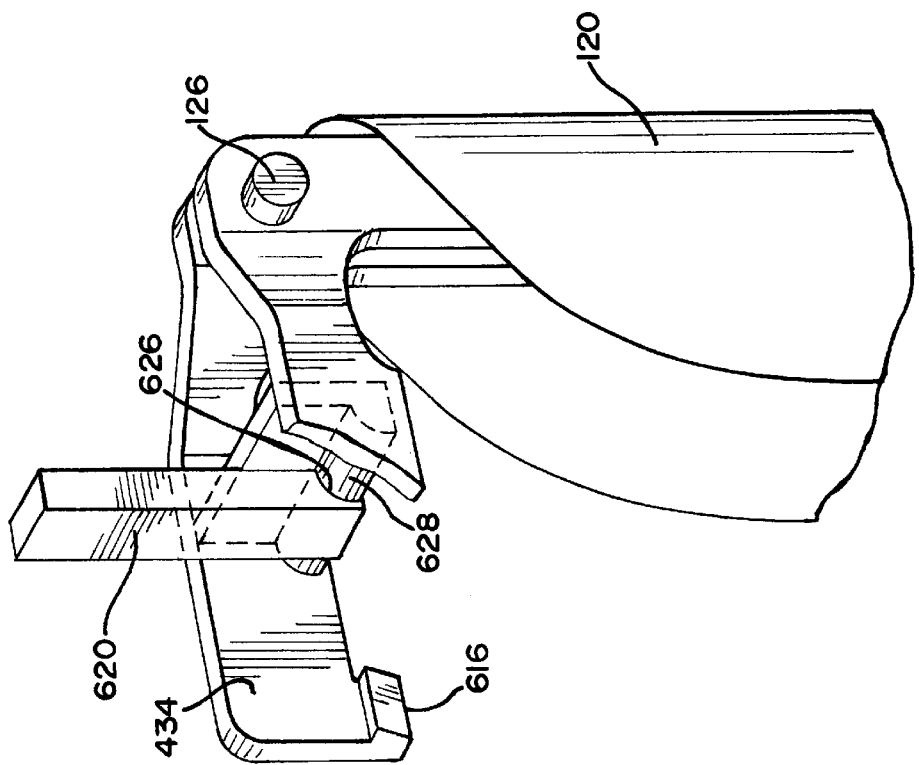

MEDICAMENT APPLICATOR

This application claims the benefit of U.S. Provisional Application Ser. No. 60/345,181, filed Dec. 21, 2001, U.S. Provisional Application Ser. No. 60/305,408, filed Jul. 13, 2001, and U.S. Provisional Application Ser. No. 60/291,196, filed May 15, 2001, all of which are hereby incorporated herein by reference.

FIELD OF THE INVENTION

The invention relates generally to medicament applicators, and in particular, to an actuator used to actuate a container for the administration of a medication or other substance to the nasal cavities and/or lungs of a user.

BACKGROUND

The nose can be an important route for the delivery of various substances aimed at treating various ailments, including various upper respiratory ailments such as rhinitis and sinusitis. Most of the substances delivered to a user through their nose, and in particular to the user's nasal membranes, are delivered in aerosol or aqueous form through nasal medicament applicators, including pressurized metered dose nasal inhalers, nasal sprayers, and dry powder inhalers. For example, nasal sprayers transform a liquid substance into airborne particles for application to the nasal cavity. Such a device generally includes a container filled with a liquid substance and having an actuator portion.

One of the more significant problems with nasal sprayers is nasal drip and oral ingestion of the substance. These problems are caused by airborne particles that are too large to be absorbed by the targeted nasal area (i.e. the nasal turbinates). Rather than reaching, or being absorbed by, the target area in the nasal cavity, these particles tend to fall back out of the nose or make their way to the back of the throat and eventually into the stomach. The problem is further compounded by the fact that the larger particles comprise the most medication, thus resulting in wastage of medication. In addition, another problem with such devices is that at the end of an application, there may be a few large droplets of medication barely clearing the tip of a nozzle, or other member adapted to be inserted into the nose of the user. Typically, such large droplets are caused by the diminishing energy levels experienced at the end of the flow burst, which results from the physics involved during the application.

Typically, nasal sprayers are held with the index and middle finger positioned on opposite sides of a nosepiece, or nozzle, and the user's thumb positioned under the container that holds the medication. Similarly, pressurized metered dose inhalers are typically actuated by holding an actuator boot with the user's thumb and thereafter pushing on the container. Often, in order to place the nosepiece properly in the nostril, or a mouthpiece in the mouth, the hand and wrist are bent or arranged in an awkward position, which can result in discomfort to the user, and/or misalignment of the nozzle with the nasal membranes, with an attendant misalignment of the medication plume. In addition, users often do not actuate the device with a firm, brisk motion, which can result in poor aerosolization of the medication. In addition, the actuation may tend to move the nozzle away from the target area in the nose. Such uncoordinated and/or weak actuation can result in wasted medication and inadequate treatment.

Nasal applicators also typically are not provided with an indicator mechanism that would indicate the number of doses of medicament or substance that have been dispensed from or remain in the container of medicament. Therefore, such applicators typically do not alert a user that the container should be refilled or replaced.

SUMMARY

Briefly stated, in one aspect, various preferred embodiments of applicators are aimed at addressing one or more problems associated with devices used to deliver a substance, preferably a medicament, to the nose or mouth. In one embodiment, a nasal applicator includes an actuator comprising a nozzle with an end having a first outlet and a diffuser comprising a first portion and a second portion. The first portion is disposed on the nozzle and the second portion forms a passageway communicating with the first outlet. The second portion has a second outlet communicating with the passageway. The second outlet is spaced from the first outlet. Preferably, the passageway is tapered. In a preferred embodiment, the first portion comprises an inlet, which communicates with the passageway, located adjacent the first outlet.

In one preferred embodiment, the nozzle and diffuser are integrally molded. In such an embodiment, the diffuser, otherwise referred to as a nozzle, includes a passageway having a tapered portion.

A method for dispensing a substance into a nasal cavity of a user comprises inserting an end of the diffuser into the nasal cavity, dispensing the substance from the applicator into the passageway and dispensing the substance from the passageway through the second outlet into the nasal cavity. In one preferred embodiment, the user further inhales air through the inlet and into the passageway.

In another aspect, an actuator is used to dispense a medicament from a container having at least a first and second portion. The actuator comprises a holder that is adapted to engage at least the first portion of the container and a trigger member moveably connected to the holder. The trigger member is moveable between at least a first trigger position and a second trigger position. A push member is coupled to the trigger member and is moveably connected to the holder. The push member is moveable between at least a first pusher position and a second pusher position as the trigger member is moved between the first and second trigger positions. The push member is adapted to move at least the second portion of the container relative to the holder as the push member is moved from the first pusher position to the second pusher position.

In one preferred embodiment, the trigger member is pivotally connected to the holder and the push member is hingedly connected to the trigger member. In one preferred embodiment, the push member comprises a first and second push member. In another preferred embodiment, the trigger member comprises a first and second trigger member.

In another preferred embodiment, a trigger member is pivotally connected to a holder at a pivot axis. The trigger member is pivotable about the pivot axis in a first direction toward a grippable portion and a second direction opposite the first direction. A push member is connected to the trigger member and is pivotable about the pivot axis in the first direction as the trigger member is pivoted in the first direction. The push member is pivotable about the pivot axis in the second direction as the trigger member is pivoted in the second direction. The push member is adapted to move at least the second portion of the container relative to the holder as the push member is pivoted in the first direction.

In one preferred embodiment, the push member includes an engagement portion adapted to engage the container. In one preferred embodiment, the actuator includes a stop member moveable between an engaged position, wherein the stop member is engaged with at least one of the push member and the container and immobilizes the engagement portion, and a disengaged position. In one preferred embodiment, a trip member is coupled to one of the push member and is moveable between at least an engaged position, wherein the trip member is engaged with the stop member after the trigger member has moved along a predetermined portion of a path of travel as it moves in the first direction, and a disengaged position. The trip member disengages the stop member from the push member when the trip member is moved to the engaged position.

In another aspect, the actuator includes an indicator mechanism. The indicator mechanism includes an indicator member that is rotatably mounted to the holder and a drive mechanism connected between the indicator member and at least one of the trigger member and the push member. Preferably, a predetermined number of movements of at least one of the trigger member and the push member in at least one of the first and second directions causes the drive mechanism to move the indicator member an incremental amount. In one preferred embodiment, the predetermined number of movements is one. Also in one preferred embodiment, the drive mechanism includes a pawl engaging a ratchet gear and a worm coaxially mounted with the ratchet wheel. The worm meshes with and moves the indicator member.

In another aspect, a method for dispensing a medicament from a container comprises engaging at least a first portion of a container with a holder, moving a trigger member relative to the holder between at least a first trigger position and a second trigger position, moving a push member with the trigger member between at least a first pusher position and a second pusher position as the trigger member is moved between at least the first and second trigger positions, engaging at least a second portion of the container with the push member, and moving the second portion of the container relative to the holder with the push member as the push member moves between at least the first and second pusher positions.

In another preferred embodiment, the method includes engaging at least the first portion of the container with the holder, pivoting the trigger member about the pivot axis in a first direction, pivoting the push member about the pivot axis in the first direction and engaging at least the second portion of the container with the push member. The method further includes moving the second portion of the container relative to the holder and the first portion of the container with the push member as the push member pivots about the pivot axis in the first direction. In one preferred embodiment, the method further includes engaging one of the container and push member with a stop member and thereby immobilizing the engagement portion of the push member as the trigger member is pivoted in the first direction along at least a portion of a path of the movement of the trigger member. Preferably, the method further comprises engaging the stop member with a trip member and disengaging the stop member from one of the push member and the container, and thereafter moving the second portion of the container with the push member.

In one preferred embodiment, the method further includes indicating the number of doses remaining in or dispensed from the container. In yet another aspect, various methods for assembling an actuator are provided.

The presently preferred embodiments provide significant advantages over other medicament applicators, including various nasal sprayers. In particular, the applicator creates a better particle size distribution to increase the proportion of particles reaching and being absorbed by the targeted nasal area. By achieving this objective, nasal drip and oral ingestion will be reduced. In particular, the applicator reduces the amount of large aerosol particles leaving the nasal sprayer as well as slowing down the aerosol as it leaves the nasal sprayer. This reduction of speed allows the remaining aerosol particle to land on the interior turbinate and the nasal floor where benefits of the medication can be maximized.

The presently preferred embodiments of the actuators also provide significant advantages. In particular, the configuration of the trigger member and push member conforms to the natural position of the user's hand, and allows for better positioning of the fingers and thumb. In addition, actuation is effected simply by squeezing of the trigger member, which results in a more brisk, upward motion of the container and a better aerosolization of the medicament. Moreover, the squeezing of the trigger member is preferably performed laterally relative to the movement of the container, and does not tend to move the nozzle relative to the target area. The various holder, trigger member and push member can be assembled by snap-fit, which reduces the part count and simplifies the manufacturing process. In addition, the actuator has an appealing aesthetic appearance, with various surfaces that can be decorated with various information, including source and medication identifiers.

The stop member also provides significant advantages. In particular, the stop member allows the trigger member to temporarily store energy in a spring acting on the engagement portion of the push member. In various preferred embodiments, the spring is disposed between the trigger member and the push member, or between various components of the push member. When a predetermined, desired amount of potential energy is stored or accumulated in the spring, the stop member is dislodged, for example by a trip member, such that the energy can be released or dissipated from the spring as it acts upon the container via the push member. In this way, a consistent, repeatable actuation force is applied to the container, with the actuation avoiding various dispensing problems associated with uncoordinated or weak actuation of the container and actuator. As such, the actuator enhances and provides more consistent treatment while avoiding wasted medication.

The indicator mechanism also provides significant advantages. In particular, the indicator member indicates to the user that the container should be replaced. In this way, the user can plan ahead in obtaining refills or new containers.

The foregoing paragraphs have been provided by way of general introduction, and are not intended to limit the scope of the following claims. The present invention, together with further objects and advantages, will be best understood by reference to the following detailed description taken in conjunction with the accompanying drawings.

BRIEF DESCRIPTION OF THE DRAWINGS

FIG. 1 front elevated view of one embodiment of a nasal applicator.

FIG. 2 is a cross-sectional view of the nasal applicator taken along line 2—2 in FIG. 1.

FIG. 3 is a top view of the nasal applicator.

FIG. 4 is an enlarged cross-sectional view of the nasal applicator.

FIG. 5 is a perspective view of a nasal applicator.

FIG. 6 front elevated view of an alternative embodiment of a nasal applicator.

FIG. 7 is a cross-sectional view of the nasal applicator taken along line 7—7 in FIG. 6.

FIG. 8 is a top view of the nasal applicator.

FIG. 9 is a front elevated view of a nasal applicator with a baffle member.

FIG. 9A is a cross-sectional view of the applicator shown in FIG. 9 taken along line 9A—9A.

FIG. 9B is a partial enlarged view of a portion of the applicator shown in FIG. 9A.

FIG. 9C is a top view of the applicator shown in FIG. 9.

FIG. 10 is a front elevation view of a nasal applicator.

FIG. 11 is a top plan view of the applicator shown in FIG. 10.

FIG. 12 is a side elevation view of the applicator shown in FIG. 10.

FIG. 17 is a front elevation view of an alternative embodiment of a nasal applicator.

FIG. 18 is a top plan view of the applicator shown in FIG. 17.

FIG. 19 is a side elevation view of the applicator shown in FIG. 17.

FIG. 37 is a perspective view of an alternative embodiment of a nasal applicator.

FIG. 38 is a front elevation view of an alternative embodiment of a nasal applicator.

FIG. 54 is a front elevation view of an alternative embodiment of a nasal applicator.

FIG. 55 is a front elevation view of an alternative embodiment of a nasal applicator.

FIG. 60 is a partial enlarged view of one preferred embodiment of a stop member, pivot member and trip member.

FIG. 61 is a front elevation view of an alternative embodiment of a nasal applicator.

FIG. 62 is an partial view of an alternative embodiment of a nasal applicator.

FIG. 63 is an exploded perspective view of the applicator shown in FIG. 53.

FIG. 66 is a perspective view of one preferred embodiment of an applicator with a cap applied thereto.

FIG. 67 is an opposite perspective view of the applicator shown in FIG. 66.

FIG. 68 is a rear view of the applicator shown in FIG. 66.

FIG. 69 is a left side view of the applicator shown in FIG. 66.

FIG. 70 is a front view of the applicator shown in FIG. 66.

FIG. 71 is a right side view of the applicator shown in FIG. 66.

FIG. 72 is a top view of the applicator shown in FIG. 66.

FIG. 73 is a bottom view of the applicator shown in FIG. 66.

FIG. 81 is a partial perspective view of an alternative embodiment of a trigger member, push member and stop member in an at-rest position.

FIG. 82 is a partial perspective view of the trigger member, push member and stop member of FIG. 81 shown in an actuated position.

DETAILED DESCRIPTION OF THE PRESENTLY PREFERRED EMBODIMENTS

Figure 13:
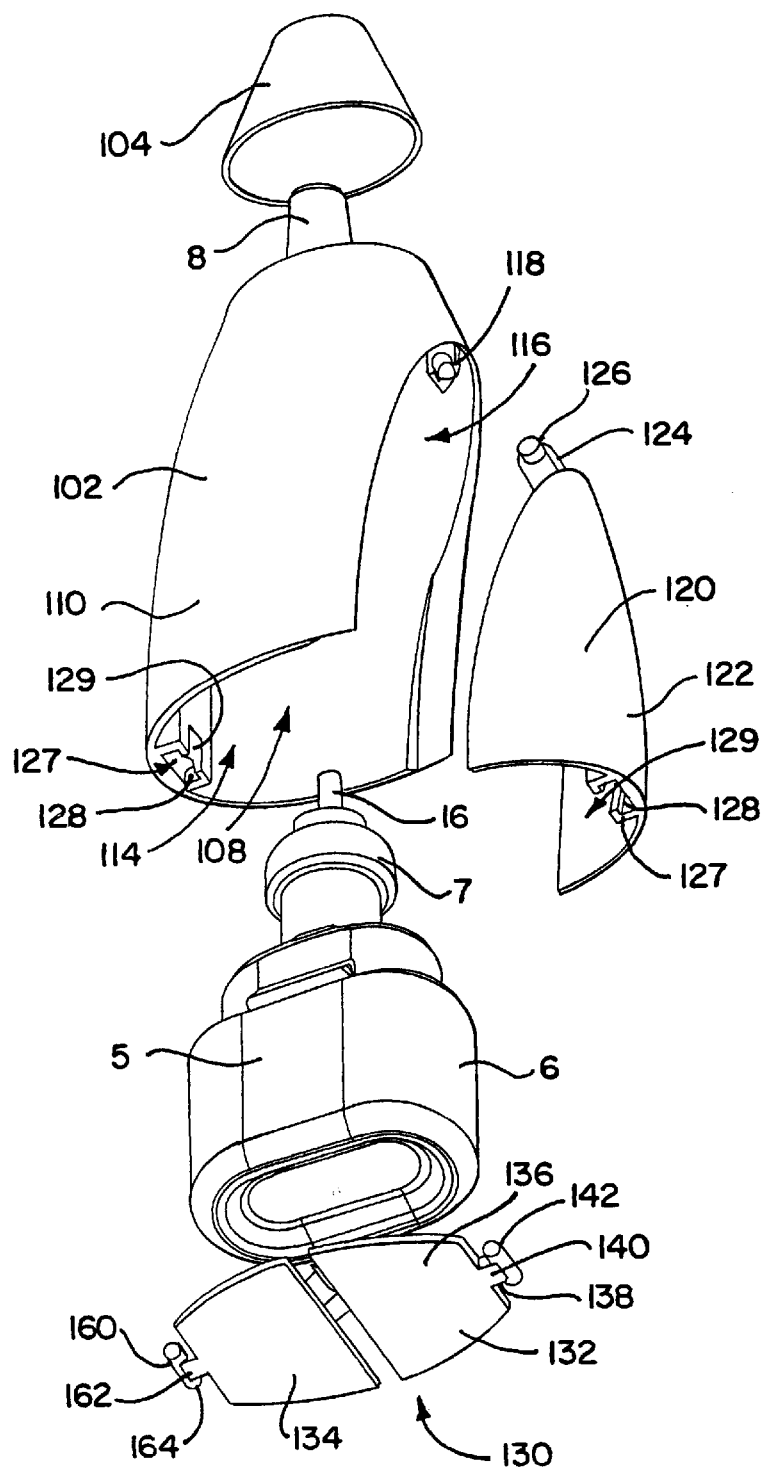
FIG. 13 is an exploded, bottom perspective view of a nasal applicator.

Referring to the drawings, a nasal applicator 2 includes an actuator 4 and a container 5, which includes a holding chamber 6. A nozzle 8 extends longitudinally from the actuator, or in other embodiments from the container 5. In one embodiment, the container 5 includes a pump for creating a pressure for discharging a substance, preferably a medication, stored in the container 5. The term "medicament" as used herein means any substance used in therapy. In one embodiment, the container is actuated by depressing the actuator, which includes the nozzle and a grippable portion 12 or shoulder that the user can grasp with their fingers, relative to the container. One type of nasal sprayer is the Flonase™ nasal spray device available from Glaxo Smithkline. In an alternative embodiment, the container can be made of a relatively flexible material, which can be squeezed to generate a pressure and force the substance through a nozzle connected to the container 5. The term "applicator" as used herein means a device capable of administering the medicament to the user, and includes without limitation nasal sprayers, pressurized metered dose inhalers, and powder inhalers, including without limitation various breath actuated inhalers.

Referring to FIGS. 10–16, one preferred embodiment of an actuator 100 is shown as including a holder 102, a trigger member 120 and a push member 130. The actuator is generally shaped to accommodate the shape of the container that holds the medication. In one embodiment, the actuator 100 is shaped as a portion of an ellipsoid, with smooth, curvilinear walls, and includes a cap 104 that is disposed over the nozzle. The cap preferably fits over and engages an insert portion 106 of the holder with a friction-fit when the device is not in use. The actuator 100, with the cap on, preferably has a height of about 80–120 mm, and more preferably about 100 mm. The length of the major axis along the bottom of the actuator, or the width of the actuator at the bottom, is preferably about 40–70 mm, and more preferably about 58 mm. The length of the minor axis along the bottom of the actuator, or the thickness at the bottom, is preferably about 25–40 mm, and more preferably about 32 mm.

Referring to FIGS. 13–16, the holder 102 forms a cavity 108 and includes a sidewall 110, an upper wall 112 and a generally open bottom 114. A guide 116, forming a passageway or tube, extends downwardly from the upper wall 112 and is shaped to receive and guide an upper portion 7 of the container as the container is moved relative to the holder. The nozzle 8 extends upwardly and outwardly from the upper wall 112 and includes a passageway 14 shaped to receive a stem portion 16 of the container 5. The stem 16 of the container can be moved longitudinally relative to the container 5 to discharge a dosage of substance or medicament, preferably in aerosol form. It should be understood that the medicament can also be discharged in liquid or aerosol form, and that the movement of the stem relative to the container can actuate a pump, or actuate a valve, which releases the medicament from a pressurized container. The stem 16 is preferably inserted into the passageway 14 with a friction fit such that the stem is engaged by the holder 102 and is held in a fixed relationship with respect thereto.

The term "engaged," and variations thereof, broadly means to abut or contact one member with another, and includes without limitation connecting one member to another, whether directly or by way of other intervening members. The terms "connected," "coupled," "mounted," "secured," and "attached," and variations thereof, broadly means that one member is operatively associated with another member, whether directly or by way of one or more intervening members, and includes without limitation members merely contacting or abutting one another as well as members releasably or fixedly joined, for example and without limitation, by mechanical devices such as bonding, molding and fasteners.

The sidewall 110 of the holder can be made transparent, or portions thereof can be made transparent, such that the container or portions thereof are visible from inside the cavity. In this way, various labels or logos displayed on the container are visible to the user. Other labels or logos also can be disposed or applied to the outside surface of the holder.

As used herein the term "longitudinal" refers to the reciprocal movement of the holding chamber portion of the container relative to the stem portion of the container, and the holder engaged therewith. The term "lateral," as used herein, refers to a direction of movement that is not parallel to the longitudinal movement of the container, and preferably a direction that is substantially perpendicular to the longitudinal movement. The terms "top," "bottom," "upper," and "lower" are intended to indicate directions when viewing the applicator as shown in the Figures, but with the understanding that the applicator can be used in any different orientation, including for example and without limitation an inverted position to that shown.

Referring to FIGS. 13–16, one side of the holder 102 is generally open and has a scallop shaped mouth 116, which is shaped to receive at least a portion of the trigger member as it moves relative to the holder. It should be understood that the trigger member alternatively can be configured to move along the outer surface of the holder. The holder 102 includes a pair of aligned C-shaped lug supports, or hinge pockets 118, formed on opposite sides of the holder adjacent a top of the mouth 116. The trigger member 120 has a shell 122 or body that generally mirrors the shape of the opposite side of the holder and further defines the cavity 108 that receives the container. A pivot member 124 extends upwardly from the shell and includes a pair of coaxial hinge pins 126 integrally formed with the pivot member and shell. Alternatively, a hinge pin can be formed as a separate part, which can be inserted through the pivot member. The hinge pins 126 are inserted into the hinge pockets 118 with a snap-fit engagement and define a pivot axis. The term "snap-fit" as used herein means to fit into place with an abrupt movement or sharp sound, typically by temporarily deforming one or the other, or both, of the members being engaged as the members are fitted one relative to the other. In an alternative embodiment, one of the holder and trigger member can include a track or guide that is slideably engaged with a guide member formed on the other of the holder and trigger member such that the trigger member can be translatably moved relative to the holder, rather than being pivoted relative thereto.

The trigger member 120 includes a hinge pocket 128 formed along a bottom edge thereof. The hinge pocket 128 has a pair of coaxially aligned C-shaped sockets 127 opening toward the bottom of the trigger member and a channel 129. A similar hinge pocket 128 is formed along a bottom edge of the holder 102 opposite the trigger member.

The push member 130 preferably includes a plurality (meaning two or more) push members, and preferably a first and second push member 132, 134. It should be understood that the push member can be configured as a single member, or can include three or more members. The first push member 132 includes a wall portion 136 shaped to be received in the generally open bottom 114 of the holder and has a peripheral contour shaped to substantially close a portion of the open bottom The first push member 132 includes a pivot member 138 comprising an arm member 140 and an integrally formed hinge pin 142 disposed on the end of the arm member. The hinge pin can be configured as a separate part in an alternative embodiment. The hinge pin 142 is inserted into the C-shaped sockets 127 in the hinge pocket 128 formed in the trigger member 120 with a snap-fit engagement at a pivot axis 144. In this way, the first push member 132 is pivotally and hingedly connected to the trigger member 120. As the first push member 132 pivots relative to the trigger member 120 about the pivot axis 144, the arm member 140 moves within the channel 129. The first push member 132 further comprises a pair of C-shaped lug members 146, forming hinge pockets, that extend upwardly at an angle from an end thereof opposite the pivot member 138.

The second push member 134 includes a first pivot member 148 extending upwardly at an angle from a wall member 150, which is a substantially mirror image of the first push member wall member 136. The wall members 136, 150 together substantially close the open bottom 114 of the holder. The first pivot member 148 includes a coaxial pair of hinge pins 152 extending laterally from the pivot member and which are inserted into the lug members 146, preferably with a snap-fit, such that the second push member 134 is hingedly, pivotally connected to the first push member 132 at a pivot axis 154. The first pivot member 148 has an upper surface 158 formed thereon.

The second push member 134 includes a second pivot member 160 having an arm member 162 extending laterally outward from the wall member and a hinge pin 164 formed on an end of the arm member. The hinge pin 164 is inserted into the C-shaped sockets, or the hinge pocket 128, formed in the holder with a snap-fit configuration, such that the second push member 134 is hingedly, pivotally mounted to the holder 102 about a pivot axis 166.

As disclosed above, any of the hinge pins described herein can be integrally formed with the various trigger members and push members, or can be formed as separate axles that are captured or otherwise connected to the various parts.

Figure 26:
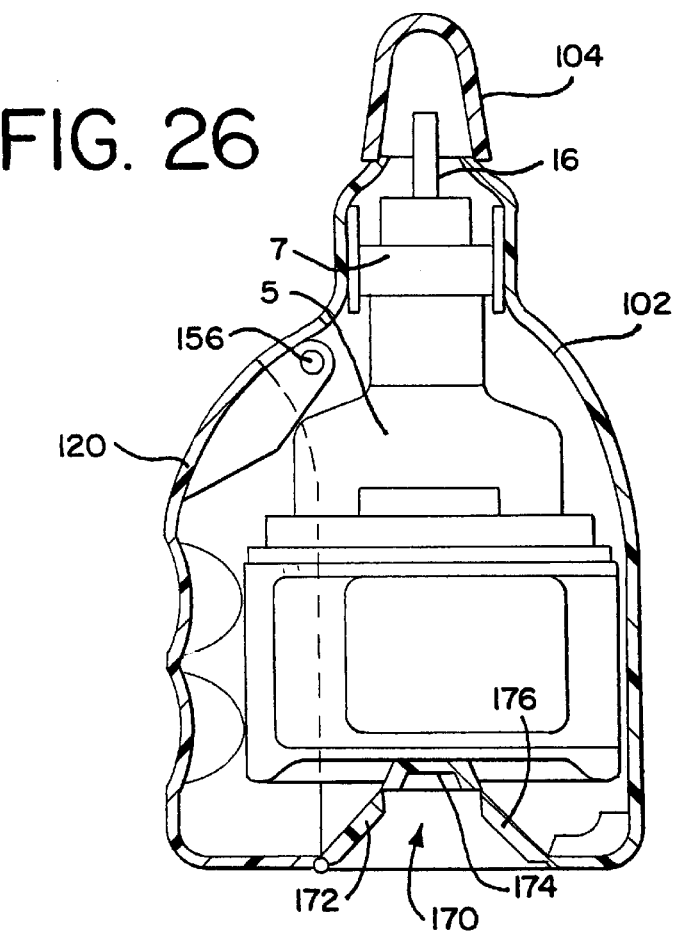
FIG. 26 is a partial front view of an alternative embodiment of a nasal applicator.
Figure 27:
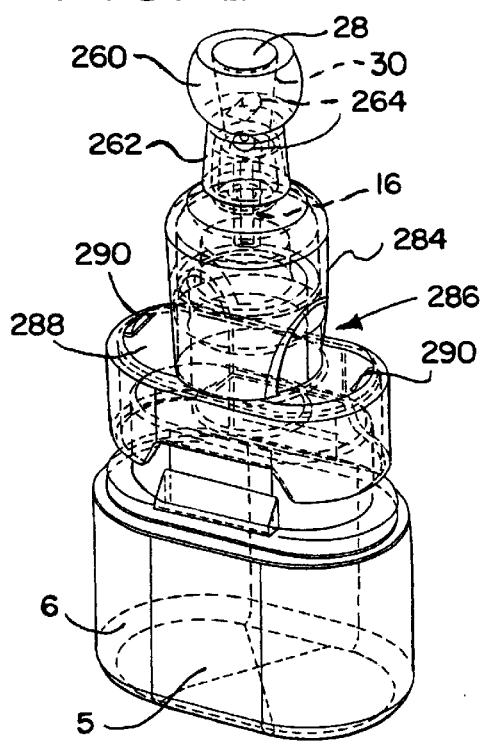
FIG. 27 is a perspective view of an alternative embodiment of a nasal applicator.
Figure 31:
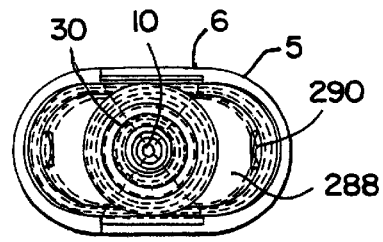
FIG. 31 is a top, plan view of the applicator shown in FIG. 27.
Figure 28:
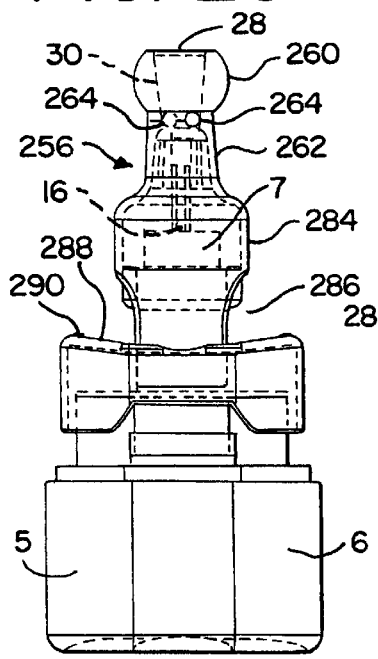
FIG. 28 is a front elevation view of the applicator shown in FIG. 27.
Figure 29:
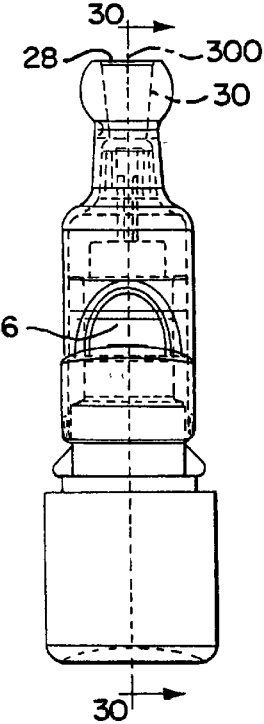
FIG. 29 is a side elevation view of the applicator shown in FIG. 27.
Figure 30:
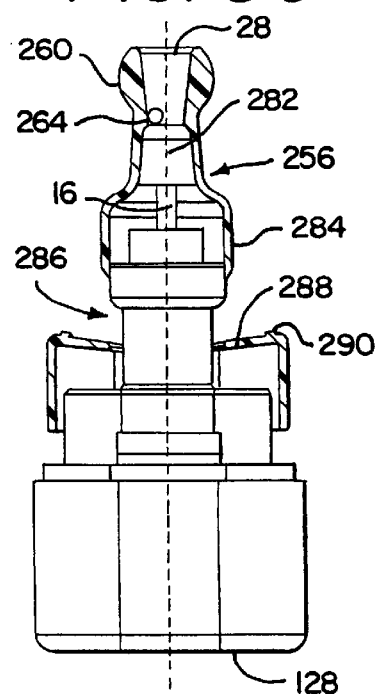
FIG. 30 is a partial cross-sectional view of the applicator taken along line 30—30 in FIG. 29.
Figure 32:
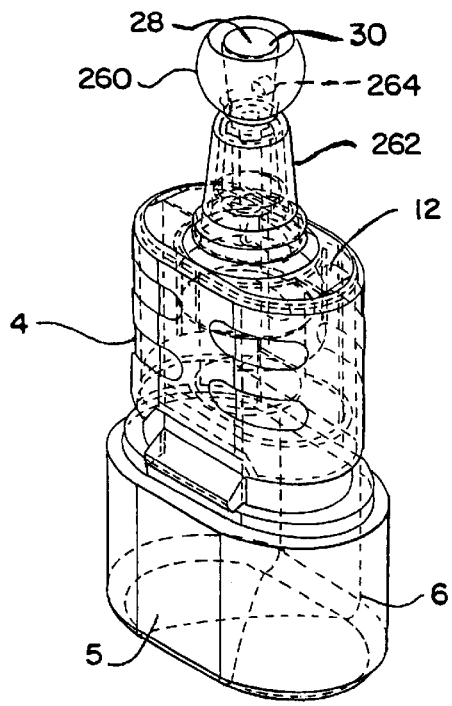
FIG. 32 is a perspective view of an alternative embodiment of a nasal applicator.
Figure 36:
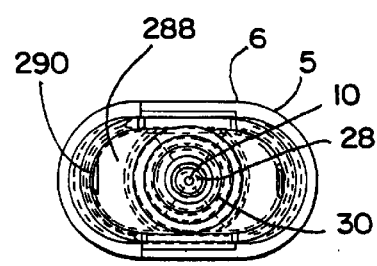
FIG. 36 is a top, plan view of the applicator shown in FIG. 32.
Figure 33:
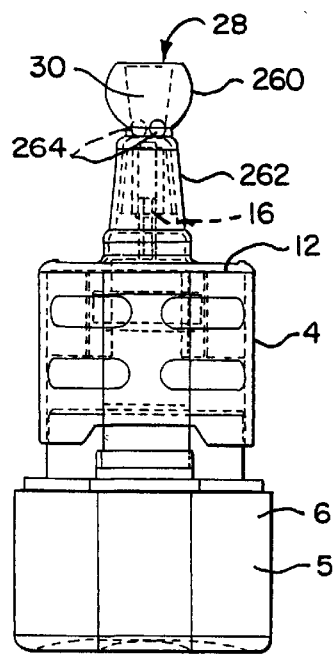
FIG. 33 is a front elevation view of the applicator shown in FIG. 32.
Figure 34:
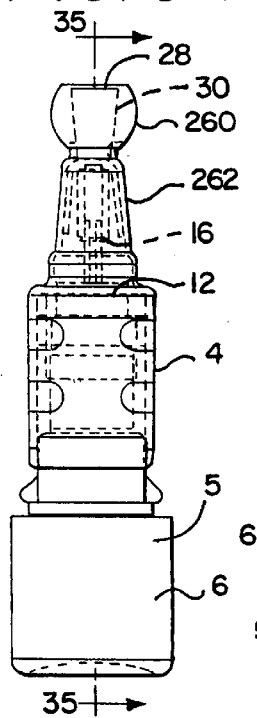
FIG. 34 is a side elevation view of the applicator shown in FIG. 32.
Figure 35:
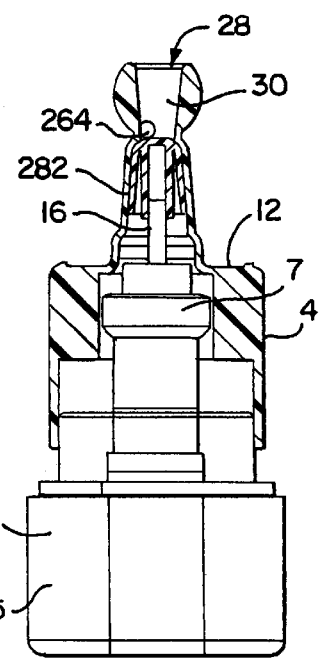
FIG. 35 is a partial cross-sectional view of the applicator taken along line 35—35 in FIG. 34.

It should be understood that in an alternative embodiment, one or more of the trigger, holder and push members are integrally formed as a single, unitary part with the various hinge joints, or pivot axes formed by living hinges, which can be formed by forming a notch, or other thinning of the material, at the juncture between the two hingedly joined members. Alternatively, a flexible material can be used to connect the members being hingedly joined, or a portion of one of the members can be made of a flexible material, such that the flexible material flexes to allow one member to pivot or move relative to the other member. It should be understood that these types of living hinges have virtual pivot axes. For example, as shown in the embodiment of FIG. 26, a push member 170 is integrally formed with the trigger member 120. The push member 170 includes a first push member 170 hingedly joined to the trigger member with a living hinge. Likewise, a second push member 174 is hingedly joined to the first push member 172 and to a third push member 176 with living hinges. The third push member 176 is hingedly joined to the holder.

To assemble the applicator shown in FIGS. 10–16, the container 5 is disposed in the holder 102 with the stem portion 16 engaged by the nozzle 8. The trigger member 130 is then secured to the holder 102 and the push members 132, 134 are secured respectively to the trigger member, to each other and to the holder, such that the holder, trigger member and first and second push members form a four-bar linkage which encloses or encapsulates the container. In this way, the container is not exposed and is protected from damage and/or tampering. It should be understood that the trigger member, holder and push members can be attached to one another before the container is inserted into the holder, with any one of the hinged joints being disengaged such that the push members and/or trigger member can be moved out of the way to allow the insertion of the container into the holder, with the one or more disengaged joints then being reengaged to connect the four-bar linkage. In the preferred snap-fit embodiment, the assembly process is greatly simplified as the total number of parts is reduced. The number of parts can be even further reduced when the parts are integrally formed with living hinges.

Figure 15:
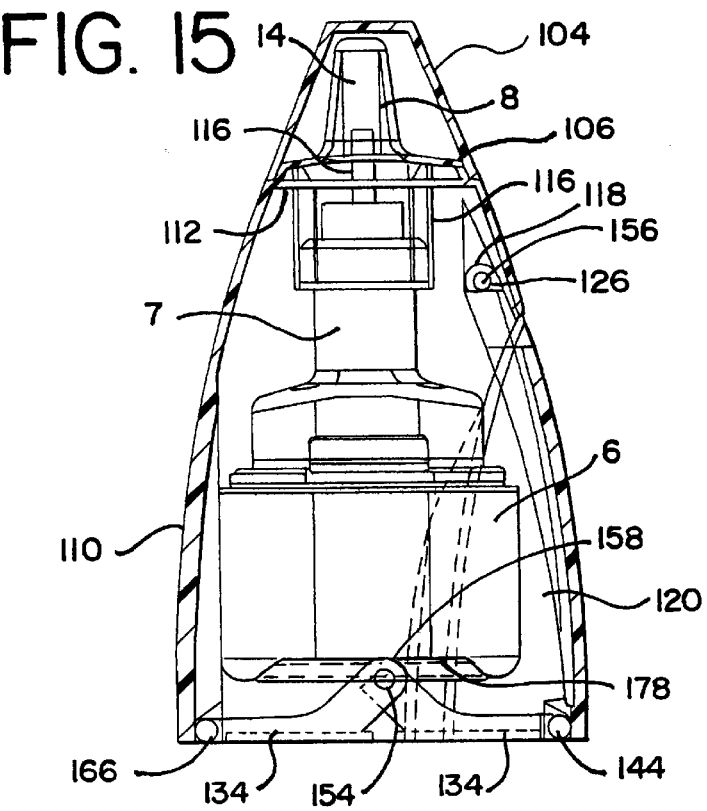
FIG. 15 is a partial cross-sectional front elevation view of a nasal applicator in an un-activated first position.
Figure 16:
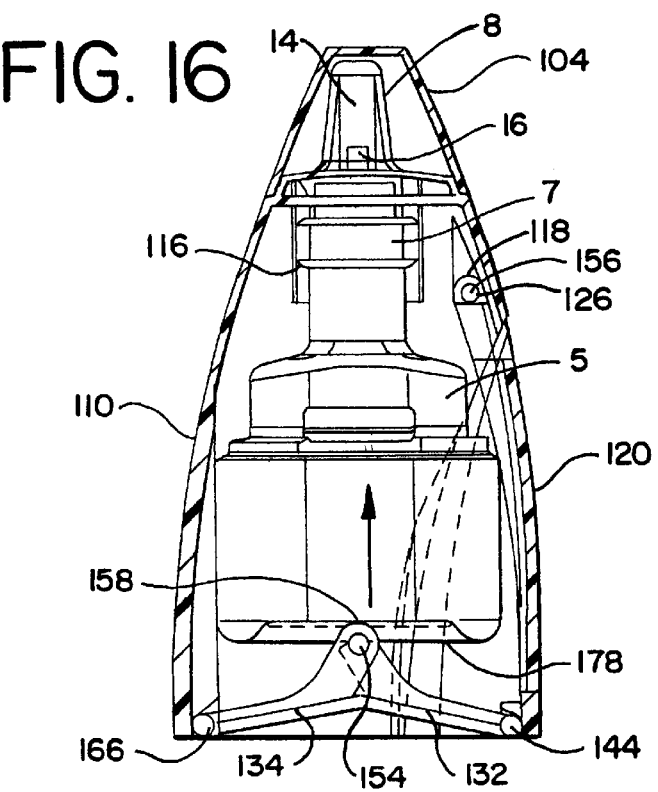
FIG. 16 is a partial cross-sectional front elevation view of a nasal applicator in an activated second position.
Figure 20:
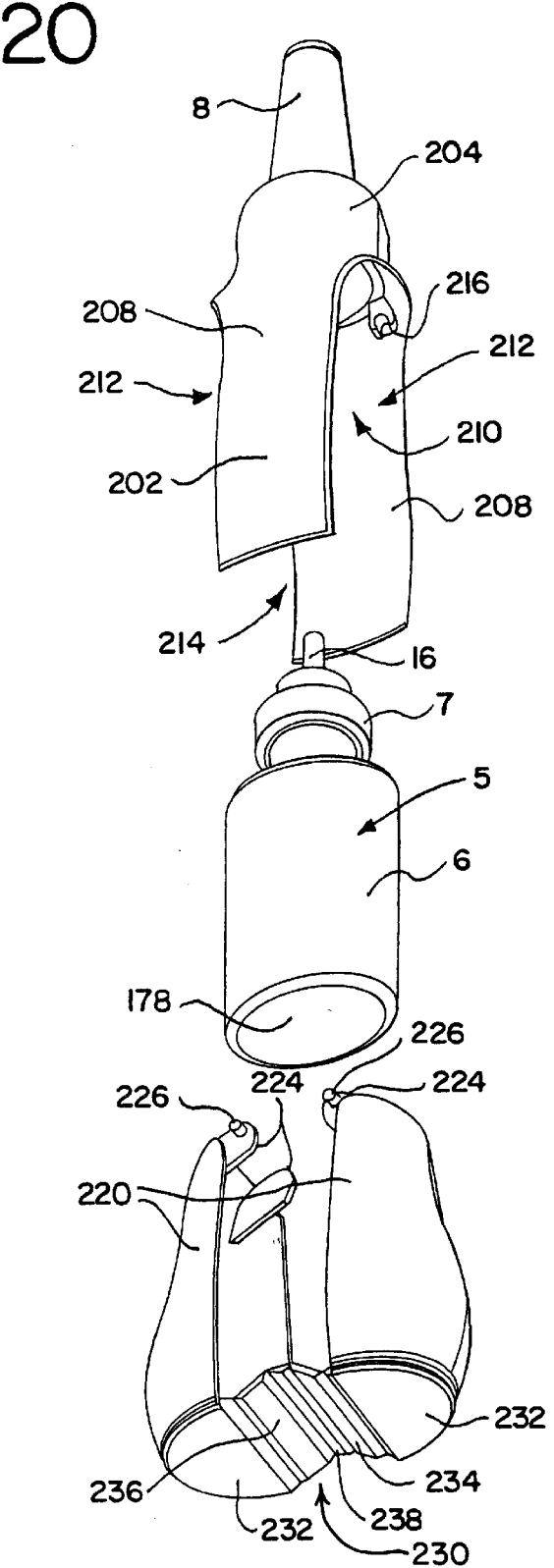
FIG. 20 is an exploded perspective view of a nasal applicator.

In operation, the user inserts the nozzle 8 of the actuator into the nasal cavity and squeezes the trigger member 120 laterally inward from a first, at-rest trigger position to a second, activated trigger position, as the trigger member 120 pivots about the pivot axis 156, as shown in FIGS. 15 and 16. Preferably, the user grips a grippable portion of the holder opposite the trigger member as the user squeezes the trigger member to provide leverage and an opposing force. As the trigger member 120 moves from the first position to the second position as it pivots about the axis 156, it engages and pushes an end of the first push member 132 laterally inward at the pivot axis 144 from a first, substantially flat pusher position to a second pusher position as the first push member pivots upwardly about the axis. It should be understood that the push member can be arranged relative to the container such that it pulls a first portion of the container relative to a second portion thereof, and therefore that the term "push" as used herein broadly means to exert a force thereon, and includes without limitation pulling. At the same time, the first and second push members 132, 134 pivot relative to each other about the pivot axis 154 and the second push member 134 pivots from a first, substantially flat pusher position to a second pusher position about the pivot axis 166. As the inboard ends of the first and second push members 132, 134 move upwardly in a longitudinal direction to the second pusher position, the upper surface 158 of the second push member engages the bottom 178 of the container 5 and pushes the holding chamber upwardly relative to the holder 102 in the longitudinal direction and thereby depresses the valve stem 16 relative to the container 5 and dispenses a dose of medicament from the container. The geometry of the push members and trigger members, and the locations of the various pivot axes, can be configured to accelerate the upward movement of the container relative to the holder.

It should be understood that, for the sake of clarity and simplicity, the same reference numbers have been used to identify various components and/or features common to the various preferred embodiments.

Figure 24:
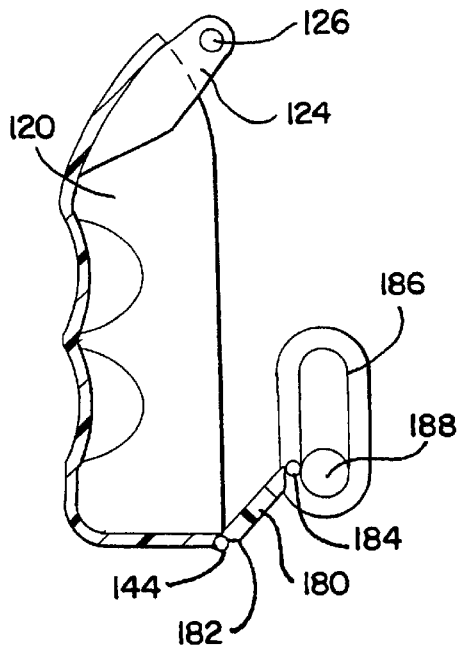
FIG. 24 is a partial front view of an alternative embodiment of an actuator.

Referring to FIG. 24, an alternative embodiment of the actuator is shown as a three-bar slide mechanism. In this embodiment, a push member 180 has a first end 182 hingedly joined to the trigger member and a second end 184 that is slideably connected to the holder. The push member and holder can alternatively be interconnected with a sliding/roller interface. In particular, the holder includes a guide or track 186 that receives a slide member 188 secured to the second end of the push member. As the trigger member is moved from a first trigger position to a second trigger position, preferably in the lateral direction substantially perpendicular to the longitudinal movement of the container relative to the stem, the pusher member pivots about the axis 144 and slide member 188 moves upwardly in the longitudinal direction in the track and pushes the container upwardly relative to the holder and the stem engaged by the holder in the longitudinal direction so as to dispense a dose of medicament. It should be understood that the guide or track could be formed in or on the push member, with the slide member formed in or on the housing.

Figure 25:
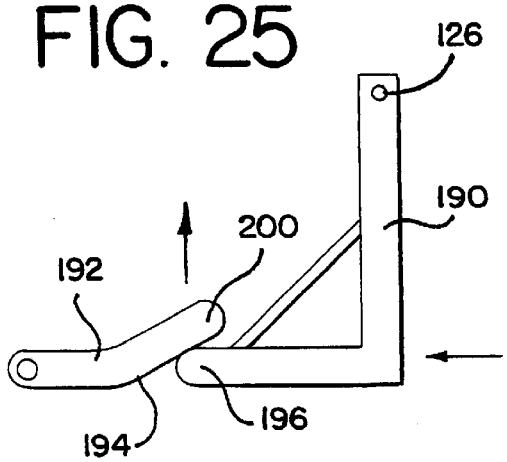
FIG. 25 is a partial front view of an alternative embodiment of an actuator.

In yet another alternative embodiment, shown in FIG. 25, the trigger member 190 abuts or slideably engages a pusher member 192, which includes an angled ramp surface 194 and is pivotally connected to the holder. As the end of the trigger member moves laterally inward, it slides along the ramp surface 194 of the push member and thereby pivots the push member about an axis 198, and moves an end portion 200 of the push member upwardly so as to move the container relative to the holder and to the stem engaged by the holder.

Referring to FIGS. 17–22, yet another alternative embodiment of an actuator 201 is shown. In this embodiment, the holder 202 has an upper portion 204 forming a cavity 206 shaped to receive and guide an upper portion 7 of the container as it moves relative to the holder. A nozzle 8 extends upward from the upper portion 204 and includes a passageway 14 formed therein. A lower portion of the passageway is shaped to receive and engage the container stem 16. The holder 202 further includes a pair of opposite sidewalls 208 extending downward from the upper portion 204 and forming a cavity 210 therebetween. The holder has generally open sides 212 and a generally open bottom 214. A pair of hinge pockets 216 are formed on the inner surface of the sidewalls 208 on each side of the holder. A pair of trigger members 220 each include a shell 222 that further defines the cavity shaped to receive the container. The outer surface of the trigger members 220 is curvilinear and has a contour shaped to conform to the hand of the user. Each trigger member 220 includes a pair of pivot members 224 that extend upwardly and inwardly from the top of the shell. The pivot members 224 each include a hinge pin 226, preferably integrally molded as part of the trigger member. The hinge pins 226 are inserted into the hinge pockets 216, preferably by snap fit, such that the trigger members are pivotally mounted to the holder about spaced apart pivot axes 228, 229.

Figure 21:
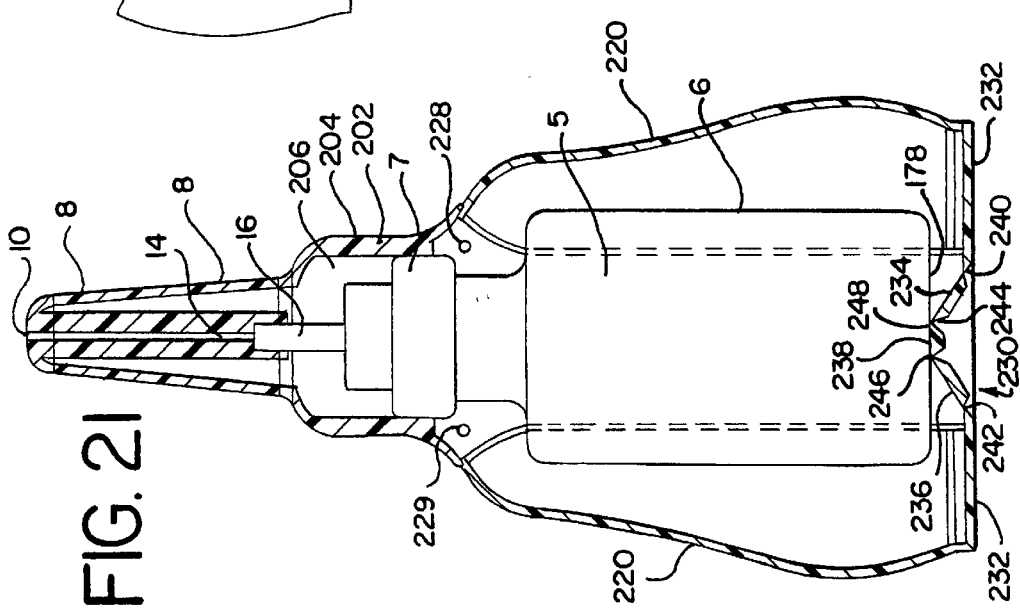
FIG. 21 is a partial cross-sectional front elevation view of a nasal applicator in an un-activated first position.

Each trigger member 220 includes a bottom wall 232 that covers a portion of the generally open bottom 214 of the holder. A push member 230 extends between and connects the bottom walls 232 of the trigger members. Preferably, the push member 230 includes a first, second and third push member 234, 236, 238. The first push member 234 is hingedly connected to the first trigger member 220 at a pivot axis 240, preferably with a living hinge although it should be understood that a hinge pin, whether integrally molded or formed as a separate part, also could be used. Likewise, the second push member 236 is hingedly connected to the second trigger member at a pivot axis 242, and the third push member 238 extends between and is hingedly connected to the opposite ends of the first and second push members at pivot axes 244, 246. In a preferred embodiment, the first and second trigger members 220 and first, second and third push members 234, 236, 238 are integrally formed as a single unit, although it should be understood that they can be formed as separate parts which are thereafter joined by snap fit or otherwise. Preferably, as shown in FIG. 21, the first and second push members 234, 236 are angled slightly upward when the container and actuator are in the at-rest position, with the third push member 238 engaged with the bottom 178 of the container. In this embodiment, the actuator forms a six-bar linkage.

During assembly, the container 5 is disposed in the cavity 210 with the stem 16 engaged by the passageway 14. One or both of the trigger members 220 are then secured to the holder 202 so as to enclose or encapsulate the container within the actuator.

Figure 22:
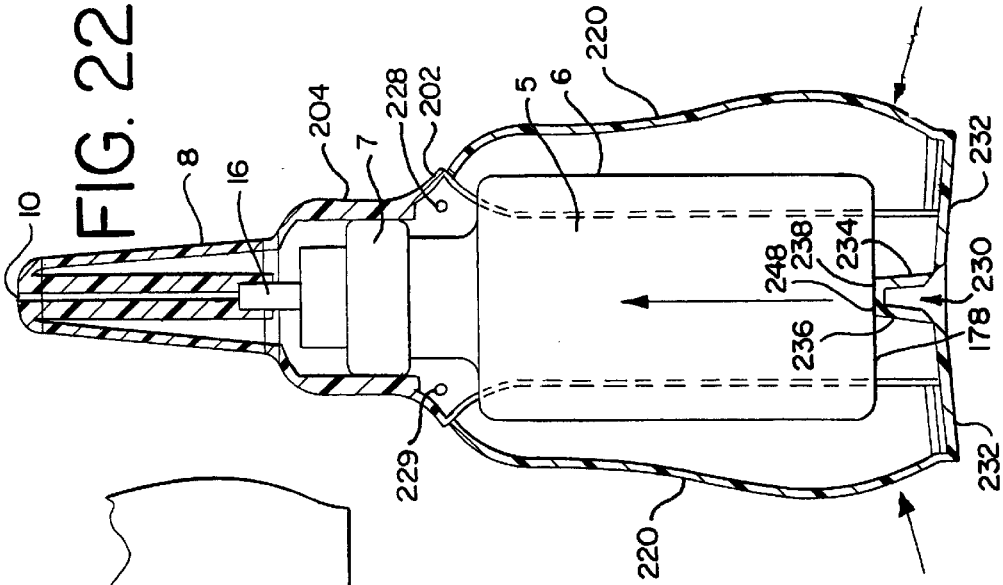
FIG. 22 is a partial cross-sectional front elevation view of a nasal applicator in an activated second position.

In operation, the user inserts the nozzle 8 of the actuator into the nasal cavity and squeezes the trigger members 220 laterally inward from a first, at-rest trigger position to a second trigger position, as the trigger members pivot about the pivot axes 229, 228, as shown in FIGS. 21 and 22. As the trigger members 220 move laterally inward from the first position to the second position as they pivot about the axes 228, 229, the trigger members engage and push the first and second push members 234, 236 laterally inward toward each other at the pivot axes 240, 242 from a first, pusher position to a second pusher position as the first and second push members pivot upwardly about the pivot axes. At the same time, the first and second push members 234, 236 pivot relative to the third push member 238 about the pivot axes 244, 246 and thereby push the third push member in a substantially vertical and longitudinal direction. Preferably, the first and second trigger members 220 and first and second push members 234, 236 are substantially mirror images of each other such that the third push member 238 does not rotate, but rather translates from a first pusher position to a second pusher position relative to the container and holder. As the third push member 238 moves upwardly to the second pusher position, an upper surface 248 of the third push member engages the bottom 178 of the container and pushes the container upwardly relative to the holder and thereby depresses the valve stem relative to the container and dispenses a dose of medicament from the container.

Figure 23:
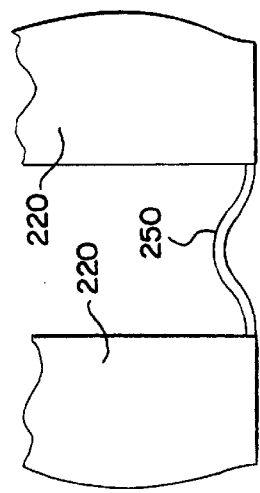
FIG. 23 is a partial front view of an alternative embodiment of an actuator.

In an alternative embodiment, shown in FIG. 23, a push member 250 is formed as a single curved member, preferably having a bell-shaped curve, which extends between and is connected to the bottom walls 232 of the first and second trigger members. Preferably, the push member 250 is not hingedly or pivotally connected to either of the first and second trigger members 220, although it should be understood that it could be so connected. The push member 250 bows upwardly so as to define a concave bottom surface. The push member is preferably made of a flexible material such that it flexes and moves upwardly as the trigger members are pivoted toward each other.

Figure 39:
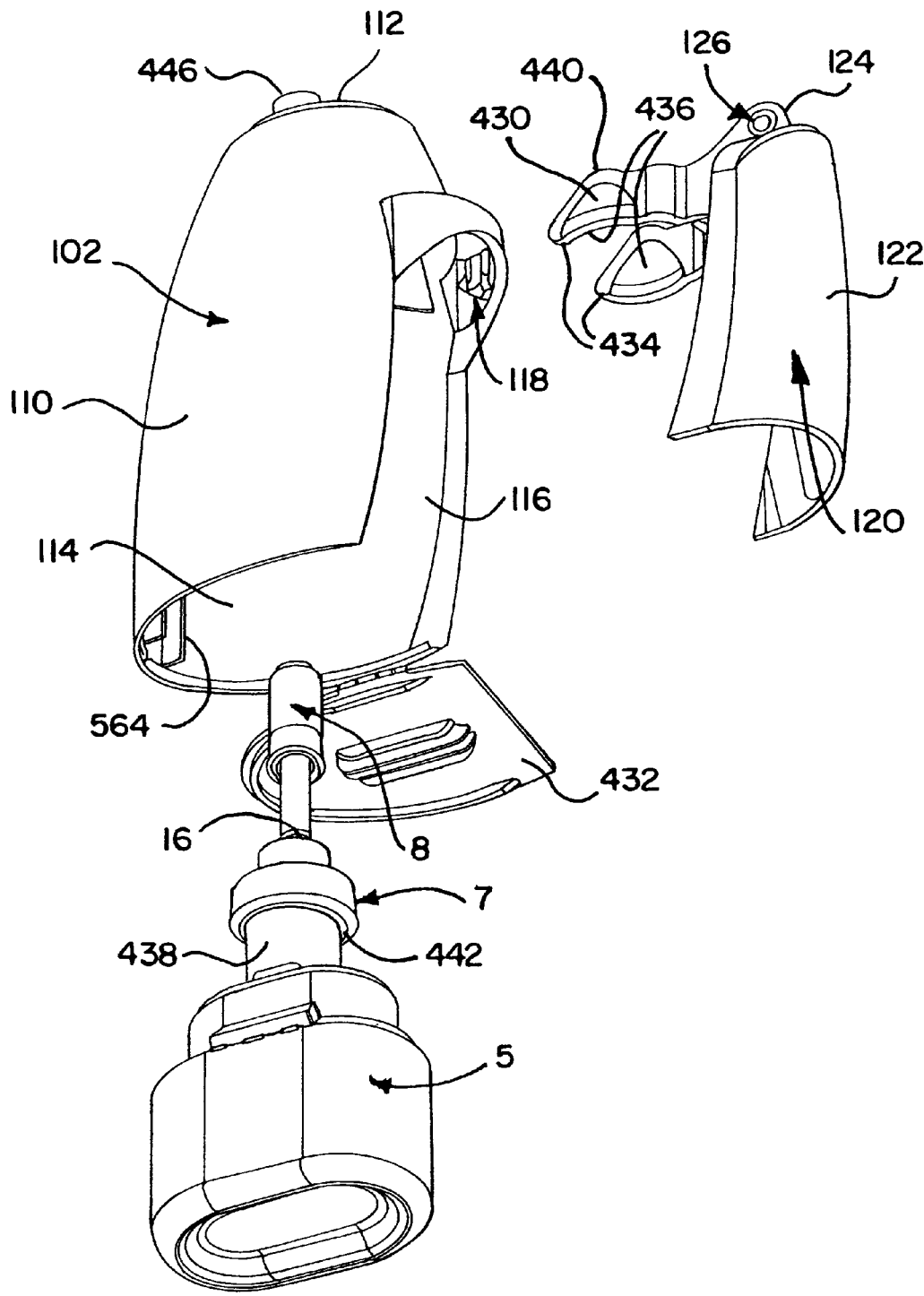
FIG. 39 is an exploded perspective view of the applicator shown in FIG. 38.
Figure 41:
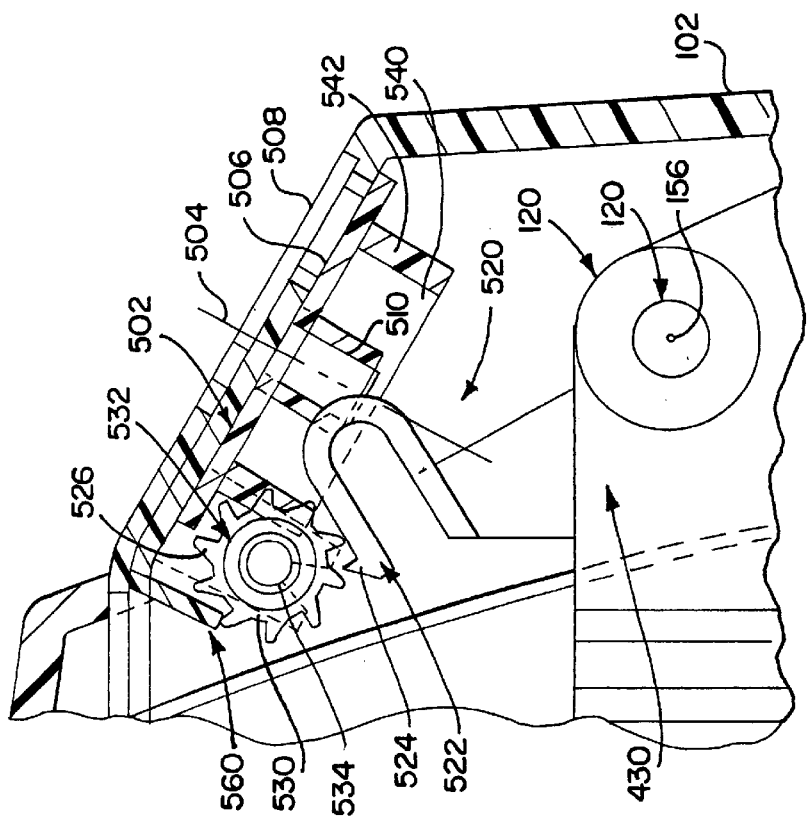
FIG. 41 is a partial exploded view of the nasal applicator shown in FIG. 40.
Figure 40:
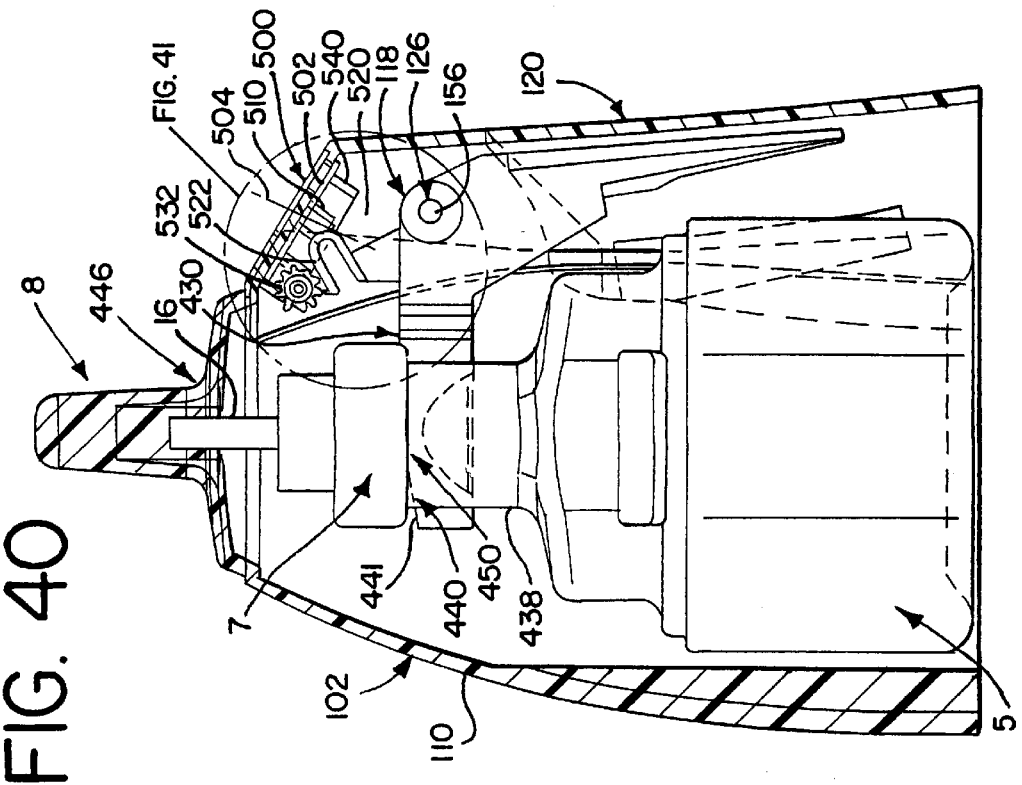
FIG. 40 is a front elevation view of an alternative embodiment of a nasal applicator.
Figure 42:
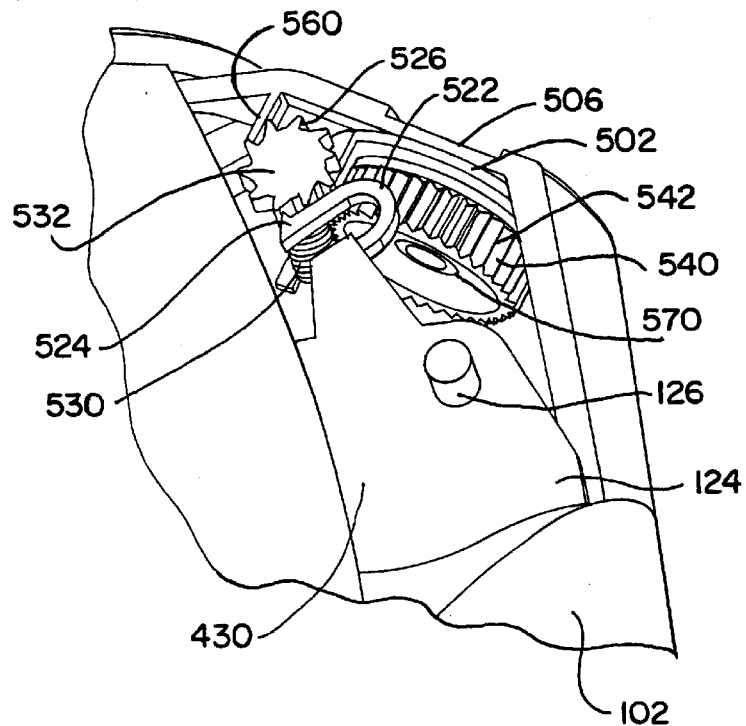
FIG. 42 is a partial perspective view of an actuator having an indicator mechanism, with the portions of the actuator being cut away, and with a trigger member in an at-rest position.
Figure 43:
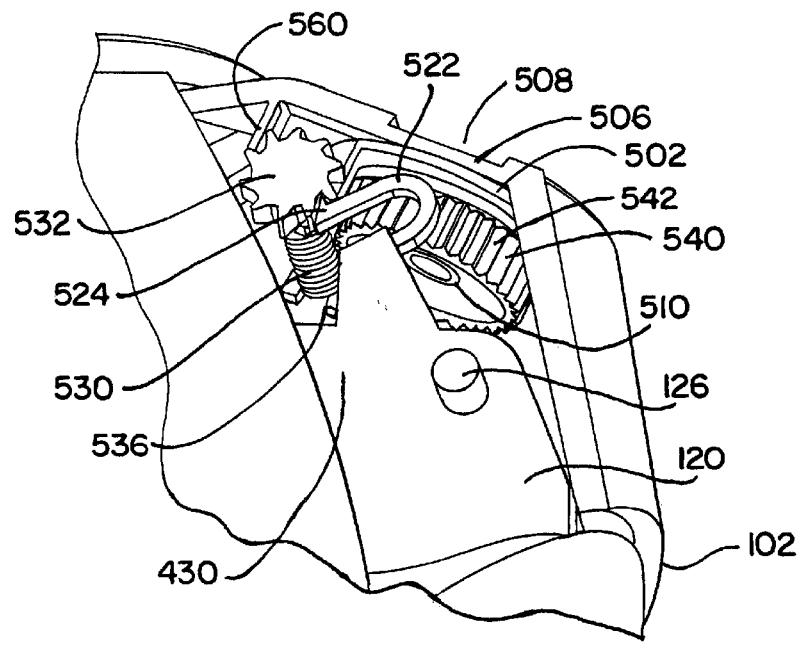
FIG. 43 is a partial perspective view of an actuator having an indicator mechanism, with the portions of the actuator being cut away, and with a trigger member in an activated position.
Figure 44:
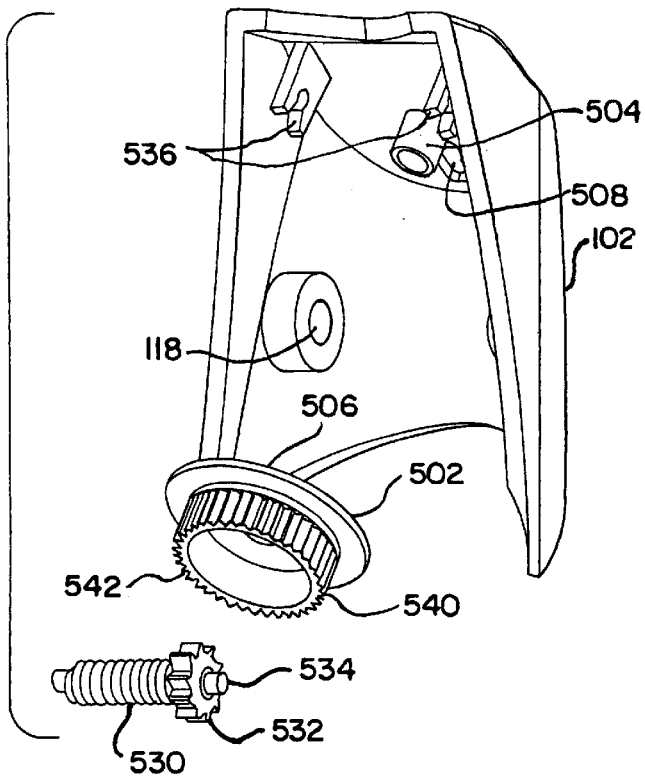
FIG. 44 is an exploded view of one preferred embodiment of the indicator mechanism.
Figure 45:
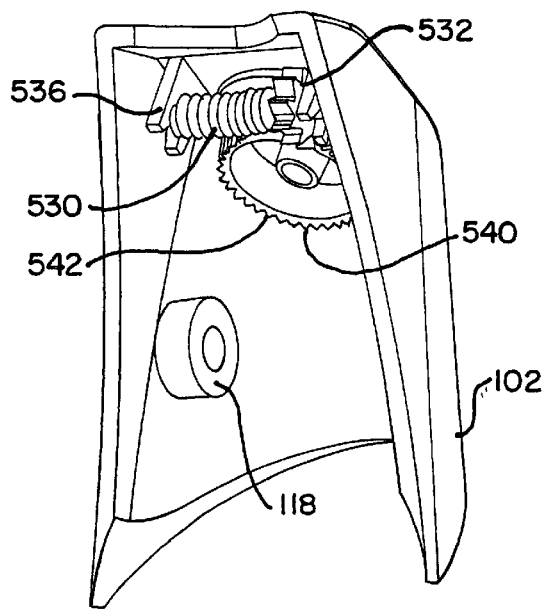
FIG. 45 is an interior perspective view of the indicator mechanism.
Figure 46:
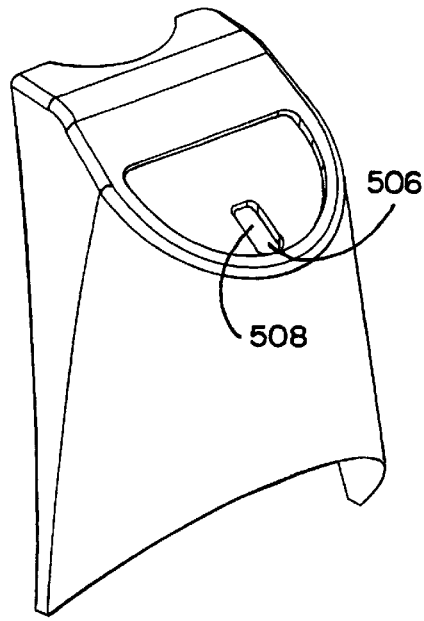
FIG. 46 is an exterior perspective view of a portion of a holder with a view window formed therein.
Figure 47:
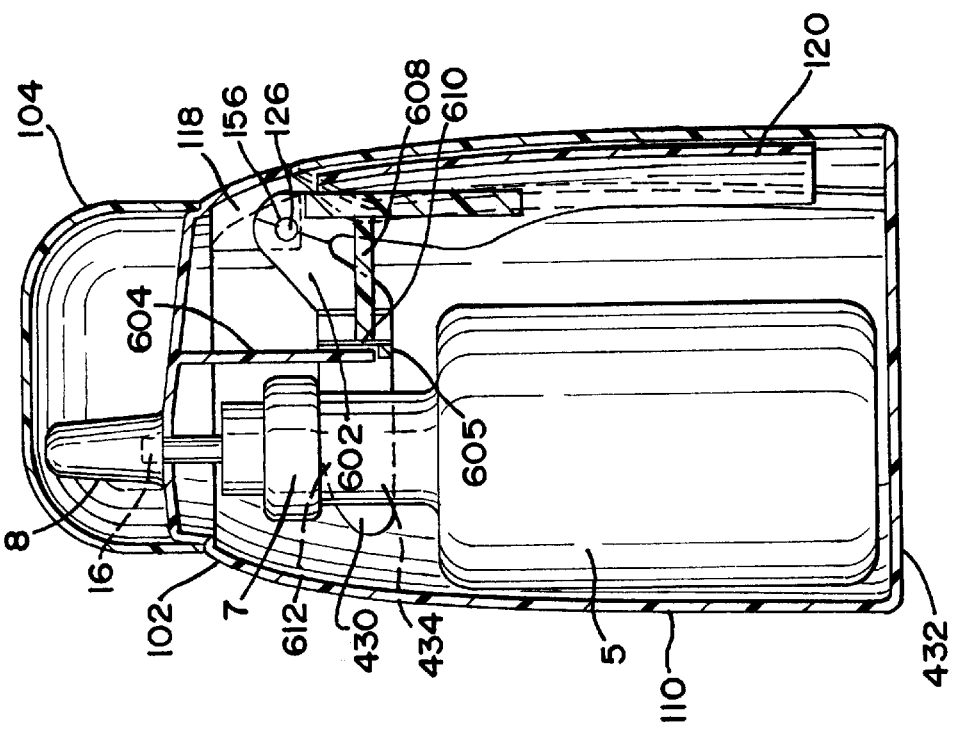
FIG. 47 is a front elevation view of an alternative embodiment of a nasal applicator.
Figure 64:
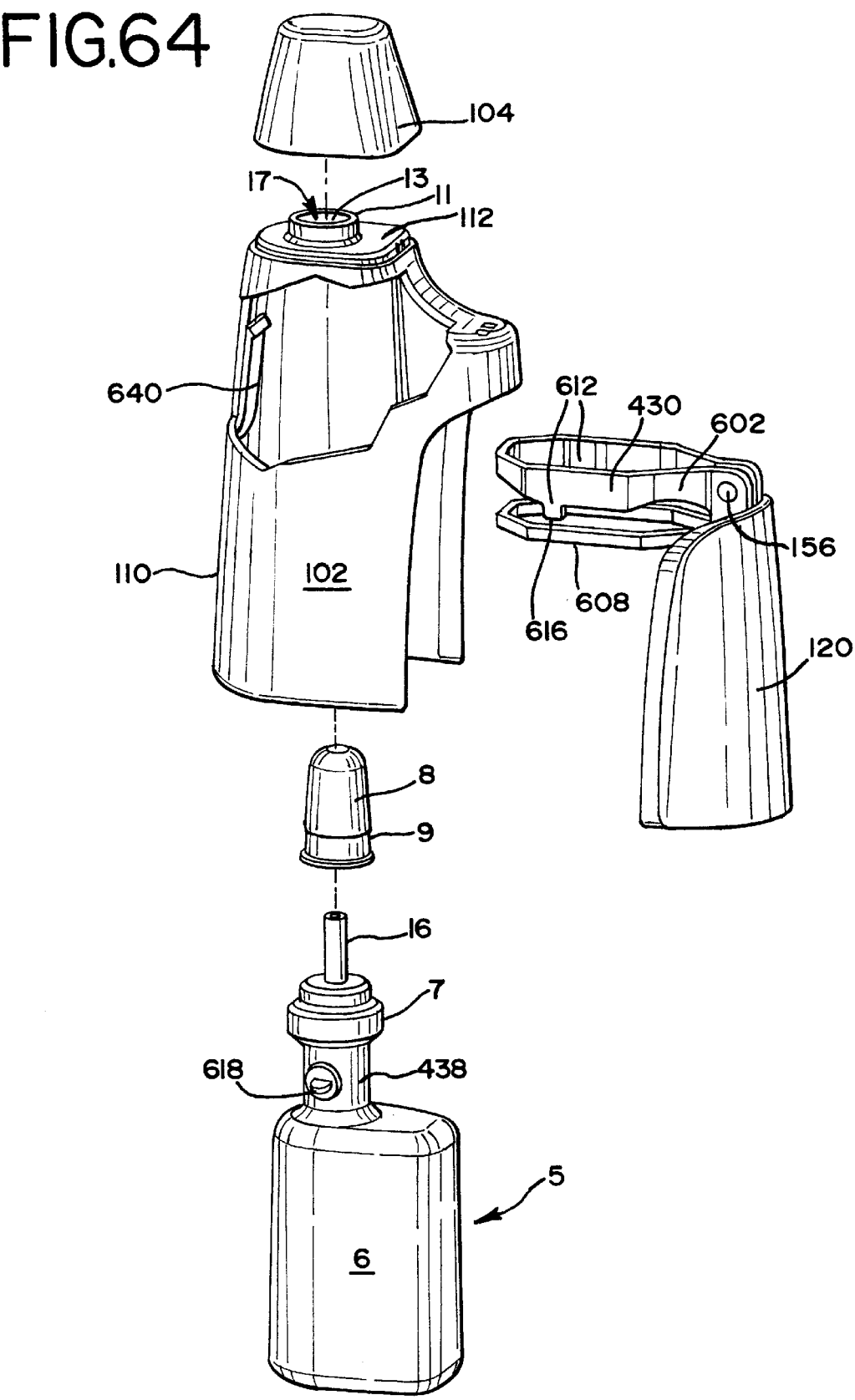
FIG. 64 is an exploded perspective view of the applicator shown in FIG. 52.

In yet another alternative embodiment of the actuator, shown in FIGS. 38–40, a push member 430 is connected to, or extends from, the trigger member 120, and the pivot member 124 in particular. As explained above, the push member 430 can be formed integrally with the trigger member 120, or can be secured thereto as a separate part. The push member 430 includes a pair of resilient arms 434 that extend laterally inward into the cavity. The arms are spaced apart, with a dimension suited to receive a neck portion 438 of the container 5. Alternatively, as shown in FIGS. 63 and 64, the push member 430 is formed as a loop member that surrounds the container. Referring to FIGS. 38–40, preferably, an inner surface 436 of each arm 434 is curved or rounded to mate with, or partially encapsulate, the outer surface of the neck. Preferably, the resilient arms 434, which are biased around the neck portion, each have an engagement portion defining a contact surface 440 formed along an upper surface thereof that engages a bottom surface 442 of an upper collar portion 7 of the container. The contact surface 440 can be contoured, so as to function like a cam, such that the collar 7 is moved more or less in the vertical direction as the push member 430 pivots about the pivot axis 156. Preferably, the surface 440 is contoured such that ratio of the vertical displacement of the collar 7 relative to the angular rotation of the push member 430 is reduced as the push member 430 pivots inwardly about the pivot axis 156. Preferably, at least a portion of the contact surface 440 is concave. At rest, the push member 430 contacts the collar 7 at point 450, however the contact point moves to point 441 in the full activated position. The concave shape of the end of the push member 430 reduces the shear force against the collar 7 so that the collar is not pulled sideways while being pushed upward.

The container 5 is enclosed in the holder 102, which includes a bottom 432 that is secured to the sidewall 110 thereof The bottom 432 can be integrally formed with, such as by molding, and/or hingedly connected to the sidewall 110. A lock device, such as a snap fit, can be used to secure the bottom in a closed position. Alternatively, the bottom can be made separate from the side wall and can be secured thereto by snap fit, or by a hinged connection. The nozzle 8 also can be integrally formed as part of the holder. Alternatively, the nozzle 8 can be made as a separate part that is installed on an upper collar or insert portion 446 of the holder, e.g., by snap fit or press fit.

Figure 65:
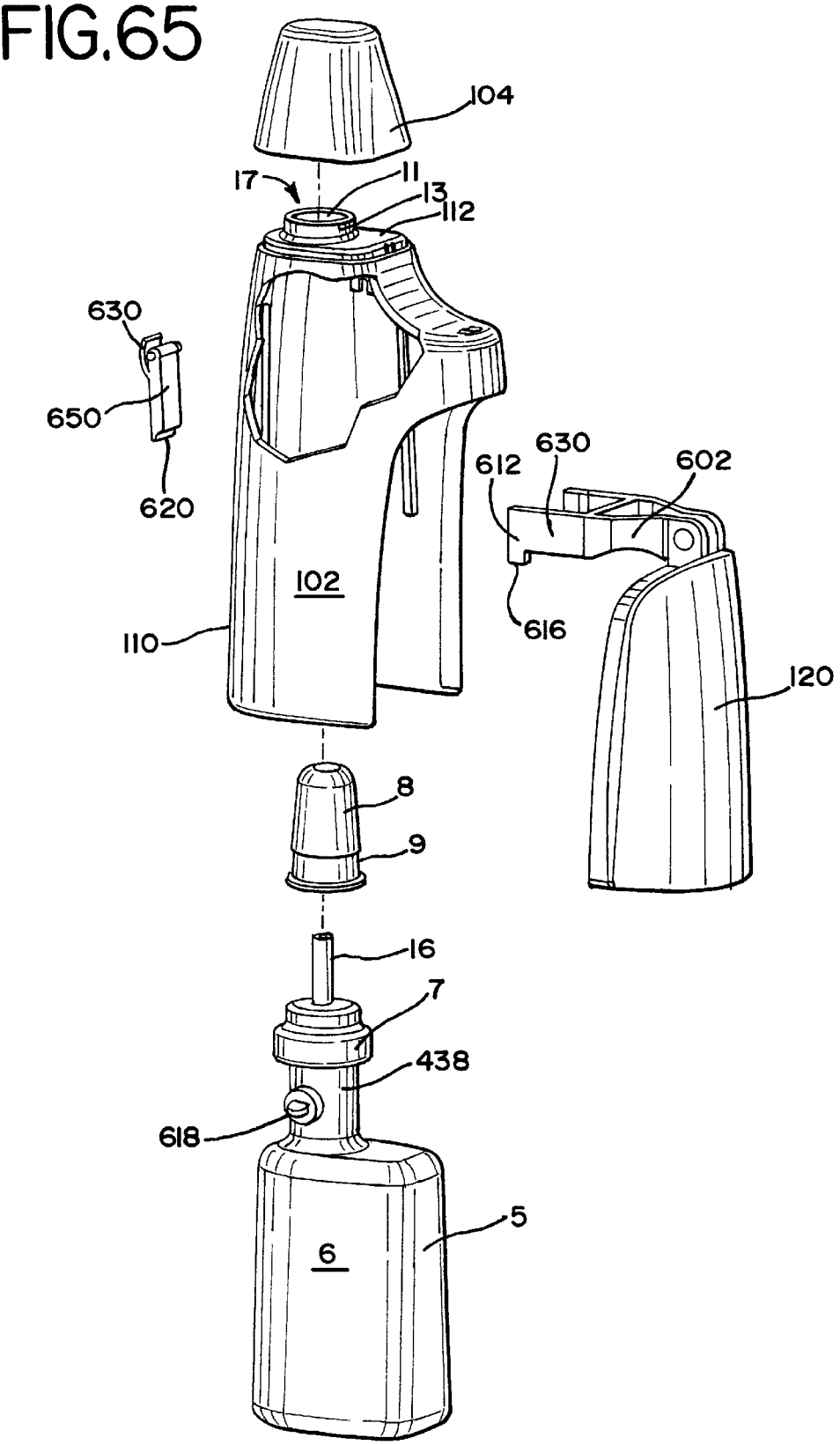
FIG. 65 is an exploded perspective view of an alternative embodiment of an applicator.
Figure 74:
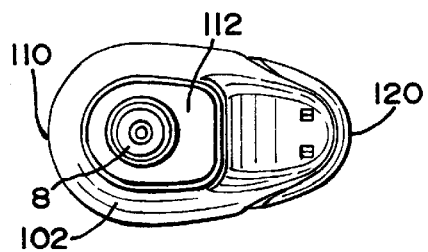
FIG. 74 is a top view of the applicator shown in FIG. 75.
Figure 75:
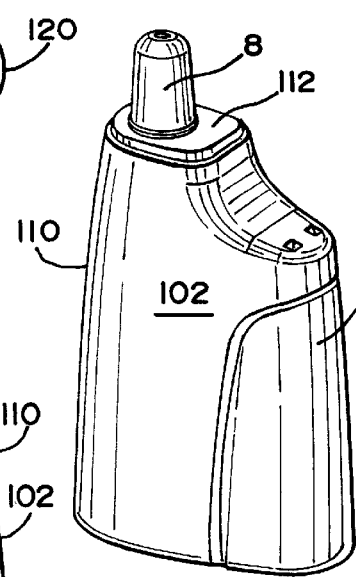
FIG. 75 is a perspective view of the applicator shown in FIG. 66 with the cap removed therefrom.
Figure 76:
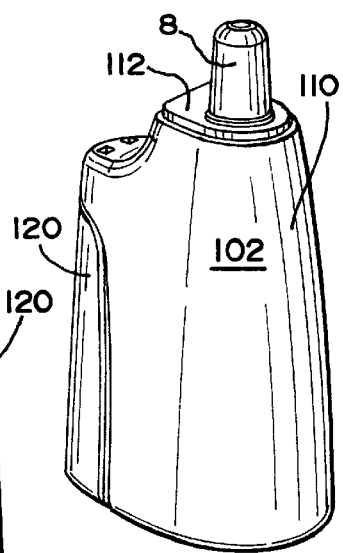
FIG. 76 is an opposite perspective view of the applicator shown in FIG. 75.
Figure 77:
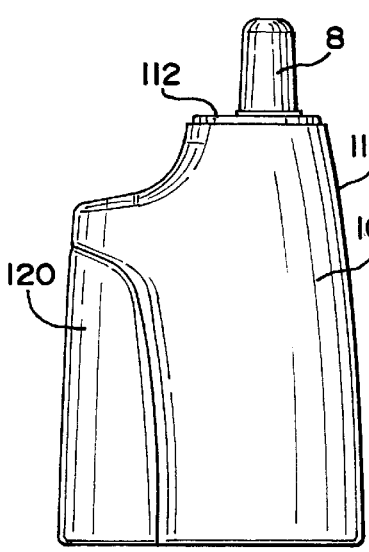
FIG. 77 is a rear view of the applicator shown in FIG. 75.
Figure 78:
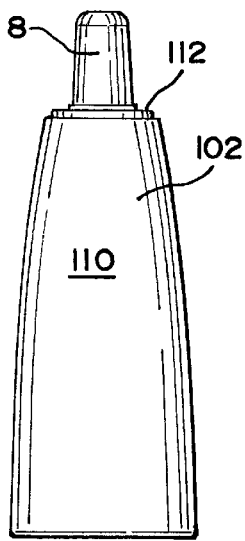
FIG. 78 is a left side view of the applicator shown in FIG. 75.
Figure 79:
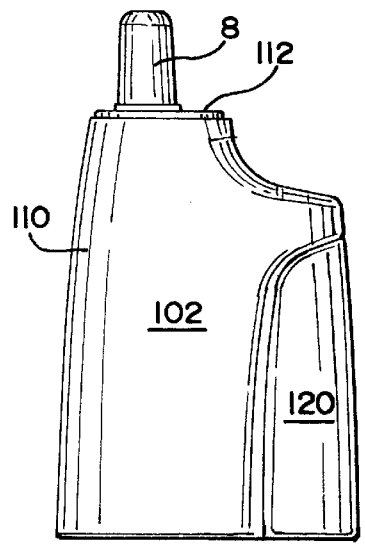
FIG. 79 is a front view of the applicator shown in FIG. 75.
Figure 80:
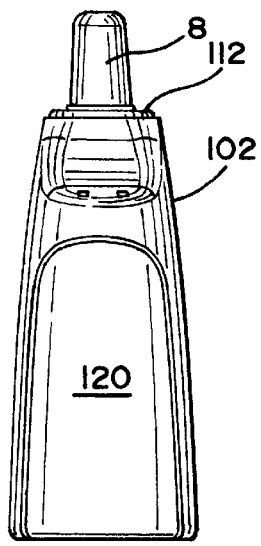
FIG. 80 is a right side view of the applicator shown in FIG. 75.

For example and referring to FIGS. 63–65, as shown in one preferred embodiment, the nozzle 8 can be inserted upwardly through an opening 17 formed in the upper wall 112. The nozzle preferably has an annular recess 9 formed around a lower periphery thereof that is engaged by an annular flange 11 extending upwardly from the wall. The flange preferably has one or more slits 13, which allow it to flex outwardly as the nozzle 8 is inserted through the opening 17 in the upper wall and then snap into place in the annular recess. With this configuration, different sizes and types of nozzles and diffusers can be used on the applicator to accommodate different users and applications.

In one preferred embodiment, the holder 102 includes a plurality of ribs 564, that act as guides and support the side of the container holding chamber as it moves longitudinally relative to the holder.

In operation, the user inserts the nozzle 8 of the actuator into the nasal cavity and squeezes the trigger member 120 laterally inward in a first rotational direction from a first, at-rest position about the pivot axis. Preferably, the user grips the holder 102, which has a grippable side wall portion 110, on an opposite side of the trigger member 120. As the trigger member 120 moves laterally, inwardly in the first direction toward the opposite, grippable side wall 110, the push member 430, which is connected to the trigger member 120, is moved or pivoted with the trigger member 120 in the first rotational direction about the pivot axis 156, preferably with a portion thereof being moved in the longitudinal direction due to the rotational spacing between the trigger member and the push member. In this way, the trigger member 120, and the push member 430, which is an extension of the trigger member, both move in an arc path about the pivot axis 156, but with portions thereof moving substantially perpendicular to each other. Since the trigger member 120, and in particular a length of the trigger member 120 between a bottom thereof and the pivot axis 156, is preferably longer than the length of the push member 430, and in particular longer than the distance between a contact point 450 and the pivot axis 156, a greater force can be applied to the container 5 by way of the mechanical advantage realized by the lever ratios. Preferably the ratio between the length of trigger member 120 (measured from the pivot axis 156 to the bottom end of trigger member 120) and the length from the pivot axis 156 to the contact point 450 is 2:1.

As the push member 430 pivots about the pivot axis 156, the contact surface 440 moves the container collar 7, neck 438 and holding chamber relative to the stem portion 16 in the longitudinal direction, with the stem portion being engaged by the nozzle at passageway 14 or by another portion of the holder. By moving the collar 7 relative to the stem portion 16, a pump or valve is actuated to dispense a dose of medicament. In one preferred embodiment, compression of the pump forces liquid medication from the container into the nozzle, the geometry of which preferably forms an aerosol as it exits the nozzle. As the internal travel of the pump, e.g., the collar moving relative to the stem, is reached, the motion stops.

The user can then relax the trigger member 120. An internal spring force of the container 5 acts on the push member 430, by way of the collar 7, so as to move the push member 430 and trigger member 120 from the actuated position in a second direction opposite the first direction as they pivot about the pivot axis 156 to the at-rest position. In this way, a simple two-piece mechanism having a holder and trigger/push member can be used to dispense a medicament from the container, which reduces the cost and improves the reliability of the actuator. In addition, the mechanical advantage of the trigger member allows the user to actuate the actuator with less force than many conventional devices.

Referring to FIGS. 47–51, another alternative embodiment of an actuator is shown as having a spring 602 disposed or coupled between the push member 430 and the trigger member 120. In one preferred embodiment, the spring 602 is formed integrally with the push member 430 and trigger member 120 and is configured as a U-shaped member. Alternatively, the push member and trigger member can be made separately, with a coil spring or torsion spring coupled between the members. A stop member 604 extends from the housing and engages the push member 430, and in particular, a stop portion 605, formed as a tab, disposed thereon. The stop member 604 preferably protrudes or extends from the housing and has one end fixedly attached thereto. Preferably, the stop member 604 is flexible or resilient, such that it can bend or flex. In one alternative embodiment, the stop member engages the container, for example, the collar or shoulder portion thereof, rather than the push member. A trip member 608 extends laterally inward from the trigger member 120 and has an end portion 610 initially spaced from the stop member. In one preferred embodiment, shown in FIGS. 63 and 64, the trip member 608 is formed as a loop member that surrounds the container as it is inserted through the loop.

In an alternative embodiment, the trip member is moveably mounted to the housing, and can be actuated independently of the trigger member. Preferably, the trip member is spring loaded such that it returns to an at-rest disengaged position.

Figure 48:
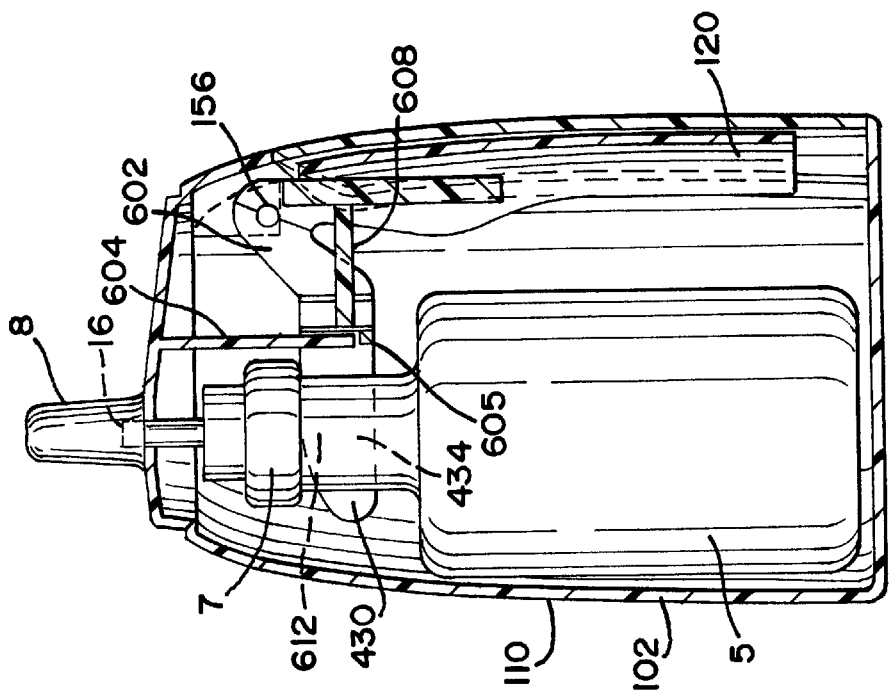
FIG. 48 is a front view of the nasal applicator shown in FIG. 47 in a normal, at-rest position.

Referring to FIGS. 48–51, in operation, the trigger member 120 is moved laterally inward along a path, as it is pivoted about the pivot axis 156 in the first rotational direction from the at-rest position, as shown in FIG. 48. During this sequence, the stop member 604 is engaged with the push member 430 and prevents the push member 430 from pivoting about the pivot axis 156, thereby immobilizing the push member, and in particular the engagement portion 612 thereof. In an alternative embodiment, the stop member engages the container, and thereby immobilizes the push member by way of the container.

Figure 49:
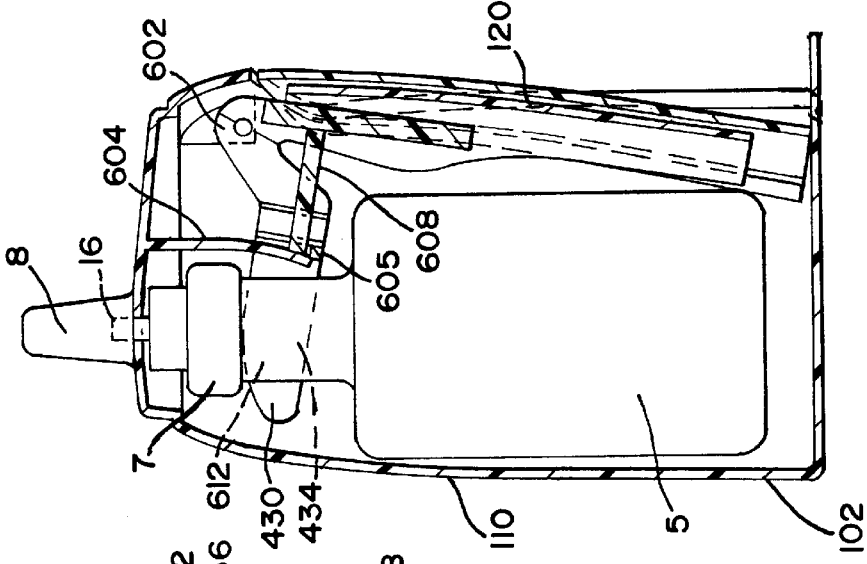
FIG. 49 is a front view of the nasal application shown in FIG. 47 during a predetermined portion of the path of the trigger member with a stop member immobilizing the push member.
Figure 50:
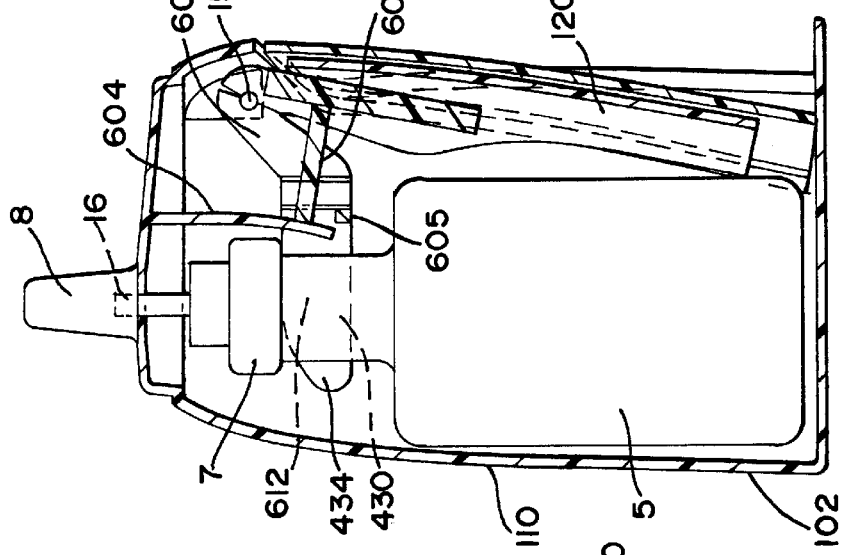
FIG. 50 is a front view of the nasal applicator shown in FIG. 47 as the trip member disengages the stop member from the push member.
Figure 51:
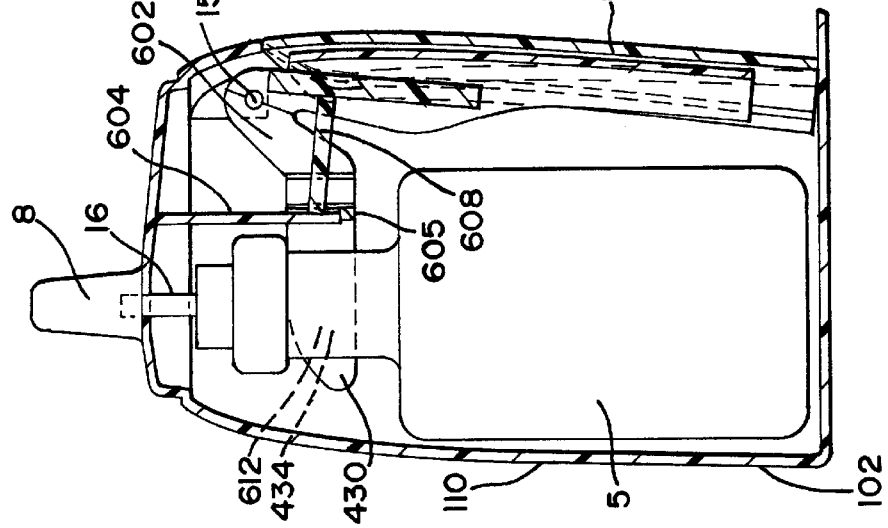
FIG. 51 is a front view of the nasal applicator shown in FIG. 47 as the push member actuates the container.

Referring to FIGS. 49 and 50, after the trigger member 120 has moved along a predetermined portion of its path of travel, the trip member 608 is engaged with the stop member 604. Alternatively, the user can separately actuate a trip member, which is moveably mounted to the housing, by moving it from a disengaged to an engaged position once the trigger is fully depressed. In either case, while the trigger member is being moved along the predetermined path, the spring 602 is loaded, as energy is stored therein by way of the trigger member 120 being moved toward the push member 430. Preferably, the energy stored in the spring 60 as the trigger member 120 completes the predetermined portion of its path exceeds the energy or force required to actuate the container 5. Referring to FIG. 50, as the trigger member 120 completes the predetermined portion of the path, the trip member 608 engages the stop member 604 and disengages the end of the stop member from the push member, and in particular the stop portion 605, or container, and bends or flexes the stop member 604 into a disengaged position. At this point, the stored energy in the spring 602 pivots the engagement portion 612 of the push member about the pivot axis 156 in the first rotational direction, thereby moving the engagement portion in the longitudinal direction so as to actuate the container. In particular, the engagement portion moves in the longitudinal direction and thereby moves the collar 7 and holding chamber of the container towards the stem portion 116 thereof so as to dispense the medication. It should be understood that the predetermined portion of the path can be the entire path of travel of the trigger member, such that the trip member disengages the stop member as the trigger member is pivoted a maximum amount, although preferably, the predetermined portion is less than the full path of the trigger member, and is defined as that portion of the path traveled by the trigger member from the initial, at-rest position to the position where the stop member is disengaged from the push member or container.

It should be understood that a reference to the push member being pivotable about the pivot axis in the first and second directions as the trigger member is pivoted in the first and second directions respectively means that the push member pivots in the first direction and second directions about the axis either (1) simultaneously with at least a portion of the pivoting motion of the trigger member in the first and second directions respectively, or (2) subsequent thereto, for example, when a stop member is used to immobilize the push member during at least a portion of pivoting motion of the trigger member in the first direction.

After the medication has been dispensed, the user releases the trigger member 120, and the internal spring of the container 5 moves the collar 7 and holding chamber of the container away from the stem 16 and thereby moves the push member 430 and trigger member 120 to the normal, at-rest position. At the same time, the stop member 604 moves from the disengaged position to the engaged position, wherein the stop member is again positioned to immobilize the push member, whether directly or by way of the container.

In this way, the actuator is not actuated unless a predetermined amount of energy has been stored in the spring 602, which assures that enough energy is stored to fully actuate and dispense a dose of medication from the container. Accordingly, a controlled, consistent actuation is provided, which ensures a predictable dispersal of medication and increases the likelihood that the user will receive the proper dosage of medication. In addition, the stop member reduces the likelihood that the actuator and container will be accidentally discharged, for example, by incidental contact with the trigger.

Various alternative preferred embodiments of the actuator are shown in FIGS. 52–54 and 63–80, each of which includes a spring 602 formed as a flexible area coupled between the push member 430 and the trigger member 120. In addition, the engagement portion of the push member, formed as a pair of arms 434, includes a pair of tabs 616 defining the contact surface, which rests under and engages a pair of tabs 618 formed, preferably by molding, on the neck 438 of the container 5.

Referring to FIG. 54, a stop member 620 is pivotally mounted to the housing about a pivot axis 622. The stop member 620 includes a pivot member 624 that is snap-fitted into sockets formed in the housing. It should be understood that the pivot member can be made as a separate part, or that the location and arrangement of the sockets and pivot member can be reversed. The free end of the stop member 620 preferably has a curved surface 626 that mates with a curved surface 628 formed on a stop portion of the push member, preferably formed as a lateral bar extending between the push member arms 434. In a preferred embodiment, the stop member 620 has a concave surface mating with a convex surface formed on the stop portion, although those surfaces can be interchanged. Alternatively, the stop member can be configured as a roller. In addition, the trigger member can alternatively be configured with a trip member.

In operation, the user moves the trigger member 120 along a path, as it is pivoted about the pivot axis 156 from the at-rest position, preferably in a lateral direction. During this sequence, as explained above, the stop member 620 is engaged with the push member 430 by way of the stop portion and prevents the push member 430 from pivoting about the pivot axis 156, thereby immobilizing the push member, and in particular the engagement portion 612 thereof During this sequence, the spring 602 is loaded, as energy is stored therein by way of the trigger member 120 being moved toward the push member 430. Preferably, the energy stored in the spring 602 as the trip member reaches the predetermined portion of its path exceeds the energy or force required to actuate the container. As the trigger member approaches the completion of the predetermined portion of the path, the spring flexes sufficiently such that the stop member 620 slides off of the stop portion of the push member, or the roller rolls out of engagement with the stop member, to a disengaged position, thereby allowing the push member 430, and in particular the engagement portion 612 thereof, to actuate the container as explained above, by moving in the longitudinal direction. The stop member can also flex, as it disengages from the stop portion of the push member.

In an alternative embodiment, shown in FIGS. 81 and 82, the stop member 620 is fixedly attached at one end to the housing, rather than being pivotally attached. In this embodiment, the stop member 620, which is preferably resilient, bends or flexes and eventually rolls off of or disengages from the stop portion of the push member, which is preferably curved or rounded. After the medication has been dispensed and the trigger is released, the stop member 620 springs back into engagement with the stop portion of the push member.

In an alternative embodiment, a trip member can be provided to disengage the stop member from the push member. Preferably, a spring 630, including for example and without limitation a cantilever, leaf or coil spring, is disposed between one of the housing and container and the stop member 620 and biases the stop member into the engaged position as the trigger member and push member are returned to the at-rest position. For example, in one preferred embodiment, a cantilever spring 630 extends from the stop member 620 and is biased against the housing and/or container.

Figure 52:
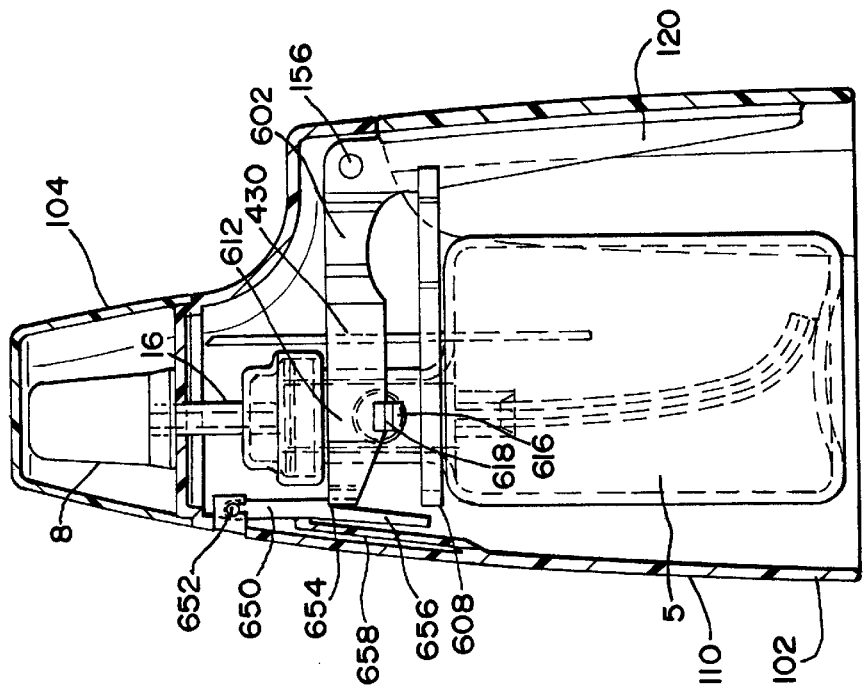
FIG. 52 is a front elevation view of an alternative embodiment of a nasal applicator.

Referring to the alternative preferred embodiment of FIGS. 52 and 64, the stop member is configured as a catch member 640 that engages an end of the push member 430, for example a lateral bar or roller extending between the arms 434, and immobilizes the push member. In this embodiment, the trigger member 120 is configured with a trip member 608 that engages the stop member 640 and disengages it from the push member 430 after the trigger member has completed a predetermined portion of its path of travel. After the actuation is complete, the stop member 640, which is resilient, springs back into engagement with the push member. The end of the stop member 640 is preferably tapered such that it slides back along the push member and is biased thereby during the return motion until it is again engaged with the push member 430.

Figure 53:
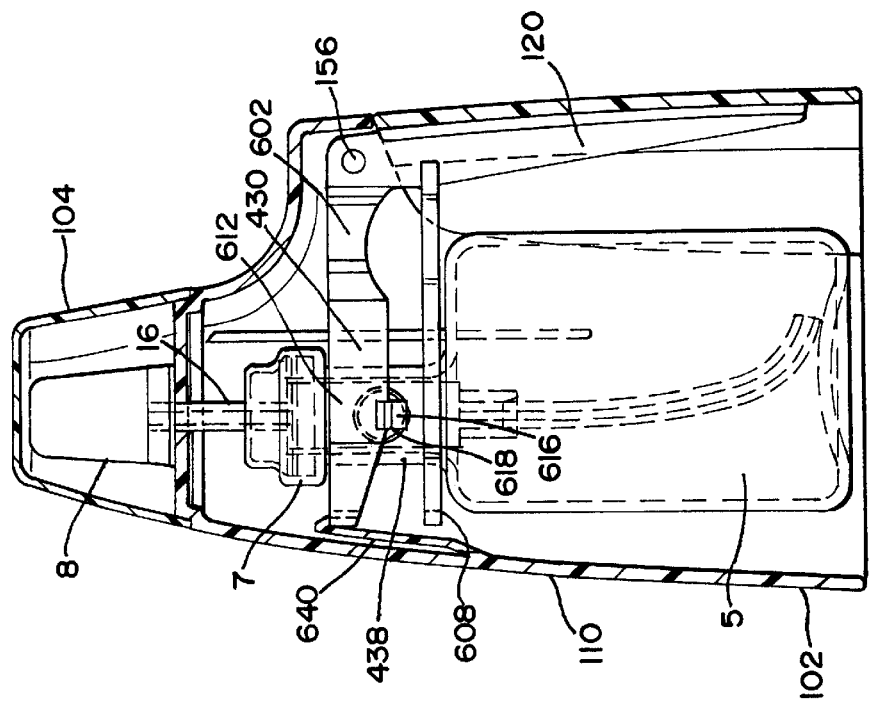
FIG. 53 is a front elevation view of an alternative embodiment of a nasal applicator.

Referring to the preferred embodiment of FIGS. 53 and 63, the stop member 650 is pivotally attached to the housing about pivot axis 652 and includes a stop surface 654 that engages an end of the push member, for example a lateral bar or roller, and immobilizes the push member 430. The stop member 650 further includes an arm portion 656 that extends downwardly from the stop surface 654. In this embodiment, the trigger member 120 is configured with a trip member 608 that engages the arm portion 656 of the stop member and disengages it from the push member 430 after the trigger member 120 has completed a predetermined portion of its path of travel. After the actuation is complete, a spring 658, which extends from the housing, biases the stop member 650 back into engagement with the push member 430. Alternatively, the spring can be formed on the stop member and interact with the housing. In yet another alternative embodiment, the spring can be formed separately from both the housing and stop member, and be coupled therebetween, for example as a coil or torsion spring.

Referring to FIG. 64, in yet another preferred alternative embodiment, the stop member 650 is pivotally or fixedly attached to the housing, and preferably includes an end portion having a curved surface 626 that rolls or slides off of a top portion formed on the end of the push member. The stop member 650, when pivotally attached, includes a spring 630 to bias it back into engagement after the trigger is released and the push member is returned to the at-rest position. When fixedly attached to the housing, the resilient stop member biases itself into engagement with the push member.

Figure 57:
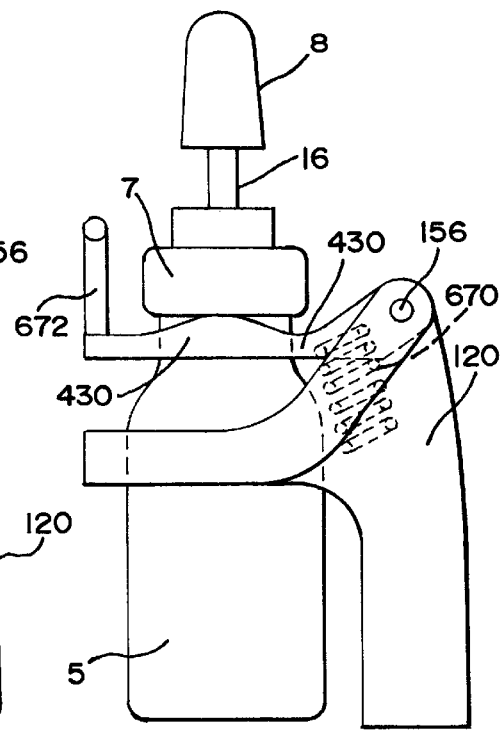
FIG. 57 is a front elevation view of an alternative embodiment of a nasal applicator.
Figure 58:
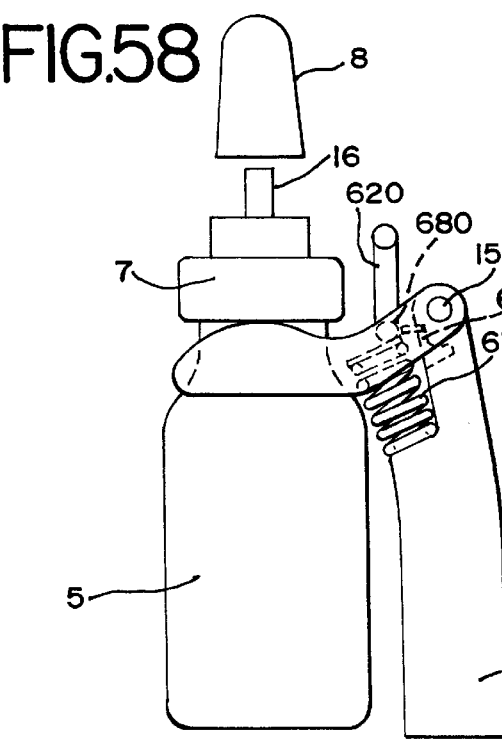
FIG. 58 is a front elevation view of an alternative embodiment of a nasal applicator.

Referring to FIGS. 57 and 58, another alternative embodiment of an actuator is shown as having a compression spring 670 disposed between the trigger member 120 and push member 430. In this embodiment, the trigger member 120 and push member 430 are preferably formed as separate parts, both pivotally mounted to the housing about the pivot axis 156. In operation, the spring 670 is compressed as the trigger member moves along the predetermined path. Referring to FIG. 57, the stop member 672, which is engaged with the end of the push member 430, can be disengaged by any of the devices described above, for example by a trip member or by rolling/sliding of the push member relative to the stop member.

Figure 59:
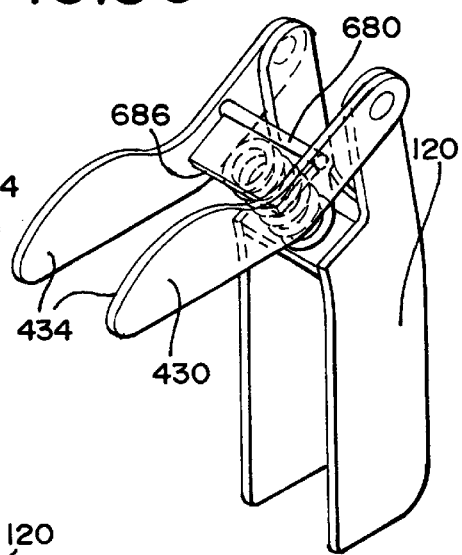
FIG. 59 is a perspective assembly view of a one preferred embodiment of a trigger member and a push member shown in FIG. 58.

In one preferred embodiment shown in FIGS. 58–60, the push member 430 further comprises a pivot member 680 pivotally secured thereto. In the at-rest position, the stop member 620 is engaged with the pivot member 680 and immobilizes the push member. The pivot member includes an arm portion 682. In operation, a trip member 684 connected to the trigger member 120 engages the arm portion 682 and rotates the pivot member 680 so as to roll the stop member 620 out of engagement with the pivot member 680, thereby releasing the push member. The stop member 620 preferably includes a return spring 630 to bias it to the engaged position after the container is actuated. The pivot member 680 can be rotated in the either the clockwise or counterclockwise direction. Preferably, the trip member includes a curved fillet at its base. As best shown in FIG. 59, the push member 430 and trigger member 120 each have support members (not shown), preferably configured as lateral cross members, which act against opposite ends of the spring 670. Preferably, the pivot member is pivotally 680 secured between the arm portions 434 of the push member 430.

In an alternative embodiment of the actuator, shown in FIGS. 61 and 62, a stop member 690 has a first end 692 pivotally connected to the housing and a second end 694 releasably engaged by the stop member. The first end can be pivotally secured to the housing with a pivot member 696, or can simply ride in a socket 698 formed in the housing. A portion of the stop member between the first and second ends 692, 694 engages the collar 7 on the container opposite the engagement portion 700 of the push member. The stop member 620 engages the stop member 690 adjacent the second end 694 and thereby immobilizes the push member 430 by way of the container collar 7. Preferably, the stop member 690 includes a pivot member 680, which can be pivoted with a trip member 684 to move the stop member 620 to a disengaged position. Of course, the stop member 620 can be disengaged from the stop member 690 by any of the various devices and methods disclosed herein.

The push member 430 includes an engagement portion 700 and a biasing portion 702, which can also be considered as part of the trigger member. A resilient spring portion 704 couples the engagement portion 700 and the biasing portion 702 and stores energy as the trigger member 120 is moved along the predetermined portion of its path. Once the trigger member 120 completes the predetermined portion of the path, the trip member 684, which preferably extends from the biasing portion of the push member, or trigger member, pivots the pivot member 680 and disengages the stop member 620. The spring 704 thereafter releases its energy as the engagement portion 700 moves a portion of the container upwardly and pivots the stop member 690 about axis 696.

Figure 56:
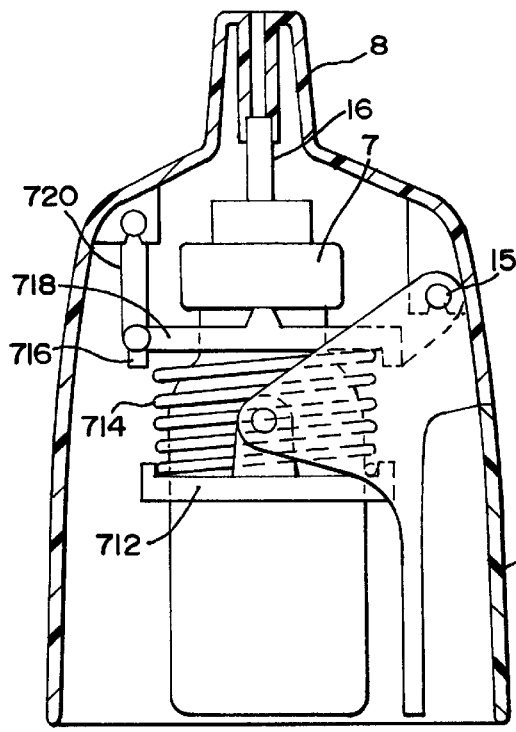
FIG. 56 is a front elevation view of an alternative embodiment of a nasal applicator.

In an alternative embodiment of the actuator, shown in FIGS. 55 and 56, an arm portion 710 extends from the trigger member 120. The push member includes biasing member 712, which is pivotally secured to the arm portion 710. A spring 714 is disposed between the biasing member 712 and an engagement portion 716 of the push member. Referring to FIG. 55, a pair of pivot members 718 are pivotally mounted on the engagement portion 716 and are engaged by a pair of stop members 720, which are pivotally mounted to the housing. The pivot members 718 each have an end portion extending inwardly, with the ends 722. In operation, the trigger member 120 is moved along the predetermined path thereby loading the spring 714 as it is compressed between the biasing member 712 and the engagement portion 716, which is immobilized by the stop members 720. As the biasing member 712 reaches the pivot members 718, one or both of the biasing member 712 and arm portion 710, which are preferably configured with a rounded portion, engage and pivot the pivot members so as to disengage the stop members 720 therefrom, thereby releasing the engagement portion 716 to actuate the container.

Referring to FIG. 56, the actuator is substantially the same as the embodiment of FIG. 55, except that it is configured with only one pivot member and stop member 720.

Figure 83:
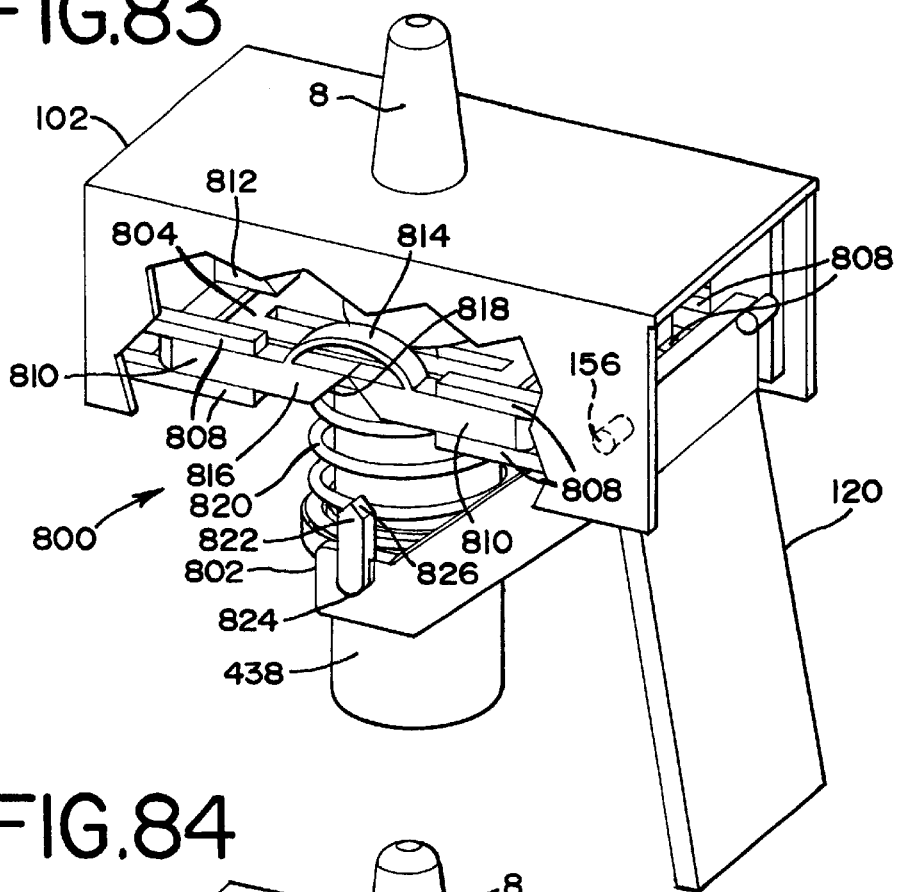
FIG. 83 is a partial perspective view of an alternative embodiment of a trigger member, push member and stop member in an at-rest position.
Figure 84:
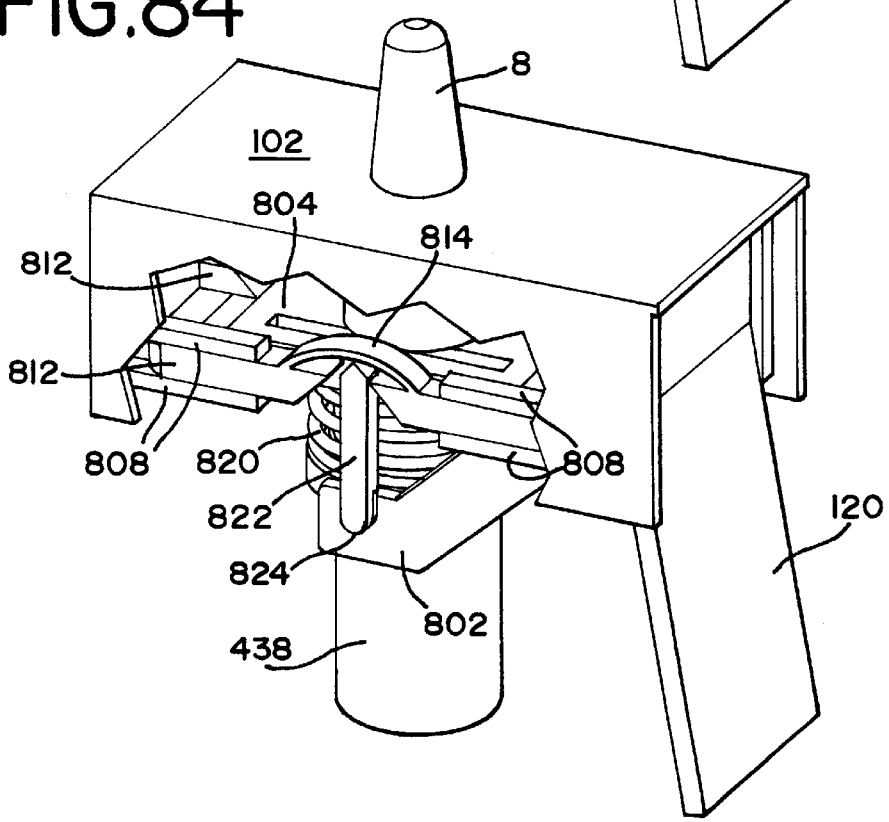
FIG. 84 is a partial perspective view of the trigger member, push member and stop member of FIG. 83 shown in an actuated position.

Referring to FIGS. 83 and 84, an alternative preferred embodiment of an actuator includes a push member 800 having a biasing member 802 and an engagement member 804 with a spring 820 disposed therebetween. The engagement member 804 is engaged with the neck 438 of the container. A pair of tracks 808 or guides are formed on and/or extend from the housing on opposite sides of the neck. A pair of stop members 810 are slidably mounted in the tracks 808 on each side of the container. Each stop member 810 includes a catch 812 or latch portion that engages an upper surface of the engagement member 804 to prevent the engagement member and container from being moved in the longitudinal direction. Preferably, each stop member 810 has an end portion 816 having a tapered surface 818, with the tapered surfaces of the end portions positioned proximate one another to form a V-shape, preferably at an angle of about 90 degrees. Preferably, the stop members 810 are joined with a leash, or flexible lanyard, shown as a curved flexible portion, which also acts as a spring 814.

In operation, the trigger member 120 is moved along the predetermined path. The biasing member 802, which extends from the trigger member, pivots about pivot axis 156. The biasing member includes a pair of trip members 822, each preferably having a pointed end portion 826 shaped to mate with the tapered end portions 816 of the stop members 810 and opposite ends that are received in pivot pockets 824. As the biasing member 802 moves toward the engagement member 804, which is immobilized by the stop members 810, the spring 820 is loaded. Eventually, the trip members 822 engage the ends 816 of the stop members and push the stop members 810 laterally outward in the tracks 808 until the catch 812 disengages from the engagement member 804, which is then biased upwardly by the spring 820 to actuate the container 5. After the trigger member 120 is released, the container returns to the at-rest position, and the spring 814 moves the stop members 810 back into engagement with the engagement member 804.

Preferably, in each of the various preferred embodiments described herein, the container, push member(s) and trigger member(s) are returned or biased to the at-rest position relative to the stem and holder by an internal spring in the container pump or valve mechanism, although it should be understood that additional return springs can be provided to act on those members, individually or collectively. It should be understood that the various push members, stop members and trigger members can be interchanged, and that the embodiments are not limited to the specific combinations shown in each of the respective Figures.

Referring to FIGS. 40–46, an indicator mechanism 500 is shown. It should be understood that this mechanism can be incorporated into any of the above-referenced actuator embodiments having one or more trigger and/or pusher members, and that the specific embodiment of the holder and trigger member in FIGS. 40–46 are meant to be illustrative rather than limiting as related to their use with the indicator mechanism. In addition, the indicator mechanism can be incorporated into other types of dispensers and actuators, as shown for example in published U.S. patent application U.S. 2002/0008122 A1, which is hereby incorporated herein by reference.

In one preferred embodiment, the indicator mechanism includes an indicator member 502 and a drive mechanism 520. The indicator member 502 is preferably configured as a wheel, which is rotatably mounted to the housing about a pivot axis 504. The indicator member, or housing, can include an axle 510 that mates with the other of the indicator member or housing. Various dosage indicia, including without limitation, various alpha-numerical characters, symbols, colors, shading, grids, lines, etc., are provided on an upper face 506 of the indicator member so as to be visible through a viewing window 508 formed in the housing. The viewing window can have any shape, and can be formed simply by providing an opening in the holder that allows a portion of the indicator member to be seen. In one alternative embodiment, the indicia are provided along a circumferential surface of the indicator member, so as to be visible to the user through a viewing window.

The dosage indicia indicate to the user the amount of medicament remaining in the container, or dispensed therefrom. For example, the indicia can have a series of numbers, e.g., from 0 to 200, corresponding to the number of doses in the container. As the indicator wheel moves, the number counts down from 200 or up from 0 until the final number is reached, thereby notifying the user that the container is empty. Similarly, the indicia can take the form of colors, which move from green to red as the indicator member is rotated so as to indicate that the container is being emptied. These, and other types of indicia and indicator mechanisms, are disclosed, for example, in U.S. Pat. No. 6,161,724 to Blacker et al. and U.S. Pat. No. 6,082,358 to Scarrot et al., the entire disclosures of which are hereby incorporated by reference herein.

The drive mechanism 520 includes a pawl 522, a worm 530 and a ratchet gear 532. The pawl 522 is configured as a U-shaped flexible hook arm having an engagement end portion 524, that extends upwardly from the push member. It should be understood that the pawl 522 can extend from, or be connected to either the push member or the trigger member, collectively referred to as an actuator member, and that it can be formed integrally therewith or as a separate part connected thereto.

The worm 530 and ratchet gear 532 are coaxially mounted on an axle 534 that is rotatably mounted to the housing 102, and in particular in sockets 536 formed in the housing. The worm 530, axle 534 and ratchet gear 532 are preferably integrally formed as a one-piece member, although they can be made as separate parts, or some combination of separate and integral parts. A worm gear 540 is formed on, or is connected to, a bottom of the indicator member 502, and includes teeth 542 meshing with the worm 530.

In operation, as the user moves the trigger member 120 and push member 430, the end portion 524 of the pawl 522 engages at least one tooth 526 of the ratchet gear 532 and rotates the ratchet gear an incremental amount corresponding to the circular pitch of the gear, or the distance between adjacent teeth 526. As the ratchet gear 532 is rotated, the worm 530 also is rotated therewith and thereby meshes with and rotates the worm gear 540 and adjoined indicator member 502 an incremental amount. The incremental amount of rotation of the indicator member 502 is dependent upon the pitch of the worm 530, the number of worm threads, and the pitch of the worm gear 540. As the trigger member 120 is released, the pawl 522, and in particular the end portion 524 thereof, slides back over at least one of the teeth 526 of the ratchet gear 532 so as to be positioned for engagement with the next tooth thereon.

A non-return member 560 preferably extends from the housing 102 and engages at least one of the teeth 526 on the ratchet gear 532 so as to prevent it from rotating in an opposite direction. Accordingly, the return member 560 ensures that the ratchet gear 532 can be rotated in only one direction, such that the indicator member 502 cannot be rotated the wrong way, with the attendant misinformation about the doses remaining in or dispensed from the container 5.

In one preferred embodiment, the indicator member 502 makes only a single revolution corresponding to a complete evacuation of the container 5. To achieve this result, the ratchet gear 532, worm 530 and worm gear 540 are configured to provide the appropriate reduction ratio. In particular, the number of teeth on the ratchet gear and worm gear, and the pitch of the worm, can be varied to provide an appropriate reduction ratio. For example, in one embodiment, the ratchet gear has between 6 and 16 teeth. Preferably the worm thread pitch is in the range of 1.0–3.0 mm, and most preferably 1.5 mm Also, the worm gear preferably has a circumference of 33.3 mm (e.g. 50 teeth). Other worm gear circumferences may be selected to provide a different desired reduction ratio.

It one preferred embodiment, the indicator member 502 moves or rotates an incremental amount upon each movement of the trigger member 120 and push member 430, corresponding to a single actuation of the container 5. However, it should be understood that the indicator mechanism 500 could be configured to rotate the indicator member 502 an incremental amount upon a predetermined number of movements of at least one of the trigger member and push member that is greater than one.

It should be understood that the indicator mechanism can have its various parts molded with or secured directly to the housing, or holder, or can be manufactured as a separate module, having a housing that is mounted inside the holder. For example and without limitation, the module can be secured to the holder with a snap fit, or by bonding and/or with fasteners. In this way, the indicator module can be installed easily in a variety of different holders. In one exemplary embodiment, an actuator has a first end that extends from the module housing to engage one of the push member and trigger member, with an opposite end of the actuator forming a pawl that engages the ratchet gear.

It should be understood that the position of the various mating hinge pockets and hinge pins can be reversed on the various holders, trigger members, and push members. For example, and without limitation, the holder can be configured with one or more hinge pins that are inserted into one or more hinge pockets formed on the trigger member.

Preferably, the various holders, trigger members, pusher members and indicator mechanism components are made of a polypropylene (PP), polyethylene (PE) or other thermoplastic material that can be molded. It should be understood that the various actuators, which preferably include a holder, one or more trigger members and one or more push members also can be configured to actuate other types of containers, including for example and without limitation pressurized metered dose inhaler (PMDI) containers, which are used to introduce various medicaments, preferably in the form of an aerosol, to the lungs of the user via the mouth, and are not limited to the actuation of the nasal applicators shown in the Figures. In such embodiments, the holder includes a mouthpiece, which is inserted into the mouth of the user, rather than a nozzle, which is inserted into one or more of the user's nostrils.

In a preferred embodiment, the length of the nozzle 8, which preferably is configured with a cylindrical interior passageway 14, is reduced. As explained above, the interior passageway 14 is disposed on stem 16, which extends from the holding chamber, preferably with a friction fit. In one embodiment, the passageway is slightly larger at the bottom thereof so as to receive the stem and form a shoulder that engages the top of the stern. In one exemplary embodiment, the passageway 14 can have a diameter of about 0.19 inches, and the nozzle can be reduced from a length of about 1 inch to about 0.50 inches. A length of between about 0.10 inches and about 0.60 inches would also be suitable. In this way, the energy needed to expel the substance is reduced. In addition, air may be compressed in a separate chamber and thereafter introduced into the nozzle at the end of the stroke to clear the nozzle and accelerate the last droplets. The nozzle has an end with one or more outlets 10 formed thereon.

The nozzle, including the passageway and the outlets, can be configured in many different ways. One suitable configuration is shown and described in U.S. Pat. No. 4,801,093, which is hereby incorporated herein by reference. In such an embodiment, the end of the nozzle is closed by a wall, which has the outlet formed therein. In one preferred embodiment, the outlet 10 has a smaller diameter than the passageway 14. The wall can have a central portion and an outer portion, with the outer portion preferably being thicker than the central portion. At least one groove (not shown) can be formed on an inner surface of the wall. The one or more grooves extend from the cylindrical wall of the passageway to a cavity that surrounds the outlet, so as to provide a spraying chamber. The grooves are not radially arranged, but rather are sequentially circumferentially arranged to provide a swirling movement to the substance, preferably a liquid or aerosol, expelled through the outlet.

Referring to FIGS. 1–5, an elongated diffuser 20, or adapter, is shown as having a first, lower portion 22 having a generally open first end and a cavity 24 shaped to be inserted or disposed on the nozzle 8, preferably with a friction fit. A second, upper portion 26 extends longitudinally from the first portion. The second portion terminates in a generally open end forming an outlet 28 and has a passageway 30 formed therein that communicates between the lower portion cavity 24 and the outlet. Preferably, the passageway 30 is tapered, or has a frusto-conical shape, such that it increases in diameter or cross-section from a lower portion thereof to the outlet. In particular, the passageway 30 is configured as a venturi type passageway. In one preferred embodiment, the passageway 30 is tapered from about 0.40 inches at the distal output end to about 0.19 inches adjacent the output end of the nozzle, with the interior surface being angled at about 5°. It should be understood, however, that the passageway may have a relatively constant cross-sectional area, which is preferably greater than the cross-sectional area of the passageway in the nozzle, and that it may also be tapered in a reverse direction.

In the embodiment shown in FIGS. 1–5, the end of the second portion 26 is configured with a rim 32. The rim provides an ideal structure to seal with the interior of the nasal cavity. Also in this embodiment, the exterior 36 of the diffuser is flared or tapered to correspond to the shape of the passageway, as the diffuser is configured with a single wall thickness.

The nozzle 8 of the actuator is inserted into the lower portion 22 such that the outlet 18 of the nozzle communicate with a proximate, lower, narrow portion of the passageway, which is spaced from the outlet. The diffuser 20 further preferably includes one or more inlets 40, and preferably a plurality of inlets, with the term plurality meaning more than one, spaced circumferentially around the diffuser. In various preferred embodiments, three or five inlets are provided. The inlets 40 preferably extend radially between the exterior of the diffuser and communicate with the interior thereof, preferably at a location adjacent the outlet of the nozzle, or near the lower, narrower portion of the passageway 30. In one exemplary embodiment, the inlets preferably have a width of about 0.08 inches.

The overall length of the nozzle 8 and diffuser 20 is approximately 1 inch, which is approximately the same length as many conventional nozzles. In this way, the end of the nozzle, or the end of the cylindrical passageway formed therein, is moved further away from the surface area of the nasal cavity, which allows the spray to become more diffuse with smaller droplets. This further promotes the absorption of the substance into the nasal cavity, for example into the nasal turbinates.

In an alternative embodiment shown in FIGS. 6–8, the exterior 50 of the diffuser has an outer wall 52 that provides a tapered surface having a lesser diameter or cross-section at the outlet end of the diffuser. The lower portion also includes a stepped portion having a shoulder that mates with the nozzle.

Referring to FIGS. 9–9C, the diffuser 62 can be configured with a baffle member 60, which is disposed across the passageway, as shown for example in FIG. 9. For example, the baffle member 60 can extend across the outlet 68 adjacent the distal end of the diffuser. Alternatively, the baffle member can be disposed in a lower portion of the passageway adjacent the outlet of the nozzle, or at any point along the passageway. The outlet is preferably configured as a plurality of arcuate shaped openings 68 formed around the circumference of the baffle member. The baffle member 60 preferably has a convex upper, exterior surface 64 and a convex lower, interior surface 66, with the lower portion of the baffle extending downwardly into the passageway 70. The convex, or otherwise tapered, exterior surface 64 of the baffle member can facilitate the insertion of the diffuser into the nasal cavity. It should be understood that the lower, interior portion of the baffle can also be configured with a concave surface. Referring to FIGS. 9A and 9B, the passageway 70 is tapered from a greater diameter at the base thereof to a lesser diameter adjacent the outlets 68 or baffle 60. A lower portion 72 of the passageway has a concave shape and forms a bowl-shaped cavity, the bottom of which communicates with an upper portion 74 of the passageway that receives the stem of the container. A nozzle portion of the diffuser 86 can be disposed in the diffuser and defines the lower portion 72 of the passageway and the passageways 74 and 76. The diffuser portion 62 can be integrally formed with the actuator, or it can be made as a separate member that can be removed from the nozzle portion and actuator for cleaning. Similarly, the nozzle portion can be formed integrally with the actuator, or as a separate member. The upper portion 74 of the passageway preferably has a smaller diameter than the lower portion 76 of the passageway, which is shaped to receive the stem The actuator further includes a guide 80 shaped to receive and guide an upper portion of the container. A second baffle 82 separates the lower portion 72 of the passageway and the upper, tapered portion 70 of the passageway. The second baffle 82 can be configured with a plurality of openings or apertures, and can be made, for example, of a screen material.

In one embodiment, the outlet 10 may have an opening of 4 mm, or when configured with a baffle, may have a series of holes to allow the aerosol to enter the nasal passage at any angle. As described above, the baffle member may include a series of holes around the center thereof. This will give the finer particles 100 microns and less an escape route from the baffle area. In one preferred embodiment, the diffuser is separable from the actuator so as to allow the draining and cleaning of the inside of the diffuser between treatments.

It should be understood that the nozzle 8, and/or the entire actuator, and the diffuser 20 can be made as a single integrally molded actuator or diffuser, referred to when combined as such as either a diffuser or a nozzle, and as having a diffuser portion and a nozzle portion, which in one embodiment can be disposed on the stem, or can further be integrally molded with the holding chamber. In this context, it should be understood that the "nozzle portion" refers to that portion of the diffuser or actuator that engages the stem portion of the container, whether made as a separate member or integrated with the diffuser portion. In one such embodiment, the diffuser, preferably integrated into an actuator, would have a nozzle portion with a first, lower passageway 14 having a generally cylindrical cross-section that communicates with the stem 16 extending from the holding chamber, and a diffuser portion with a second, upper passageway 30, preferably having one or more of the tapered configurations described above. In either embodiment, whether integral or made separately, the nozzle and/or diffuser can be made of a hard plastic, or can be made of a more pliant material, such as silicone.

In yet another embodiment, shown in FIGS. 27–36, a second, upper diffuser portion 260 of a diffuser 256 has a bulb-like or substantially spherical exterior shape or contour. More specifically, the exterior shape of the upper diffuser portion 260 is formed as a zone of a sphere, with a lower end thereof being connected to the lower nozzle portion 262 of the diffuser and the upper surface thereof being substantially fiat, or tapered slightly downward and inward. In one preferred embodiment, the radius of the spherical portion is about 0.28 inches. A smaller radius may be provided to accommodate users with smaller nostril openings, such as children. Preferably, the upper portion has a height of between about 0.40 inches and about 0.45 inches, with the lower portion having a height of about 0.50 inches. Alternatively, the combined height of the upper and lower portions is about 0.83 inches.

In operation, the user simply inserts the bulbous upper portion into the nostril until it can go no further. At this location, the outlet 28 of the diffuser is located at the entry point of the nasal cavity, which leads to the nasal turbinates. In addition, the spherical shape facilitates the sealing of the entrance to the nasal cavities, which in turn helps to direct the ambient air to flow throughout the diffuser passageway and fully evacuate the remaining medicament during inhalation. The sizable shape of the spherical diffuser helps spread the soft tissues of the inside of the lining of the nostril's cavity at a distance from the high velocity particles exiting the stem. The spherical diffuser is more forgiving in situations when the device is not properly directed during application of the medicament, and it has a "friendlier" appearance, especially when viewed by children.

The diffuser further includes a pair of inlets 264 communicating with the passageway 30 directly adjacent the nozzle portion output end. Preferably, the inlets 264 are not positioned directly opposite each other, and are not directed at and do not extend radially from the longitudinal axis 300 of the nozzle and passageways, but rather are offset from each other on opposite sides of the axis so as to create a cyclonic or swirling flow in the passageway. Additional vanes can be added within the passageway to further direct the flow. Preferably, the inlets are directed tangentially along the interior wall of the diffuser substantially perpendicular to the axis 300. Preferably, the inlets 264 each have a diameter of 0.10 inches. The inlets facilitate the cleaning of the device, as they will allow water, or other cleaning fluids, to drain therethrough. Preferably, the outlet opening 28 has a diameter of between about 0.30 inches and about 0.56 inches. Accordingly, in one preferred embodiment, the ration of the inlet openings to the outlet is about 56:20. In one embodiment, the diameter of the outer rim portion of the diffuser at the top thereof is about 0.46 inches, with the rim tapering down to the outlet opening.

Preferably, the passageway 30 is tapered at about 6 degrees from bottom to top. In one preferred embodiment, the diameter of the passageway at the bottom of the diffuser portion is about 0.22 inches, with the diffuser tapering to an exit diameter of about 0.30 inches.

Referring to FIGS. 27–31, the diffuser 256 is integrally formed as part of an actuator. The overall height of the device, including the container, is about 3.68 inches, with the height between the bottom of the container and the shoulder, which is the distance required for the fingers to activate the device, being about 1.95 inches, compared with about 3.00 inches for a conventional device. The nozzle portion 262 of the diffuser further includes a nozzle insert 282, which is disposed on and engages the stem and is inserted into a cavity formed in the lower nozzle portion of the diffuser. Alternatively, the lower nozzle portion of the diffuser can be configured with a passageway shaped to engage the stem of the container. An upper portion 284 of the actuator holder, which is connected to the lower, nozzle portion 262 of the diffuser, has a pair of scalloped openings 286 formed opposite each other to provide room for the user's fingers as they engage the shoulder of the holder. A pair of protuberances 290, or ribs, extend upwardly at the outer portion of the shoulder to help locate the user's fingers. In this embodiment, the user grips the shoulders 288 of the actuator with the index and middle fingers, or other available fingers, and pushes the bottom 178 of the container upwardly with their thumb or other available fingers so as to move the holding chamber of the container relative to the stem and thereby dispense a dose of medicament.

In operation, the diffuser 20 separates the end of the nozzle, and the outlet 10 thereon, from the impaction surface of the nasal cavities, which reduces the irritation that can be caused by the direct impact of high velocity particles on the soft nasal tissues. In this way, the tapered passageway 30 slows the particles down, as well as increases the distance between the end of the nozzle, or cylindrical passageway, and the nasal cavities. In addition, when configured with inlets 40, ambient air can be pulled into the passageway to help evacuate the passageway as the user inhales and to further enhance the particle distribution by breaking down larger particles into smaller particles that will be absorbed in the nasal cavity, in particular the nasal turbinates.

Figure 14:
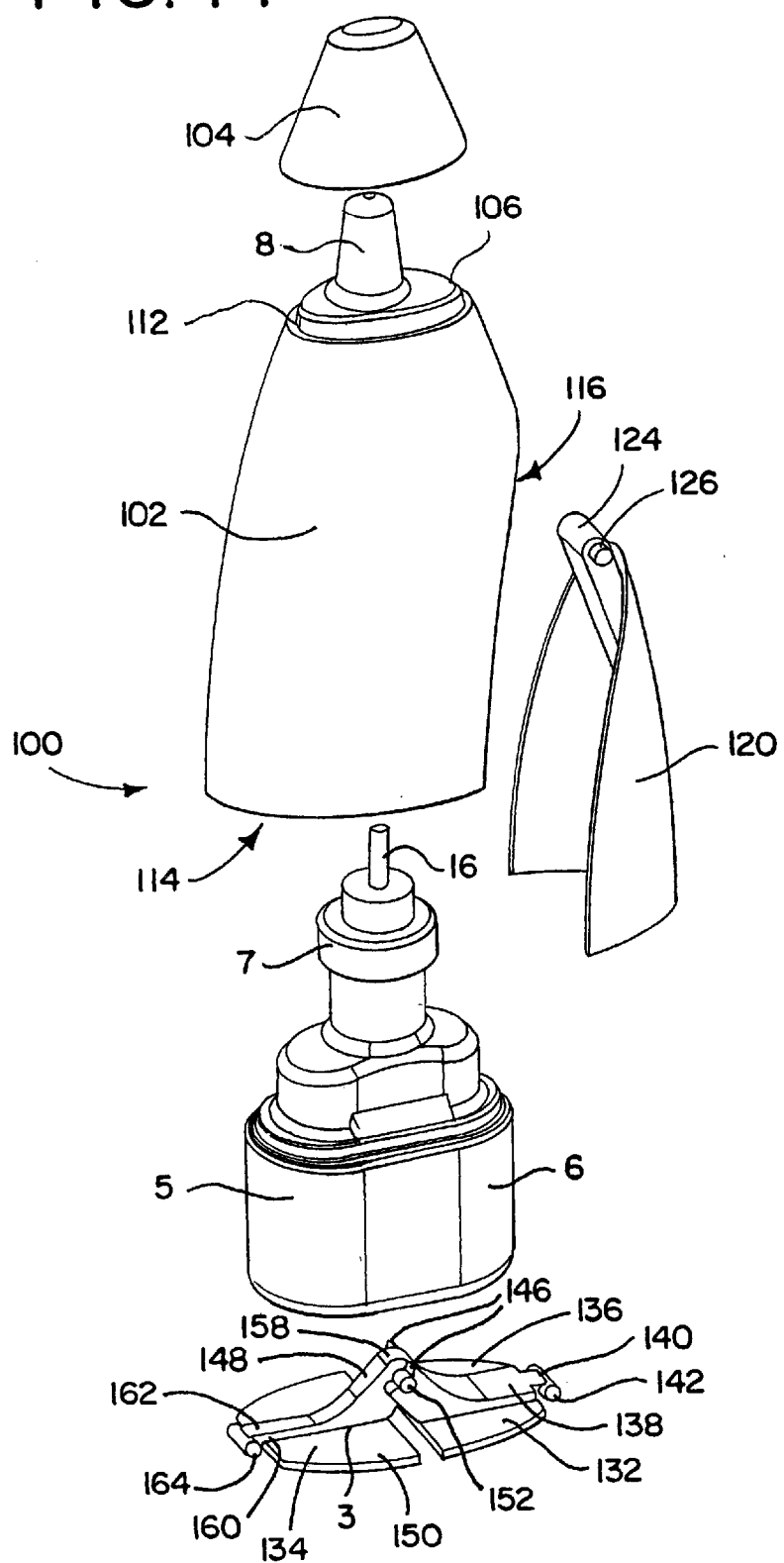
FIG. 14 is an exploded, top perspective view of a nasal applicator.

Referring to FIG. 37, yet another alternative embodiment of an actuator 300 is shown. This embodiment comprises a holder 316 such as is shown in FIG. 14 and, instead of a nozzle 8 as shown in FIG. 14, it comprises a diffuser 356 having a nozzle portion 362 with an air inlet 364 and an upper diffuser portion 360 defining an outlet 328 similar to the structure shown in FIG. 28. The holder 316 in this embodiment also comprises indentations 302 located towards the bottom portion of the holder. One or more indentations 302 are also positioned on the trigger 320. The indentations 302 allow a user to properly grip the holder in order to actuate the applicator with a push member 330. In other embodiments, the holder and trigger may have protrusions extending from their respective surfaces to provide a gripping surface.

It should be understood that any and all of the various actuators disclosed herein can be configured with one of the various diffusers disclosed herein.

Though various features of the preferred embodiments described above are preferably used together, it should be understood that many of the features described above can be used separately. Moreover, the foregoing detailed description has discussed only a few of the many forms that this invention can take. Therefore, although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. An actuator for use in dispensing a medicament from a container having at least a first and second portion, said actuator comprising:
a holder having a grippable portion, wherein said holder is adapted to engage at least the first portion of the container;
a trigger member pivotally connected to said holder at a pivot axis, wherein said trigger member is pivotable about said pivot axis in a first rotational direction toward said grippable portion and a second rotational direction opposite said first direction, wherein said trigger member follows a path as said trigger member is pivoted about said pivot axis in said first rotational direction;
a push member connected to said trigger member, wherein said push member is pivotable about said pivot axis in said first rotational direction in response to said trigger member pivoting in said first rotational direction, wherein said push member is pivotable about said pivot axis in said second rotational direction as said trigger member is pivoted in said second rotational direction, wherein said push member comprises an engagement portion adapted to engage the second portion of the container, wherein said push member is adapted to move at least the second portion of the container relative to said holder, and wherein at least a portion of said push member is moved in a substantially non-parallel relationship to at least a portion of said trigger member as said push member and said trigger member are pivoted in the first and second rotational directions respectively; and
a stop member moveable between an engaged position and a disengaged position, wherein said stop member is engaged with said push member and immobilizes said engagement portion when said stop member is in said engaged position, and wherein said stop member is maintained in said engaged position as said trigger member is pivoted in said first rotational direction along at least a portion of said path.

2. The invention of claim 1 further comprising an indicator member rotatably mounted to said holder and a drive mechanism connected between said indicator member and at least one of said trigger member and said push member, wherein a predetermined number of movements at least one of said trigger member and said push member in at least one of said first and second rotational directions causes said drive mechanism to move said indicator member an incremental amount.

3. The invention of claim 2 wherein said predetermined number is one movement of said at least one of said trigger member and said push member.

4. The invention of claim 2 wherein said drive mechanism comprises a pawl connected to one of said trigger member and said push member, a worm rotatably mounted to said holder, and a ratchet gear coaxially mounted with said worm, and wherein said indicator member comprises gear teeth meshing with said worm, wherein said pawl member is engageable with and moves said ratchet gear as said one of said trigger member and said push member moves in at least one of said first and second rotational directions.

5. The invention of claim 4 further comprising a non-return member connected to said housing, wherein said non-return member is engageable with said ratchet gear and prevents movement of said ratchet gear in at least one direction.

6. The invention of claim 1 wherein said trigger member and said push member are integrally formed as a one-piece member.

7. The invention of claim 1 further comprising a spring biasing said stop member into said engaged position.

8. The invention of claim 1 further comprising a trip member coupled to said trigger member, said trip member moveable between at least an engaged position, wherein said trip member is engaged with said stop member after said trigger member has moved along a predetermined portion of said path, and a disengaged position, wherein said trip member disengages said stop member from said push member when said trip member is moved to said engaged position.

9. The invention of claim 8 wherein said stop member comprises a catch member engaging said push member.

10. The invention of claim 8 further comprising a spring coupled between said trigger member and said push member.

11. The invention of claim 10 wherein said spring is integrally formed between said trigger member and said push member.

12. The invention of claim 1 wherein said push member comprises a biasing member and a spring disposed between said biasing member and said engagement portion.

13. The invention of claim 12 wherein said biasing member is pivotally connected to said trigger member, and wherein said stop member is engaged with said engagement portion.

14. The invention of claim 13 wherein said stop member comprises a pair of stop members engaged with said engagement portion.

15. The invention of claim 13 further comprising a trip member engaged with at least one of said stop member and said engagement portion after said trigger member has moved along a predetermined portion of said path, wherein said trip member moves said stop member from said engaged position to said disengaged position.

16. The invention of claim 1 wherein said push member comprises a stop portion having a curved surface, and wherein said stop member engages said curved surface.

17. The invention of claim 16 wherein said curved surface is a first curved surface and wherein said stop member has a second curved surface mating with said first curved surface.

18. The invention of claim 1 wherein said push member comprises a pivot member engaged with said stop member, and a trip member coupled to said trigger member, said trip member moveable between at least an engaged position, wherein said trip member is engaged with said pivot member after said trigger member has moved along a predetermined portion of said path, and a disengaged position, wherein said pivot member disengages said stop member from said push member when said trip member is moved to said engaged position.

19. The invention of claim 1 wherein said trigger member is a first trigger member and wherein said grippable portion of said holder comprises a second trigger member.

20. An actuator for use in dispensing a medicament from a container having at least a first and second portion, said actuator comprising:
a holder having a grippable portion, wherein said holder is adapted to engage at least the first portion of the container;
a trigger member pivotally connected to said holder at a pivot axis, wherein said trigger member is pivotable about said pivot axis in a first rotational direction toward said grippable portion and a second rotational direction opposite said first direction, wherein said trigger member follows a path as said trigger member is pivoted about said pivot axis in said first rotational direction;

a push member connected to said trigger member, wherein said push member is pivotable about said pivot axis in said first rotational direction in response to said trigger member pivoting in said first rotational direction, wherein said push member is pivotable about said pivot axis in said second rotational direction as said trigger member is pivoted in said second rotational direction, wherein said push member comprises an engagement portion adapted to engage the second portion of the container, wherein said push member is adapted to move at least the second portion of the container relative to said holder, and wherein at least a portion of said push member is moved in a substantially non-parallel relationship to at least a portion of said trigger member as said push member and said trigger member are pivoted in the first and second rotational directions respectively; and a first stop member adapted to engage said second portion of said container in opposition to said push member, and a second stop member moveable between an engaged position and a disengaged position, wherein said second stop member is engaged with said first stop member and immobilizes said engagement portion when said second stop member is in said engaged position, and wherein said second stop member is maintained in said engaged position as said trigger member is pivoted in said first rotational direction along at least a portion of said path.

21. The invention of claim 20 further comprising a trip member coupled to at least one of said trigger member and said push member, said trip member moveable between at least an engaged position, wherein said trip member is engaged with said one of said first and second stop members after said trigger member has moved along a predetermined portion of said path, and a disengaged position, wherein said trip member disengages said second stop member from said first stop member when said trip member is moved to said engaged position.

22. The invention of claim 21 wherein said first stop member comprises a pivot member engaged with said second stop member, wherein said trip member engages said pivot member when said trip member is moved to said engaged position.

23. An inhaler for dispensing a medicament comprising:
a container having a first portion moveable relative to a second portion along a longitudinal axis in a longitudinal direction;
a holder comprising a grippable portion, said holder engaging at least said first portion of said container;
a trigger member pivotally connected to said holder at a pivot axis, wherein said trigger member is pivotable about said pivot axis in a first rotational direction toward said grippable portion and a second rotational direction opposite said first direction, wherein said pivot axis is substantially perpendicular to said longitudinal axis, wherein at least a portion of said trigger member moves in a lateral direction substantially non-parallel to said longitudinal direction as said trigger member is pivoted in said first and second rotational directions, and wherein said trigger member follows a path as said trigger member is pivoted about said pivot axis in said first rotational direction;
a push member connected to said trigger, wherein said push member is pivotable about said pivot axis in said first rotational direction as said trigger member is pivoted in said first rotational direction, wherein said push member is pivotable about said pivot axis in said second rotational direction as said trigger member is pivoted in said second rotational direction, wherein said push member comprises an engagement portion engaging the second portion of the container and moves said second portion relative to said holder and said first portion of said container in said longitudinal direction as said push member is pivoted in said first rotational direction; and a stop member moveable between an engaged position and a disengaged position, wherein said stop member is engaged with one of said push member and said container and immobilizes said engagement portion when said stop member is in said engaged position, and wherein said stop member is maintained in said engaged position as said trigger member is pivoted in said first rotational direction along at least a portion of said path.

24. The invention of claim 23 further comprising an indicator member rotatably mounted to said holder and a drive mechanism connected between said indicator member and at least one of said trigger member and said push member, wherein a predetermined number of movements at least one of said trigger member and said push member in at least one of said first and second rotational directions causes said drive mechanism to move said indicator member an incremental amount.

25. The invention of claim 24 wherein said predetermined number is one movement of said at least one of said trigger member and said push member.

26. The invention of claim 24 wherein said drive mechanism comprises a pawl connected to one of said trigger member and said push member, a worm rotatably mounted to said holder, and a ratchet gear coaxially mounted with said worm, and wherein said indicator member comprises gear teeth meshing with said worm, wherein said pawl member is engageable with and moves said ratchet gear as said one of said trigger member and said push member moves in at least one of said first and second rotational directions.

27. The invention of claim 26 further comprising a non-return member connected to said housing, wherein said non-return member is engageable with said ratchet gear and prevents movement of said ratchet gear in at least one direction.

28. The invention of claim 23 wherein said trigger member and said push member are integrally formed as a one-piece member.

29. The invention of claim 23 further comprising a spring biasing said stop member into said engaged position.

30. The invention of claim 23 further comprising a trip member coupled to said trigger member, said trip member moveable between at least an engaged position, wherein said trip member is engaged with said stop member after said trigger member has moved along a predetermined portion of said path, and a disengaged position, wherein said trip member disengages said stop member from said one of said push member and said container when said trip member is moved to said engaged position.

31. The invention of claim 30 wherein said stop member comprises a catch member engaging said push member.

32. The invention of claim 30 further comprising a spring coupled between said trigger member and said push member.

33. The invention of claim 32 wherein said spring is integrally formed between said trigger member and said push member.

34. The invention of claim 23 wherein said push member further comprises a biasing member and a spring disposed between said biasing member and said engagement portion.

35. The invention of claim 34 wherein said biasing member is pivotally connected to said trigger member, and wherein said stop member is engaged with said engagement portion.

36. The invention of claim 35 wherein said stop member comprises a pair of stop members engaged with said engagement portion respectively.

37. The invention of claim 35 further comprising a trip member engaged with at least one of said stop member and said engagement portion after said trigger member has moved along a predetermined portion of said path, wherein said trip member moves said stop member from said engaged position to said disengaged position.

38. The invention of claim 23 wherein said push member comprises a stop portion having a curved surface, and wherein said stop member engages said curved surface.

39. The invention of claim 38 wherein said curved surface is a first curved surface and wherein said stop member has a second curved surface mating with said first curved surface.

40. The invention of claim 23 wherein said push member comprises a pivot member engaged with said stop member, and a trip member coupled to said trigger member, said trip member moveable between an engaged position, wherein said trip member is engaged with pivot member after said trigger member has moved along a predetermined portion of said path, and a disengaged position, wherein said pivot member disengages said stop member from said push member when said trip member is moved to said engaged position.

41. The invention of claim 23 wherein said stop member comprises a first stop member engaging said second portion of said container in opposition to said push member, and a second stop member moveable between said engaged position and said disengaged position, wherein said second stop member is engaged with said first stop member and immobilizes said engagement portion when said second stop member is in said engaged position.

42. The invention of claim 41 further comprising a trip member coupled to at least one of said trigger member and said push member, said trip member moveable between an engaged position, wherein said trip member is engaged with one of said first and second stop members after said trigger member has moved along a predetermined portion of said path, and a disengaged position, wherein said trip member disengages said second stop member from said first stop member when said trip member is moved to said engaged position.

43. The invention of claim 42 wherein said first stop member comprises a pivot member engaged with said second stop member, wherein said trip member engages said pivot member when moved to said engaged position.

44. The invention of claim 23 wherein said first portion of said container comprises a valve stem.

45. A method for dispensing a medicament from a container having a first portion moveable relative to a second portion in a longitudinal direction, the method comprising:
providing an actuator comprising a holder having a grippable portion, a trigger member pivotally connected to said holder at a first pivot axis, and a push member connected to said trigger;
engaging at least said first portion of said container with said holder;
pivoting said trigger member about said pivot axis in a first rotational direction toward said grippable portion and thereby moving at least a portion of said trigger member in a lateral direction substantially non-parallel to said longitudinal direction as said trigger member is pivoted in said first and second rotational directions, wherein said pivoting said trigger member comprises moving said trigger member along a path;
pivoting said push member about said pivot axis in said first rotational direction and thereby moving at least a portion of said push member in said longitudinal direction;
engaging at least said second portion of said container with an engagement portion of said push member;
engaging one of said container and said push member with a stop member and thereby immobilizing said engagement portion as said trigger member is pivoted in said first rotational direction along at least a portion of said path; and
moving said second portion of said container relative to said holder and said first portion of said container with said push member in said longitudinal direction as said push member pivots about said pivot axis in said first rotational direction.

46. The invention of claim 45 further comprising pivoting said trigger member and said push member about said pivot axis in a second rotational direction opposite said first rotational direction.

47. The invention of claim 46 further comprising an indicator member rotatably mounted to said holder and a drive mechanism connected between said indicator member and at least one of said trigger member and said push member, and further comprising actuating said drive mechanism with said at least one of said trigger member and said push member as said at least one of said trigger member and said push member are pivoted in at least one of said first and second rotational directions, and rotating said indicator member in incremental amount with said drive mechanism upon a predetermined number of movements of said at least one of said trigger member and said push member in said at least one of said first and second rotational directions.

48. The invention of claim 47 wherein said predetermined number is one movement of said at least one of said trigger member and said push member in said at least one of said first and second rotational directions.

49. The invention of claim 47 wherein said drive mechanism comprises a pawl connected to one of said trigger member and said push member, a worm rotatably mounted to said holder, and a ratchet gear coaxially mounted with said worm, and wherein said indicator member comprises gear teeth meshing with said worm, and wherein said actuating said drive mechanism with said at least one of said trigger member and said push member comprises moving said ratchet gear with said pawl and thereby moving said worm coaxially mounted with said ratchet gear, and moving said indicator member with said worm.

50. The invention of claim 49 further comprising a non-return member connected to said housing, wherein said non-return member is engageable with said ratchet gear and prevents movement of said ratchet gear in at least one direction.

51. The invention of claim 45 wherein said trigger member and said push member are integrally formed as a one-piece member.

52. The invention of claim 45 further comprising biasing said stop member into engagement with said one of said container and said push member with a spring.

53. The invention of claim 45 further comprising engaging said stop member with a trip member coupled to said trigger member after said trigger member has moved along a predetermined portion of said path, disengaging said stop member from said one of said push member and said container with said trip member, and thereafter moving said second portion of said container relative to said holder and said first portion of said container with said engagement portion of said push member as said push member pivots about said pivot axis in said first rotational direction.

54. The invention of claim 53 wherein said stop member comprises a catch member engaging said push member.

55. The invention of claim 53 wherein said moving said second portion of said container relative to said holder and said first portion of said container with said engagement portion of said push member comprises biasing said engagement portion with a spring coupled between said trigger member and said engagement portion.

56. The invention of claim 55 wherein said spring is integrally formed between said trigger member and said engagement portion of said push member.

57. The invention of claim 45 wherein said push member further comprises a biasing member, and wherein said moving said second portion of said container relative to said holder and said first portion of said container with said engagement portion of said push member comprises biasing said engagement portion with a spring disposed between said biasing member and said engagement portion.

58. The invention of claim 57 wherein said biasing member is pivotally connected to said trigger member.

59. The invention of claim 58 engaging said stop member with a trip member coupled to one of said biasing member and said push member after said trigger member has moved along a predetermined portion of said path, disengaging said stop member from said one of said push member and said container with said trip member, and thereafter moving said second portion of said container relative to said holder and said first portion of said container with said engagement portion.

60. The invention of claim 45 wherein said push member comprises a stop portion, and wherein said engaging one of said container and said push member with a stop member comprises engaging a curved surface formed on said stop portion.

61. The invention of claim 60 wherein said curved surface is a first curved surface and wherein said stop member has a second curved surface mating with said first curved surface.

62. The invention of claim 45 further comprising engaging said stop member with a pivot member coupled to said push member, pivoting said pivot member with a trip member coupled to said trigger member after said trigger member has moved along a predetermined portion of said path and thereby disengaging said stop member from said pivot member and thereafter moving said second portion of said container relative to said holder and said first portion of said container with said engagement portion.

63. The invention of claim 45 wherein said stop member comprises a first stop member engaging said second portion of said container in opposition to said push member and a second stop member pivotally secured to said housing, and further comprising engaging said first stop member with said second stop member and thereby immobilizing said engagement portion.

64. The invention of claim 63 further comprising disengaging said second stop member from said first stop member with a trip member coupled to at least one of said trigger member and said push member after said trigger member has moved along a predetermined portion of said path.

65. The invention of claim 45 wherein said first portion of said container comprises a valve stem.

* * * * *